US011067267B2

(12) United States Patent
Neeley et al.

(10) Patent No.: US 11,067,267 B2
(45) Date of Patent: *Jul. 20, 2021

(54) HEAD WEARABLE DEVICES AND METHODS

(71) Applicant: Integra LifeSciences Corporation, Princeton, NJ (US)

(72) Inventors: Brian Neeley, Cottage Grove, WI (US); Greg Falendysz, Sun Prairie, WI (US); Steve Dieter, Oregon, WI (US); Parker Hren, Madison, WI (US); Nick Higbee, Madison, WI (US); Charles David Strubbe, Loveland, OH (US)

(73) Assignee: Integra LifeSciences Corporation, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/916,502

(22) Filed: Jun. 30, 2020

(65) Prior Publication Data

US 2020/0332995 A1    Oct. 22, 2020

Related U.S. Application Data

(63) Continuation of application No. 16/230,277, filed on Dec. 21, 2018, now Pat. No. 10,724,716.
(Continued)

(51) Int. Cl.
*F21V 29/70* (2015.01)
*A61B 90/35* (2016.01)
(Continued)

(52) U.S. Cl.
CPC .............. *F21V 29/70* (2015.01); *A61B 90/30* (2016.02); *A61B 90/35* (2016.02); *F21V 21/084* (2013.01);
(Continued)

(58) Field of Classification Search
CPC ........ F21V 29/70; F21V 29/74; F21V 21/084; F21V 21/30; A61B 90/30; A61B 90/35;
(Continued)

(56) References Cited

U.S. PATENT DOCUMENTS

| 1,453,006 A ‡ | 4/1923 | Day ..................... A61B 1/0692 600/24 |
| 1,632,851 A ‡ | 6/1927 | Reaves ................ A61B 3/0008 600/24 |

(Continued)

FOREIGN PATENT DOCUMENTS

| AU | 2011/329035 B2 ‡ | 1/2015 |
| CA | 2818152 C ‡ | 10/2015 |

(Continued)

OTHER PUBLICATIONS

Notice of Allowance for U.S. Appl. No. 29/665,581 dated Apr. 15, 2020.‡

(Continued)

*Primary Examiner* — Joseph L Williams
*Assistant Examiner* — Jose M Diaz
(74) *Attorney, Agent, or Firm* — Jenkins, Wilson, Taylor & Hunt, P.A.

(57) ABSTRACT

A head wearable device includes a headpiece, a housing attached to the headpiece, a luminaire attached to the headpiece, the luminaire including a luminaire housing and at least one light source located within the luminaire housing, a duct system connecting the luminaire to the housing, a ball joint rotatably connecting the duct system to the luminaire, and an air moving device configured to induce a cooling air flow through an inlet in the luminaire housing, through the heatsink, through the ball joint, through the duct system, and out of an exhaust in the housing attached to of the headpiece.

20 Claims, 26 Drawing Sheets

Related U.S. Application Data

(60) Provisional application No. 62/741,385, filed on Oct. 4, 2018, provisional application No. 62/741,636, filed on Oct. 5, 2018.

(51) Int. Cl.

| | | |
|---|---|---|
| *F21V 21/084* | (2006.01) | |
| *F21V 21/30* | (2006.01) | |
| *A61B 90/30* | (2016.01) | |
| *A61B 90/50* | (2016.01) | |
| *F21Y 115/10* | (2016.01) | |
| *F21W 131/205* | (2006.01) | |
| *F21V 29/74* | (2015.01) | |
| *F21W 131/20* | (2006.01) | |

(52) U.S. Cl.
CPC ........ *F21V 21/30* (2013.01); *A61B 2090/309* (2016.02); *A61B 2090/502* (2016.02); *F21V 29/74* (2015.01); *F21W 2131/20* (2013.01); *F21W 2131/205* (2013.01); *F21Y 2115/10* (2016.08)

(58) Field of Classification Search
CPC ........ A61B 2090/309; A61B 2090/502; A61B 2017/00734; F21W 2131/20; F21W 2131/205; F21L 4/04; A42B 1/244
See application file for complete search history.

(56) References Cited

U.S. PATENT DOCUMENTS

| | | | | |
|---|---|---|---|---|
| 1,688,113 | A ‡ | 10/1928 | Bornkessel | G02B 25/004 600/24 |
| 2,217,359 | A ‡ | 10/1940 | Cooke | F21L 15/14 362/10 |
| 2,437,748 | A ‡ | 3/1948 | Malcolm | A42B 3/145 2/183 |
| 2,883,980 | A ‡ | 4/1959 | Storz, Jr. | A61B 3/0008 600/24 |
| 2,893,379 | A ‡ | 7/1959 | Springer | A61B 3/0008 600/18 |
| 3,008,040 | A ‡ | 11/1961 | Moore | F21V 21/084 362/10 |
| 3,047,876 | A ‡ | 8/1962 | Malcolm, Jr. | A42B 3/145 2/9 |
| 3,285,242 | A ‡ | 11/1966 | Wallace | G02B 6/0008 600/24 |
| 3,470,570 | A ‡ | 10/1969 | Christiansen | B63C 11/30 2/338 |
| 3,513,481 | A ‡ | 5/1970 | Nickerson | A42B 3/145 2/418 |
| 3,555,560 | A ‡ | 1/1971 | Rascke | A42B 3/14 2/416 |
| 3,586,851 | A ‡ | 6/1971 | Rudolph | F21V 9/12 362/29 |
| 3,645,254 | A ‡ | 2/1972 | Burton | G02B 6/0008 600/24 |
| 3,745,993 | A ‡ | 7/1973 | Feinbloom | F21V 13/04 600/24 |
| 3,763,495 | A ‡ | 10/1973 | De Angelis | A61F 9/06 2/8.1 |
| 3,830,230 | A ‡ | 8/1974 | Chester | G02B 6/0008 600/24 |
| 3,947,676 | A ‡ | 3/1976 | Battilana | F21L 4/00 362/10 |
| 3,951,139 | A ‡ | 4/1976 | Kloots | F21L 15/14 600/24 |
| 3,992,722 | A ‡ | 11/1976 | Rhee | A42B 3/18 2/424 |
| 4,104,709 | A ‡ | 8/1978 | Kloots | F21L 14/00 362/10 |
| 4,130,902 | A ‡ | 12/1978 | Mackenroth, III | A42B 1/008 2/171 |
| 4,234,910 | A ‡ | 11/1980 | Price | G02B 6/0008 362/10 |
| 4,290,422 | A ‡ | 9/1981 | Burton | F21L 14/00 600/24 |
| 4,321,659 | A ‡ | 3/1982 | Wheeler | F21V 29/673 362/29 |
| D266,192 | S ‡ | 9/1982 | Feinbloom | D26/39 |
| 4,593,683 | A ‡ | 6/1986 | Blaha | F21L 15/14 362/10 |
| 4,621,283 | A ‡ | 11/1986 | Feinbloom | F21L 15/14 348/77 |
| 4,628,416 | A ‡ | 12/1986 | Dewey | B23K 26/073 362/55 |
| 4,729,499 | A ‡ | 3/1988 | Martin | A45F 5/00 224/18 |
| 4,766,610 | A | 8/1988 | Mattes | |
| D300,868 | S ‡ | 4/1989 | Conforti | D26/39 |
| 4,887,190 | A ‡ | 12/1989 | Sadamune | G02B 6/0006 362/56 |
| 4,918,583 | A ‡ | 4/1990 | Kudo | G02B 3/005 359/61 |
| 4,942,628 | A ‡ | 7/1990 | Freund | A42B 3/145 2/410 |
| 5,001,608 | A ‡ | 3/1991 | Kehrli | A45D 20/12 362/19 |
| 5,042,930 | A ‡ | 8/1991 | Hutt | G02B 7/002 359/37 |
| 5,078,469 | A ‡ | 1/1992 | Clark | A61B 3/132 351/15 |
| 5,099,399 | A ‡ | 3/1992 | Miller | F21V 7/28 362/58 |
| 5,115,382 | A ‡ | 5/1992 | Smith | F21L 4/06 2/906 |
| 5,163,420 | A ‡ | 11/1992 | Van Der Bel | F21L 14/00 362/10 |
| 5,186,534 | A ‡ | 2/1993 | Woodgate | F21V 21/30 362/41 |
| D337,838 | S ‡ | 7/1993 | Van Der Bel | D26/39 |
| 5,268,977 | A ‡ | 12/1993 | Miller | G02B 6/0008 385/33 |
| 5,355,285 | A ‡ | 10/1994 | Hicks | F21L 14/00 362/10 |
| 5,412,811 | A ‡ | 5/1995 | Hildenbrand | A42B 3/0433 2/10 |
| 5,428,517 | A ‡ | 6/1995 | Behringer | F21V 19/0005 362/26 |
| 5,430,620 | A ‡ | 7/1995 | Li | F21L 14/00 362/10 |
| 5,440,462 | A ‡ | 8/1995 | Kim | F21V 14/065 362/10 |
| 5,465,124 | A ‡ | 11/1995 | Nussenbaum | A61B 3/12 351/15 |
| 5,497,295 | A ‡ | 3/1996 | Gehly | G02B 6/2817 362/58 |
| D373,433 | S ‡ | 9/1996 | Feinbloom | D26/39 |
| 5,558,428 | A ‡ | 9/1996 | Lehrer | F21L 14/00 362/10 |
| 5,608,917 | A ‡ | 3/1997 | Landis | A42B 3/14 2/418 |
| 5,619,754 | A ‡ | 4/1997 | Thurwanger | A42B 3/085 2/416 |
| 5,634,704 | A ‡ | 6/1997 | Shikama | G03B 21/208 353/10 |
| 5,638,551 | A ‡ | 6/1997 | Lallemand | A42B 3/085 2/421 |
| D383,229 | S ‡ | 9/1997 | Kiichiro | D26/39 |
| 5,667,291 | A ‡ | 9/1997 | Caplan | F21V 21/084 362/10 |
| 5,709,459 | A ‡ | 1/1998 | Gourgouliatos | F21L 14/00 362/10 |
| 5,732,176 | A ‡ | 3/1998 | Savage, Jr. | G02B 6/32 385/88 |
| 5,769,523 | A ‡ | 6/1998 | Feinbloom | F21V 14/085 362/55 |

(56) References Cited

U.S. PATENT DOCUMENTS

| | | | | |
|---|---|---|---|---|
| 5,774,271 A | ‡ | 6/1998 | Lagerway | F21L 14/00 359/64 |
| D399,580 S | ‡ | 10/1998 | Feinbloom | D26/39 |
| 5,867,320 A | ‡ | 2/1999 | Park | H04N 5/7441 359/61 |
| D406,371 S | ‡ | 3/1999 | Van Der Bel | D26/39 |
| 5,893,635 A | ‡ | 4/1999 | Bhattacharya | F21L 15/02 362/26 |
| 5,898,290 A | ‡ | 4/1999 | Beard | G06F 21/72 307/15 |
| 5,950,245 A | ‡ | 9/1999 | Binduga | A42B 3/145 2/417 |
| D421,148 S | ‡ | 2/2000 | Borders | D26/11 |
| 6,093,468 A | ‡ | 7/2000 | Toms | A41D 13/0506 428/67 |
| 6,113,281 A | ‡ | 9/2000 | Davis | G02B 6/266 385/73 |
| 6,120,161 A | ‡ | 9/2000 | Van Der Bel | G02B 6/0008 362/10 |
| 6,129,662 A | ‡ | 10/2000 | Li | G02B 6/0006 362/57 |
| D441,111 S | ‡ | 4/2001 | Van Der Bel | D24/23 |
| 6,224,227 B1 | ‡ | 5/2001 | Klootz | F21V 33/0052 348/37 |
| 6,298,497 B1 | ‡ | 10/2001 | Chartrand | A42B 3/12 2/414 |
| 6,321,193 B1 | ‡ | 11/2001 | Nystrom | H03M 7/3082 704/22 |
| 6,341,382 B1 | ‡ | 1/2002 | Ryvin | A42B 3/145 2/417 |
| 6,457,838 B1 | ‡ | 10/2002 | Dugmore | F21L 15/14 362/10 |
| 6,567,993 B2 | ‡ | 5/2003 | Robertson | A42B 3/00 2/171 |
| 6,639,733 B2 | ‡ | 10/2003 | Minano | F21V 7/04 359/72 |
| 6,650,538 B1 | ‡ | 11/2003 | Chu | H01L 23/467 165/12 |
| D484,436 S | ‡ | 12/2003 | Landry | D11/20 |
| D484,437 S | ‡ | 12/2003 | Doyon | D11/20 |
| 6,708,376 B1 | ‡ | 3/2004 | Landry | A42B 3/145 2/418 |
| D489,838 S | ‡ | 5/2004 | Opolka | D26/39 |
| D503,499 S | ‡ | 3/2005 | Howard | D29/12 |
| 6,865,285 B1 | ‡ | 3/2005 | Villa-Aleman | G06K 9/00013 362/10 |
| 6,890,086 B2 | ‡ | 5/2005 | Shiu | H05B 45/00 362/24 |
| 6,896,381 B2 | ‡ | 5/2005 | Benitez | G02B 19/0061 359/85 |
| 6,896,389 B1 | ‡ | 5/2005 | Paul | F21V 21/084 362/10 |
| 6,908,208 B1 | ‡ | 6/2005 | Hyde | F21L 4/06 362/10 |
| 6,921,920 B2 | ‡ | 7/2005 | Kazakevich | F21V 5/007 257/81 |
| 6,955,444 B2 | ‡ | 10/2005 | Gupta | F21L 2/00 362/10 |
| 6,966,074 B2 | ‡ | 11/2005 | Huh | A42B 3/14 2/181 |
| 6,999,318 B2 | ‡ | 2/2006 | Newby | F21K 9/00 361/71 |
| 7,000,262 B2 | ‡ | 2/2006 | Bielefeld | A42B 3/14 2/181 |
| 7,043,772 B2 | ‡ | 5/2006 | Bielefeld | A42B 3/145 2/418 |
| RE39,162 E | ‡ | 7/2006 | Caplan | F21V 21/084 362/10 |
| 7,131,760 B2 | ‡ | 11/2006 | Mayer | F21V 29/74 362/55 |
| 7,134,763 B2 | ‡ | 11/2006 | Klootz | G02B 6/0008 362/10 |
| 7,144,140 B2 | ‡ | 12/2006 | Sun | F21K 9/233 362/37 |
| 7,153,015 B2 | ‡ | 12/2006 | Brukilacchio | A61N 5/062 362/55 |
| 7,163,327 B2 | ‡ | 1/2007 | Henson | F21S 41/143 362/55 |
| 7,174,575 B1 | ‡ | 2/2007 | Scherer | A42B 3/145 2/418 |
| 7,181,378 B2 | ‡ | 2/2007 | Benitez | G02B 19/0028 703/2 |
| 7,192,151 B2 | ‡ | 3/2007 | Clupper | A42B 3/044 2/171 |
| D539,952 S | ‡ | 4/2007 | Iranyi | D26/39 |
| 7,210,810 B1 | ‡ | 5/2007 | Iversen | A61B 90/35 362/10 |
| 7,229,201 B2 | ‡ | 6/2007 | Krupa | G02B 6/0006 362/55 |
| 7,229,202 B2 | ‡ | 6/2007 | Sander | G02B 21/06 359/37 |
| 7,258,464 B2 | ‡ | 8/2007 | Morris | F21V 29/004 362/26 |
| 7,270,459 B2 | ‡ | 9/2007 | Waring | G02B 6/0006 362/30 |
| 7,286,296 B2 | ‡ | 10/2007 | Chaves | G02B 6/0046 359/64 |
| 7,300,175 B2 | ‡ | 11/2007 | Brukilacchio | A61N 5/062 362/23 |
| D560,009 S | ‡ | 1/2008 | Spartano | D26/39 |
| 7,314,294 B1 | ‡ | 1/2008 | Moore | F21V 25/00 362/10 |
| 7,314,300 B1 | ‡ | 1/2008 | Dorr | A61B 90/35 362/58 |
| 7,360,924 B2 | ‡ | 4/2008 | Henson | B60Q 1/0011 362/24 |
| 7,380,962 B2 | ‡ | 6/2008 | Chaves | G02B 27/126 362/29 |
| D572,853 S | ‡ | 7/2008 | Heine | D26/39 |
| 7,441,282 B2 | ‡ | 10/2008 | Heine | A61B 90/50 2/418 |
| 7,465,078 B2 | ‡ | 12/2008 | Chang | F21V 21/0885 362/37 |
| D586,932 S | ‡ | 2/2009 | Feinbloom | D26/39 |
| 7,488,088 B2 | ‡ | 2/2009 | Brukilacchio | A61N 5/062 362/23 |
| 7,488,101 B2 | ‡ | 2/2009 | Brukilacchio | A61N 5/062 362/23 |
| 7,513,660 B2 | ‡ | 4/2009 | Spartano | F21V 29/15 362/37 |
| 7,565,040 B2 | ‡ | 7/2009 | Nagaeda | G02F 1/0316 385/11 |
| 7,618,159 B2 | ‡ | 11/2009 | Tamburrino | F21V 11/10 362/32 |
| D608,479 S | ‡ | 1/2010 | Heine | D26/39 |
| D615,225 S | ‡ | 5/2010 | DeBrunner | D26/39 |
| D615,678 S | ‡ | 5/2010 | DeBrunner | D26/39 |
| D615,679 S | ‡ | 5/2010 | Ferguson | D26/39 |
| 7,710,569 B2 | ‡ | 5/2010 | Zuluaga | A61B 90/36 356/44 |
| 7,724,440 B2 | ‡ | 5/2010 | Chaves | G02B 27/143 359/62 |
| 7,744,219 B2 | ‡ | 6/2010 | Davis | A61B 3/0094 351/22 |
| 7,755,838 B2 | ‡ | 7/2010 | Chaves | G02B 27/0994 359/63 |
| D621,535 S | ‡ | 8/2010 | Heine | D26/39 |
| D624,221 S | ‡ | 9/2010 | DeBrunner | D26/39 |
| D628,307 S | ‡ | 11/2010 | Krause-Bonte | D24/23 |
| 7,829,191 B2 | ‡ | 11/2010 | Frick | F21V 9/06 428/42 |
| D630,766 S | ‡ | 1/2011 | Harbin | D24/23 |
| 7,871,174 B2 | ‡ | 1/2011 | Heine | F21L 4/00 362/10 |
| 7,874,293 B2 | ‡ | 1/2011 | Gunaratnam | A61M 16/0633 128/20 |
| D635,286 S | | 3/2011 | Schussler | |

(56) References Cited

U.S. PATENT DOCUMENTS

| | | | |
|---|---|---|---|
| 7,918,578 B2 ‡ | 4/2011 | Spartano | F21V 29/70 362/10 |
| 7,926,967 B2 ‡ | 4/2011 | Spartano | F21V 23/0414 362/10 |
| 7,972,028 B2 ‡ | 7/2011 | Durand | F21K 9/00 362/23 |
| D648,882 S ‡ | 11/2011 | Halm | D26/51 |
| 8,075,147 B2 ‡ | 12/2011 | Chaves | F21K 9/61 362/84 |
| 8,075,154 B2 ‡ | 12/2011 | Thomas | F21V 29/80 362/10 |
| 8,177,384 B2 ‡ | 5/2012 | Boulan | A42B 3/044 362/10 |
| 8,262,224 B2 ‡ | 9/2012 | Nussenbaum | A61B 3/132 351/21 |
| 8,348,448 B2 ‡ | 1/2013 | Orozco | A42B 1/244 362/10 |
| 8,359,672 B2 ‡ | 1/2013 | Moelker | A42B 3/145 2/418 |
| 8,427,014 B2 ‡ | 4/2013 | Eckhoff | H02J 50/20 307/15 |
| D685,938 S ‡ | 7/2013 | Baker | D26/39 |
| 8,517,556 B2 ‡ | 8/2013 | Boulan | A42B 3/044 362/10 |
| 8,529,082 B1 ‡ | 9/2013 | Baker | A42B 3/044 362/10 |
| 8,550,650 B1 ‡ | 10/2013 | McGinty | A42B 3/044 362/10 |
| 8,696,552 B2 ‡ | 4/2014 | Whitman | A61B 1/00135 600/14 |
| 8,713,718 B2 ‡ | 5/2014 | Moelker | A42B 1/22 2/418 |
| 8,729,851 B2 ‡ | 5/2014 | Bobbin | H01M 10/0525 320/10 |
| D706,474 S ‡ | 6/2014 | Ferguson | D26/39 |
| 8,789,962 B2 ‡ | 7/2014 | Crowder | A61B 90/35 362/10 |
| D713,575 S ‡ | 9/2014 | Ferguson | D26/39 |
| 8,899,774 B2 ‡ | 12/2014 | Strong | A42B 1/244 362/10 |
| 8,900,138 B2 ‡ | 12/2014 | Horvath | H05B 47/28 600/24 |
| 8,911,130 B2 ‡ | 12/2014 | Richart | F21K 9/61 362/55 |
| 8,922,159 B2 ‡ | 12/2014 | Bobbin | H01M 50/572 320/10 |
| D721,842 S ‡ | 1/2015 | Opolka | D26/39 |
| 9,033,505 B2 ‡ | 5/2015 | Kim | A61B 90/35 351/21 |
| 9,039,224 B2 ‡ | 5/2015 | Delaney | A61B 90/35 362/10 |
| 9,089,296 B2 ‡ | 7/2015 | Heine | A61B 1/00034 |
| 9,091,428 B2 ‡ | 7/2015 | Ferguson | F21V 33/0068 |
| 9,103,539 B2 ‡ | 8/2015 | Baker | A42B 3/044 |
| D739,061 S ‡ | 9/2015 | Petzl | D26/39 |
| 9,131,744 B2 ‡ | 9/2015 | Erb | A42B 3/124 |
| D742,049 S ‡ | 10/2015 | Baker | D26/39 |
| D743,596 S ‡ | 11/2015 | Ormsbee | D26/39 |
| D745,731 S ‡ | 12/2015 | Zimmerli | D26/39 |
| 9,206,969 B2 ‡ | 12/2015 | Bushee | F21V 33/008 |
| 9,219,849 B2 ‡ | 12/2015 | Feinbloom | H04N 5/2252 |
| 9,234,653 B2 ‡ | 1/2016 | Ferguson | F21V 21/084 |
| 9,263,718 B2 ‡ | 2/2016 | Davidson | H01M 50/209 |
| 9,265,295 B2 ‡ | 2/2016 | Boulan | A42B 3/044 |
| 9,271,636 B2 ‡ | 3/2016 | Teder | A61B 1/0684 |
| 9,326,827 B2 ‡ | 5/2016 | Estwick | A61B 90/35 |
| 9,351,799 B2 ‡ | 5/2016 | Ferguson | A61B 1/0692 |
| 9,362,762 B2 ‡ | 6/2016 | Bobbin | H02J 7/0029 |
| 9,366,401 B2 ‡ | 6/2016 | Koyama | F21V 21/30 |
| 9,386,912 B2 ‡ | 7/2016 | Hoadley | G02B 6/0006 |
| 9,400,101 B2 ‡ | 7/2016 | Strong | A61B 1/128 |
| 9,707,707 B2 ‡ | 7/2017 | Ferguson | B29C 39/10 |
| 9,775,394 B2 ‡ | 10/2017 | Dagan | A42B 3/12 |
| 9,833,033 B2 ‡ | 12/2017 | Erb | A42B 3/128 |
| D820,468 S | 6/2018 | Hagood et al. | |
| D821,006 S ‡ | 6/2018 | Chen | D26/39 |
| 10,253,964 B2 ‡ | 4/2019 | Strong | A61B 5/6814 |
| D884,236 S ‡ | 5/2020 | Africa | D26/39 |
| 10,724,716 B2 * | 7/2020 | Neeley | A61B 90/35 |
| D901,737 S | 11/2020 | Neeley et al. | |
| 10,830,428 B2 | 11/2020 | Africa et al. | |
| 2002/0085372 A1 ‡ | 7/2002 | Lehrer | F21V 5/04 362/10 |
| 2003/0042493 A1 ‡ | 3/2003 | Kazakevich | A61B 1/0607 257/98 |
| 2004/0120151 A1 ‡ | 6/2004 | Ostler | G01N 21/645 362/29 |
| 2004/0149998 A1 ‡ | 8/2004 | Henson | F21S 41/24 257/98 |
| 2004/0151008 A1 ‡ | 8/2004 | Artsyukhovich | A61F 9/00823 362/57 |
| 2005/0128735 A1 ‡ | 6/2005 | Atkins | A61B 3/12 362/10 |
| 2005/0128752 A1 ‡ | 6/2005 | Ewington | F21S 4/28 362/29 |
| 2006/0245175 A1 ‡ | 11/2006 | Heine | A61B 90/50 362/10 |
| 2006/0250771 A1 ‡ | 11/2006 | Heine | F21V 29/70 361/69 |
| 2006/0285315 A1 ‡ | 12/2006 | Tufenkjian | A61B 90/35 362/10 |
| 2006/0285316 A1 ‡ | 12/2006 | Tufenkjian | F21V 21/084 362/10 |
| 2006/0285323 A1 ‡ | 12/2006 | Fowler | G01J 3/10 362/23 |
| 2007/0097702 A1 ‡ | 5/2007 | Crowder | A61B 90/36 362/57 |
| 2007/0097703 A1 ‡ | 5/2007 | Goldfain | G02B 19/0066 362/57 |
| 2007/0220649 A1 ‡ | 9/2007 | Huh | A42B 3/226 2/9 |
| 2007/0253202 A1 ‡ | 11/2007 | Wu | F21V 29/767 362/29 |
| 2008/0239707 A1 | 10/2008 | Feinbloom | |
| 2008/0316733 A1 ‡ | 12/2008 | Spartano | F21V 14/06 362/10 |
| 2009/0116252 A1 ‡ | 5/2009 | Kille | H05K 1/0204 362/37 |
| 2009/0161348 A1 ‡ | 6/2009 | Spartano | F21V 29/70 362/10 |
| 2009/0225534 A1 ‡ | 9/2009 | Thomas | F21V 21/084 362/10 |
| 2009/0227847 A1 ‡ | 9/2009 | Tepper | A61L 2/084 600/24 |
| 2009/0229041 A1 ‡ | 9/2009 | Tufenkjian | A42B 1/24 2/414 |
| 2010/0093267 A1 | 4/2010 | Hogh | |
| 2010/0277894 A1 ‡ | 11/2010 | Kim | F21V 21/145 362/10 |
| 2011/0013383 A1 ‡ | 1/2011 | Medinis | F21V 29/02 362/10 |
| 2011/0051432 A1 ‡ | 3/2011 | Heine | F21V 29/713 362/37 |
| 2011/0160541 A1 ‡ | 6/2011 | Koyama | F21V 21/084 600/24 |
| 2012/0120635 A1 ‡ | 5/2012 | Strong | F21V 5/008 362/10 |
| 2012/0204870 A1 ‡ | 8/2012 | McAuley | A61M 16/0616 128/20 |
| 2012/0281429 A1 ‡ | 11/2012 | Orozco | A42B 1/244 362/57 |
| 2012/0314428 A1 ‡ | 12/2012 | Thomas | F21V 29/80 362/37 |
| 2013/0111648 A1 ‡ | 5/2013 | Huh | A42B 3/14 2/181 |
| 2013/0121005 A1 ‡ | 5/2013 | Dahmen | F21L 15/14 362/31 |
| 2013/0204094 A1 ‡ | 8/2013 | Fiebel | A61B 1/06 600/24 |

(56) References Cited

U.S. PATENT DOCUMENTS

| | | | |
|---|---|---|---|
| 2013/0340147 A1 | 12/2013 | Giles | |
| 2014/0275806 A1 ‡ | 9/2014 | Gunday | A61B 90/30 600/24 |
| 2014/0334132 A1 ‡ | 11/2014 | Ferguson | F21V 21/084 362/10 |
| 2014/0340760 A1 ‡ | 11/2014 | Baumann | G02B 27/283 359/63 |
| 2015/0059064 A1 ‡ | 3/2015 | Klotz | A42B 3/324 2/417 |
| 2015/0153035 A1 ‡ | 6/2015 | Strong | F21V 11/10 362/10 |
| 2016/0123563 A1 ‡ | 5/2016 | Ferguson | F21V 21/084 362/27 |
| 2016/0334092 A1 ‡ | 11/2016 | Strong | F21V 29/61 |
| 2017/0049178 A1 | 2/2017 | Durocher | |
| 2017/0157352 A1 | 6/2017 | Ng et al. | |
| 2017/0340044 A1 ‡ | 11/2017 | Balderama Arenas | A42C 5/02 |
| 2018/0132556 A1 | 5/2018 | Laperriere et al. | |
| 2020/0109839 A1 | 4/2020 | Neeley et al. | |
| 2020/0109840 A1 ‡ | 4/2020 | Africa | A61B 90/35 |
| 2020/0109847 A1 ‡ | 4/2020 | Poggio | A61B 90/30 |

FOREIGN PATENT DOCUMENTS

| | | | |
|---|---|---|---|
| CN | 2820148 Y | ‡ | 9/2006 |
| CN | 100432526 C | ‡ | 11/2008 |
| CN | 101377286 A | ‡ | 3/2009 |
| CN | 201232858 Y | ‡ | 5/2009 |
| CN | 204765540 U | ‡ | 11/2015 |
| DE | 10 2009 020112 A1 | ‡ | 7/2010 |
| DE | 10 2010 047477 B4 | ‡ | 2/2014 |
| EP | 2589308 A1 | ‡ | 5/2013 |
| EP | 2641018 B1 | ‡ | 1/2017 |
| EP | 3143888 A1 | ‡ | 3/2017 |
| FR | 2604798 A1 | ‡ | 4/1988 |
| JP | H08-288205 A | ‡ | 11/1996 |
| JP | 2006-147373 A | ‡ | 6/2006 |
| JP | 2008-186694 | ‡ | 8/2008 |
| JP | 2008-198468 A | ‡ | 8/2008 |
| JP | 2008-227127 A | ‡ | 9/2008 |
| JP | 2010-046566 A | ‡ | 3/2010 |
| JP | 5627795 B2 | ‡ | 11/2014 |
| WO | WO 02/099332 A1 | ‡ | 12/2002 |
| WO | WO 2007/051173 A2 | ‡ | 5/2007 |
| WO | WO 2009/048794 A1 | ‡ | 4/2009 |
| WO | WO 2010/007785 A1 | ‡ | 1/2010 |
| WO | WO 2011/100193 A1 | ‡ | 8/2011 |
| WO | WO 2012/068116 A1 | ‡ | 5/2012 |
| WO | WO 2012/087783 A1 | ‡ | 6/2012 |
| WO | WO 2014/146600 A1 | ‡ | 9/2014 |
| WO | WO 2014/202114 A1 | ‡ | 12/2014 |
| WO | WO 2020/072086 A1 | ‡ | 4/2020 |
| WO | WO 2020/072087 A1 | ‡ | 4/2020 |
| WO | WO 2020/072088 A1 | ‡ | 4/2020 |

OTHER PUBLICATIONS

Non-Final Office Action for U.S. Appl. No. 29/665,582 dated Oct. 18, 2019.‡
Non-Final Office Action for U.S. Appl. No. 29/665,581 dated Oct. 18, 2019.‡
Stryker, Flyte Steri-Shield Personal Protection System. Stryker Australia, 2014.‡
Non-Final Office Action for U.S. Appl. No. 16/230,210 dated May 27, 2020.‡
Notice of Allowance for U.S. Appl. No. 29/665,582 dated Jan. 15, 2020.‡
Final Office Action for U.S. Appl. No. 29/665,581 dated Jan. 10, 2020.‡
Integra Lighting Solutions 2014 [retrieved from https://www.integralife.com/file/general/1453798333 on Jun. 28, 2019].‡
Integra LED Lighting Tri-Fold Brochure 2014 [retrieved from https://www.integralife.com/file/general/1453798461-1 on Jun. 28, 2019].‡
Non-Final Office Action for U.S. Appl. No. 13/069,288 dated Aug. 29, 2013.‡
Integra LED Headlight System Sell Sheet 2012 [retrieved from https://www.integralife.com/file/general/1453795781 on Jun. 28, 2019].‡
Japanese Office Action and Search Report for Application No. 2013/539950 dated Apr. 17, 2014.‡
Notice of Allowance for U.S. Appl. No. 13/069,288 dated Aug. 1, 2014.‡
Final Office Action for U.S. Appl. No. 13/069,288 dated Jan. 22, 2014.‡
Australian Examination Report for Application No. 2011329035 dated Apr. 14, 2014.‡
International Search Report and Written Opinion for PCT/US2011/060799 dated Mar. 29, 2012.‡
Non-Final Office Action for U.S. Appl. No. 13/069,288 dated Dec. 13, 2012.‡
Non-Final Office Action for U.S. Appl. No. 12/048,050 dated Mar. 28, 2011.‡
Final Office Action for U.S. Appl. No. 13/069,288 dated Jun. 17, 2013.‡
International Search Report for Application No. PCT/US 06/60317 dated Apr. 2. 2008.‡
"LED Surgical Headlight Technical Review," Welch Allyn, Oct. 22, 2009.‡
Petzl Elios Vision Helmet, Spring 2007 Moosejaw Website; http://www.moosejawlowdown.com/moosejaw . . . (3 pages).‡
Notice of Allowance for U.S. Appl. No. 15/218,654 dated Nov. 23, 2018.‡
International Search Report and Written Opinion for Application No. PCT/US2018/067220 dated May 22, 2019.‡
International Search Report and Written Opinion for Application No. PCT/US2018/067224 dated Jun. 4, 2019.‡
International Search Report and Written Opinion for Application No. PCT/US2018/067231 dated Jun. 4, 2019.‡
SSL-5500 Wireless LED Headlight, Sunoptic Technologies, 2018 [retrieved from http://sunoptictech.com/ssl-5500-wireless-led-headlight/ on Jun. 28, 2019].‡
Non-Final Office Action for U.S. Appl. No. 15/218,654 dated Mar. 7, 2018.‡
TITAN 9000-II LED Headlight System Operation Manual SSL-900041, LIT-224 Sunoptic Surgical, pp. 1-50, 2017.‡
SSL 9500 LED Headlight System, Sunoptic Technologies, 2018 [retrieved from http://sunoptictech.com/ssl-9500-led-headlight/ on Jun. 28, 2019].‡
Australian Examination Report for Application No. 2011329035 dated Nov. 6, 2014.‡
European Office Action for Application No. 11 801 882.9 dated Feb. 16, 2015.‡
Canadian Office Action for Application No. 2,818,152 dated Aug. 12, 2014.‡
European Office Action for Application No. 11 801 882.9 dated Sep. 23, 2015.‡
Surgical Illumination and Visualization Systems, Integra Brochure, 12 pages total, 2016.‡
Notice of Allowance for U.S. Appl. No. 14/553,512 dated May 24, 2016.‡
Supplemental Notice of Allowance for U.S. Appl. No. 14/553,512 dated Jun. 10, 2016.‡
Notice of Allowance for U.S. Appl. No. 29/665,581 dated Aug. 7, 2020.
"LED Surgical Headlight Technical Review," Welch Allyn, Oct. 2, 2009.
Final Office Action for U.S. Appl. No. 13/069,288 dated Aug. 29, 2013.
Integra LED Lighting Tri-Fold Brochure 2014 [retrieved from https://www.integralife.com/file/general/1453798461-1 on Jun. 28, 2019].
TITAN 9000-II LED Headlight System Operation Manual SSL-9000-II, LIT-224 Sunoptic Surgical, pp. 1-50, 2017.
Notice of Allowance for U.S. Appl. No. 16/230,277 dated Feb. 10, 2020.

(56) References Cited

OTHER PUBLICATIONS

Non-Final Office Action for U.S. Appl. No. 16/230,361 dated Apr. 27, 2020.
Notice of Allowance for U.S. Appl. No. 16/230,361 dated Sep. 10, 2020.
Final Office Action for U.S. Appl. No. 16/230,210 dated Nov. 2, 2020.
Non-Final Office Action for U.S. Appl. No. 29/748,382 dated Dec. 4, 2020.

\* cited by examiner
‡ imported from a related application

HEAD WEARABLE DEVICES AND METHODS

CROSS-REFERENCE TO RELATED APPLICATIONS

This application is a continuation of and claims the benefit of and priority to U.S. patent application Ser. No. 16/230,277 filed on Dec. 21, 2018, which claims the benefit of and priority to both U.S. Provisional Patent Application Ser. No. 62/741,385, filed on Oct. 4, 2018, and U.S. Provisional Patent Application Ser. No. 62/741,636, filed on Oct. 5, 2018, the disclosures of which are incorporated by reference herein in their entireties.

TECHNICAL FIELD

The present disclosure relates generally to devices to be adjustably worn on a human head to provide supplemental light for surgical and medical procedures. Specifically, the present disclosure relates to light emitting diode ("LED") based surgical headlight systems.

BACKGROUND

Existing surgical headlights require a significant amount of light to provide sufficient illumination for the surgeon during a typical case. Surgical headlights are also preferably lightweight so that neck and head fatigue of the surgeon is minimized. LEDs are semiconductor devices that emit light by application of electrical power (watts). LEDs are a feasible light source for a surgical headlight luminaire. However, the problem is that LEDs generate heat. One of the major challenges LEDs pose in many applications is removing the heat from the LED. Excess heat must be removed so that the semiconductor junction temperature does not exceed recommended maximum temperature. In addition, as the junction temperature of the LED rises, the efficiency also drops. LED light output is limited by its maximum heat junction temperature, so to increase light output without damaging the LED or reducing its operating efficiency, heat must be transferred quickly and efficiently.

There remains a need for LED surgical headlights which allow efficient transfer of heat energy from the LED so that the LED is sufficiently cooled and retains its light output performance and reliability.

Furthermore, surgical headlights are worn by healthcare professionals to provide illumination to aid visualization during surgical, diagnostic, or therapeutic procedures. Headlight devices typically include a headband, a luminaire, and other components and accessories, which could cause discomfort or neck and head fatigue in the wearer, particularly when worn in a long procedure. Thus, there remains a need for surgical headlight devices and systems that provide enhanced comfort when worn by a wearer (e.g., a surgeon) for an extended period of time.

SUMMARY

It is an object of the present disclosure to provide a head wearable device comprising a headpiece; a housing on a top surface of the headpiece; a luminaire attached to the headpiece, the luminaire comprising a luminaire housing and at least one light source thermally connected to a heatsink, the at least one light source and the heatsink being located within the luminaire housing; a duct system connected between the luminaire and the housing; a ball joint rotatably connecting the duct system to the luminaire; an air moving device located configured to induce a cooling air flow through an inlet formed in the luminaire housing, through the heatsink, through the ball joint, through the duct system, and out of an exhaust formed in the housing on the top surface of the headpiece; and a controller configured to monitor a temperature of the at least one light source and to modulate an operational setting of the air moving device to maintain the temperature of the at least one light source within a predetermined operating range.

It is a further object of the present disclosure to provide a head wearable device comprising: a headpiece comprising a headband comprising a top strap and at least two lateral straps; and an occipital basket comprising a strap, the occipital basket being attached to the headband by at least one lateral extension strap pivotably attached by a hinge to a distal end of each respective lateral strap of the headband; a first housing attached to an outer surface of the top strap of the headband; a depth adjuster attached to the first housing, the depth adjuster comprising a first gear rotatably fixed to a first knob; herein the strap of the occipital basket comprises a slot with a plurality of teeth formed around a longitudinal edge of the slot; wherein the first gear is captively held within the slot and engages with the plurality of teeth; wherein a rotary movement of the first gear causes a longitudinal movement of the strap of the occipital basket to change a distance between the occipital basket and the first housing; wherein a depth of the headpiece changes when the distance between the occipital basket and the first housing changes, or increases or decreases; and wherein the strap comprises a first visual index comprising a first plurality of sequential characters, each of which correspond to one of a plurality of predetermined depth settings of the headpiece; and a second housing attached to an outer surface of the occipital basket; a circumferential adjuster at an outer surface of the occipital basket, the circumferential adjuster comprising a second gear rotatably fixed to a second knob; wherein the lateral extension straps each comprise a slot with a plurality of teeth formed around a longitudinal edge of the slot; wherein the second gear is captively held within the slot of each lateral extension strap and engages with the plurality of teeth of each of the lateral extension straps; wherein a rotary movement of the second gear causes a longitudinal movement of the lateral extension straps to change a circumference of the headpiece; and wherein at least one of the lateral extension straps comprises a second visual index comprising a second plurality of sequential characters, each of which correspond to one of a plurality of predetermined circumferential settings of the headpiece; wherein the lateral extension straps rotate about the hinge, relative to the lateral straps as the depth of the headpiece changes.

Still another object of the present disclosure is to provide a method of adjusting a size of a headpiece of a head wearable device to a head size of a wearer, the headpiece comprising a headband and an occipital basket. The method comprises attaching a first housing to an external surface of a top strap of the headband; inserting a strap of the occipital basket at least partially into the first housing; engaging a first gear with a plurality of teeth formed in a slot, which is longitudinally oriented along a length of the strap of the occipital basket; turning a first knob, which is rotationally locked to the first gear, to adjust a depth of the headpiece; attaching a second housing to an external surface of the occipital basket; inserting an end of at least two lateral extension straps into the second housing, with the end of a first lateral extension strap being inserted from an opposite end of the housing from the end of a second lateral extension strap, wherein the two lateral extension straps are hingedly attached to lateral straps of the headband to define a circumference of the headpiece; engaging a second gear with a plurality of teeth formed in a slot of each of the lateral extension straps such that the second gear is engaged with both of the lateral extension straps; and turning a second knob, which is rotationally locked to the second gear, to adjust a circumference of the headpiece.

In another object of the present disclosure, headlight devices with a padding system are provided. Such headlight devices comprise a headband having a rear portion, two side portions, and a top portion, each of which have a respective inner surface; a padding system comprising a rear pad, which is attached to the inner surface of the rear portion of the headband; a side pad attached to the inner surfaces of the two side portions of the headband; a top pad attached to the inner surface of the top portion of the headband; and, optionally, a brow pad attached to the inner surface of the headband at an intersection of the top portion and the two side portions; wherein at least one of the rear pad and the brow pad comprises a first layer of a first cushioning material having a first durometer, and a second layer of a second cushioning material having a second durometer that is harder than the first durometer.

According to some embodiments of the present subject matter, the first cushioning material is silicone foam having a first durometer, and the second cushioning material is silicone foam having a second durometer that is harder than the first durometer; the second layer of the second cushioning material is closer than the first layer of the first cushioning material to the inner surface of the headband.

According to further embodiments of the present subject matter, the first layer of the first cushioning material and the second layer of the second cushioning material are each perforated; the majority of the perforations in the first layer of the first cushioning material may be generally circular, and the majority of the perforations in the second layer of the second cushioning material may be in a shape other than circular. For example, the perforations in the second layer of the second cushioning material are generally square or rectangular, or generally in a grid-like pattern.

In an aspect of the present disclosure, the second layer of the second cushioning material has more open space on its upper or lower surface due to perforations than the first layer of the first cushioning material. In another aspect of the present disclosure, the total volume of cavity due to perforations in the second layer of the second cushioning material is higher than the total volume of cavity in the first layer of the first cushioning material.

In additional embodiments of the present subject matter, the rear pad has an inner surface in contact with a wearer and an outer surface attached to the inner surface of the rear portion of the headband, and the rear pad comprises a recess on its inner surface; at least one of the top pad and the side pad may comprises urethane foam and forms segments.

It is another object of the present disclosure to provide a headlight device comprising a headband for encircling the head of a wearer; a padding system comprising a pad removably attached to at least a portion of the headband; wherein the pad comprises a first layer of a first cushioning material having a first durometer, and a second layer of a second cushioning material having a second durometer that is harder than the first durometer; and wherein the first layer is perforated in a first perforation pattern, and the second layer is perforated in a second perforation pattern that differs from the first perforation pattern.

In some embodiments, the perforations in the first layer are generally in a first perforation shape and the perforations in the second layer are generally in a second perforation shape that differs from the first perforation shape. The perforation patterns can be chosen taking into consideration the softness and density of each layer specific to the cushioning material used. Punching holes or otherwise creating perforation or cavity in the cushioning material reduces the weight of the padding and thus the stress on the wearer, but the removal of cushioning material may reduce the support that the layer can provide. The perforations in the layers of cushioning material also improve heat dissipation and airflow. Perforation patterns are selected to achieve a desired level of support and comfort.

According to some embodiments of the present subject matter, a headlight device is provided, the headlight device comprising: a headband for encircling the head of a wearer; a padding system comprising a rear pad removably attached to at least a portion of the headband; wherein the rear pad comprises a first layer of a first cushioning material having a first durometer, and a second layer of a second cushioning material having a second durometer that is different from the first durometer; wherein the first layer is perforated in a first perforation pattern, and the second layer is perforated in a second perforation pattern that differs from the first perforation pattern; wherein the first layer comprises an inner surface in contact with a wearer; wherein the second layer comprises an outer surface attached to the inner surface of the rear portion of the headband; and wherein the rear pad comprises a recess on an inner surface thereof.

Although the embodiments of headlight devices are shown herein, the features of the padding systems disclosed herein can be applied to other head wearable devices. Other features and advantages of the present subject matter will become more apparent from the following detailed description of the subject matter, when taken in conjunction with the accompanying example drawings.

BRIEF DESCRIPTION OF THE DRAWINGS

A full and enabling disclosure of the present subject matter is set forth more in the remainder of the specification, including reference to the accompanying, example figures, in which.

DETAILED DESCRIPTION

Figure 1:
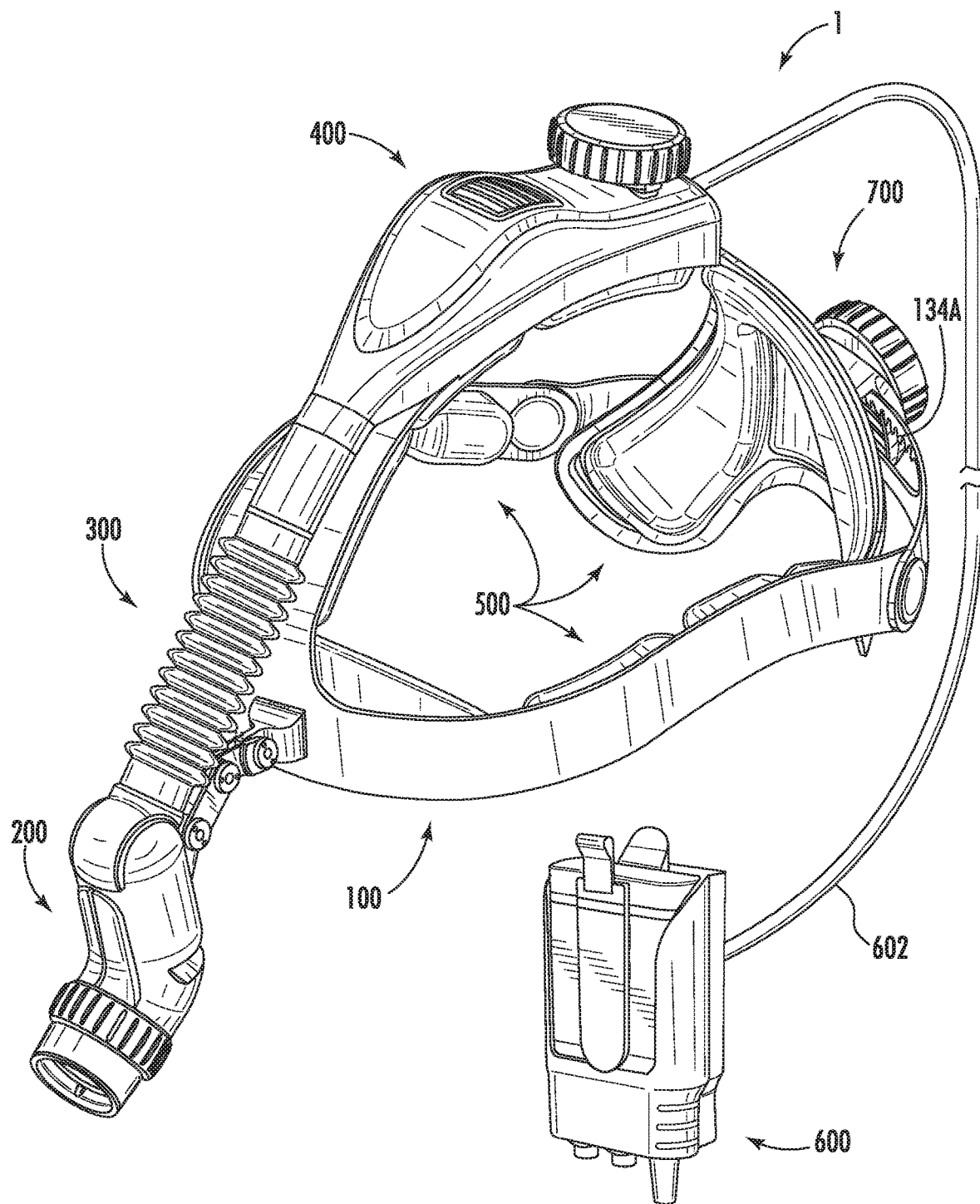
FIGS. 1-7 are respective directional perspective views of an embodiment of the head wearable device, in accordance with the disclosure herein.
Figure 2:
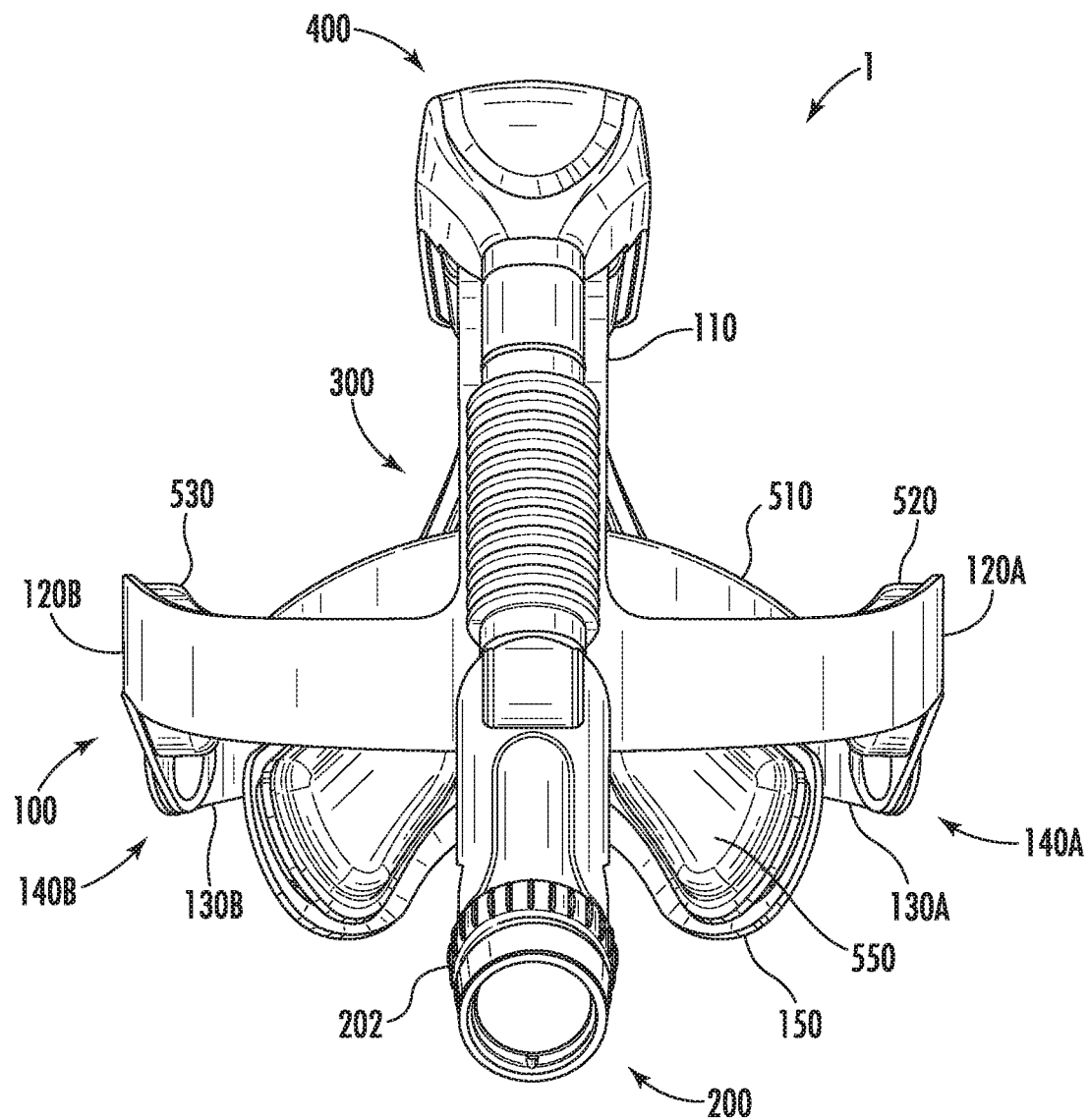
Figure 3:
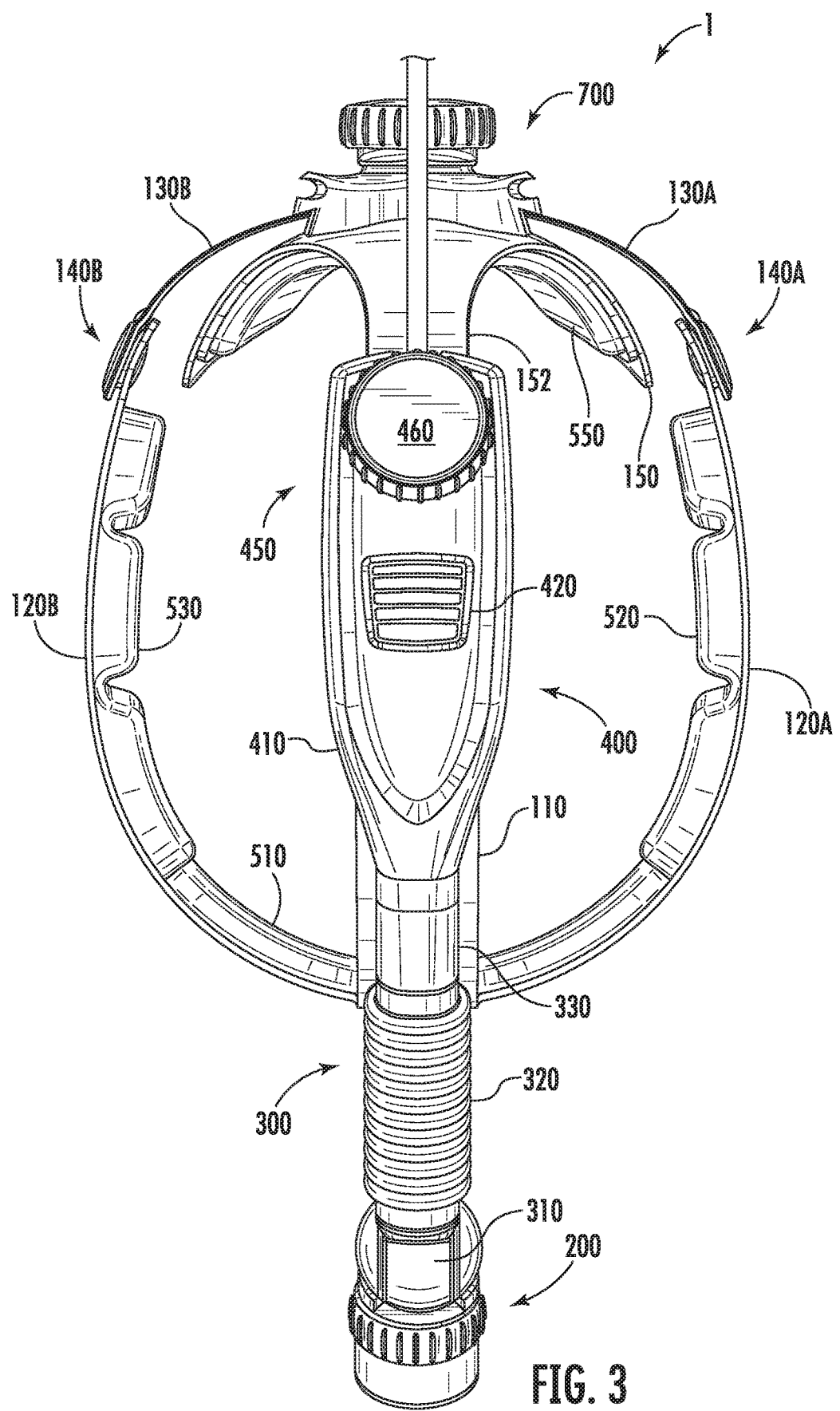
Figure 4:
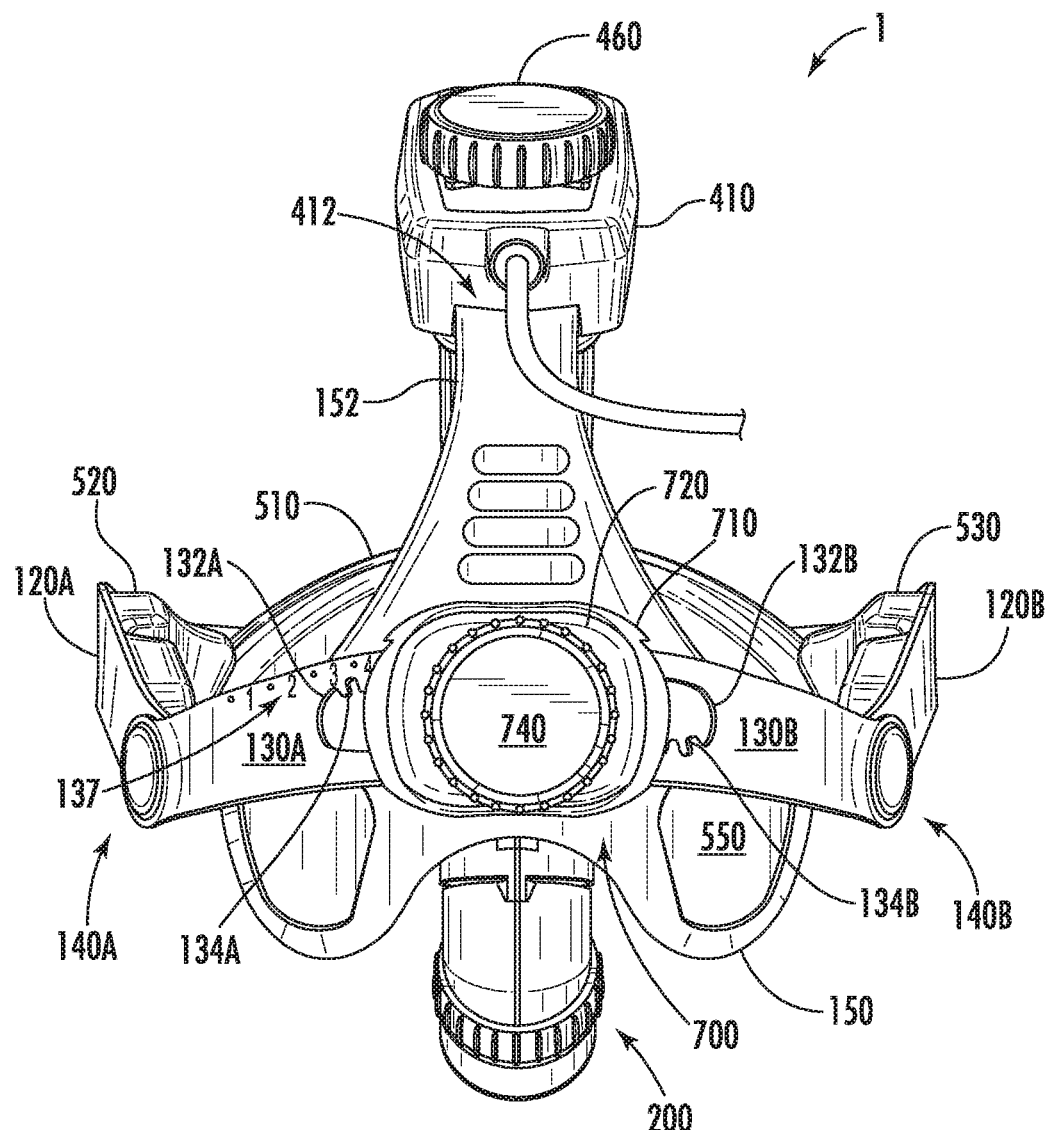
Figure 5:
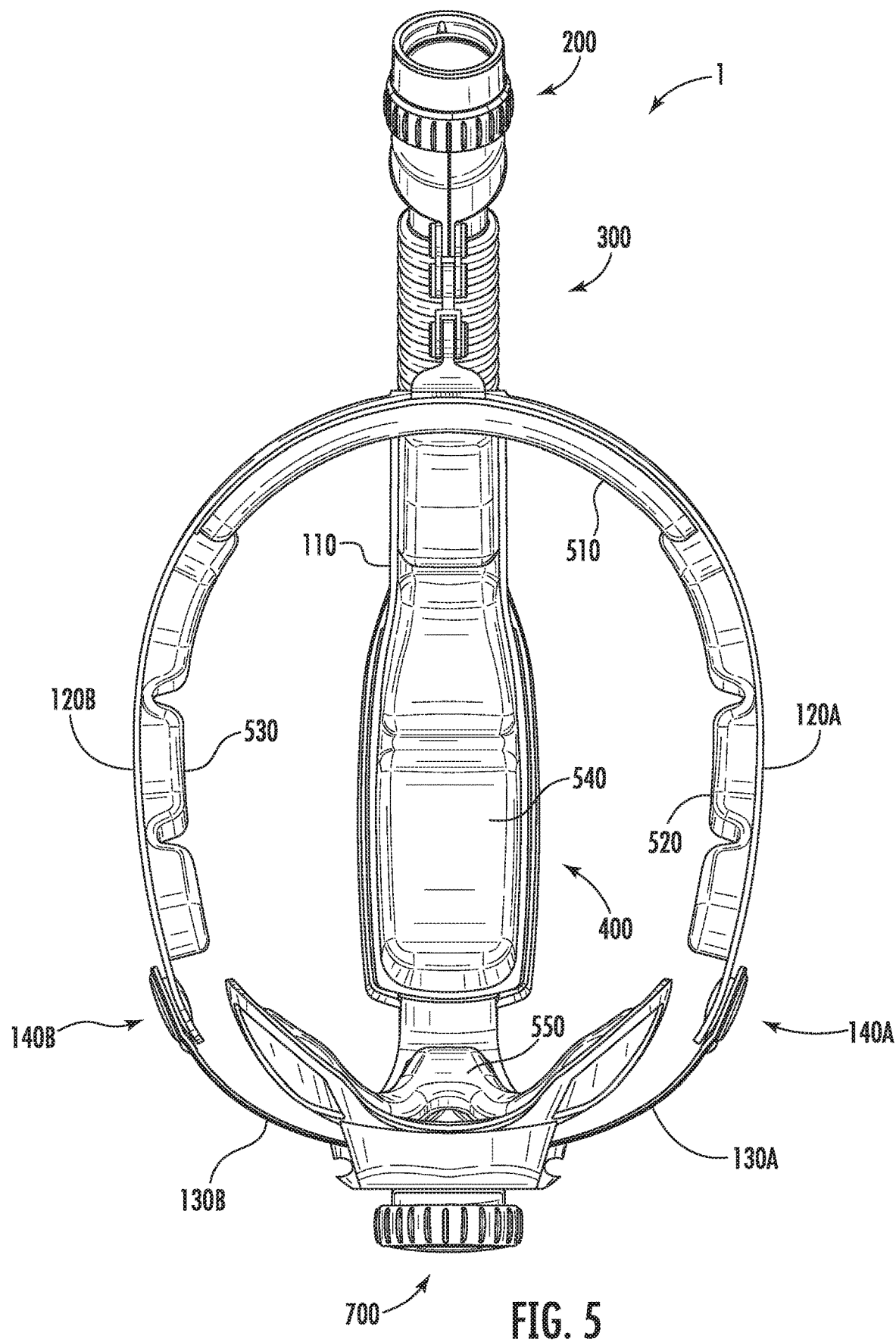
Figure 6:
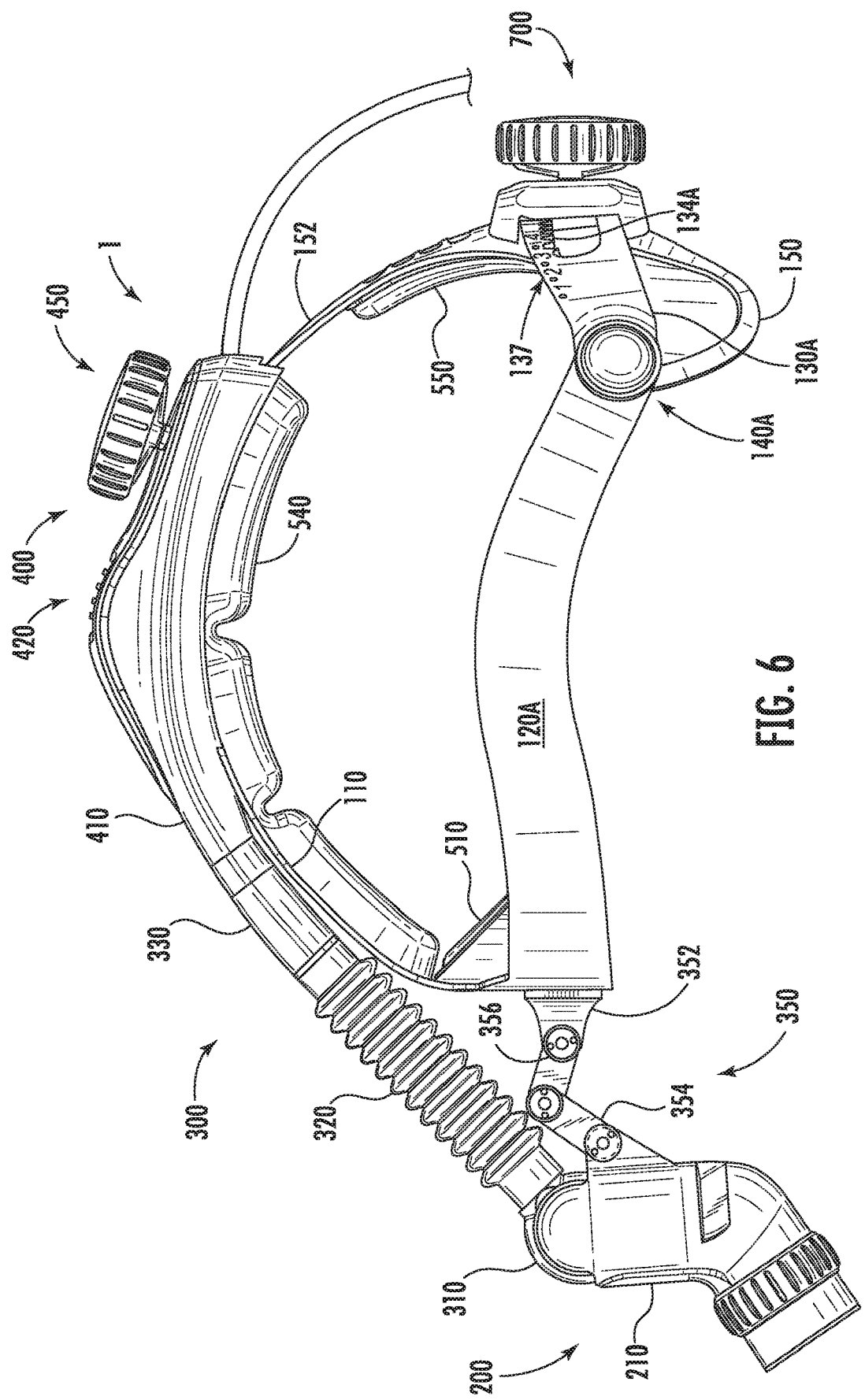
Figure 7:
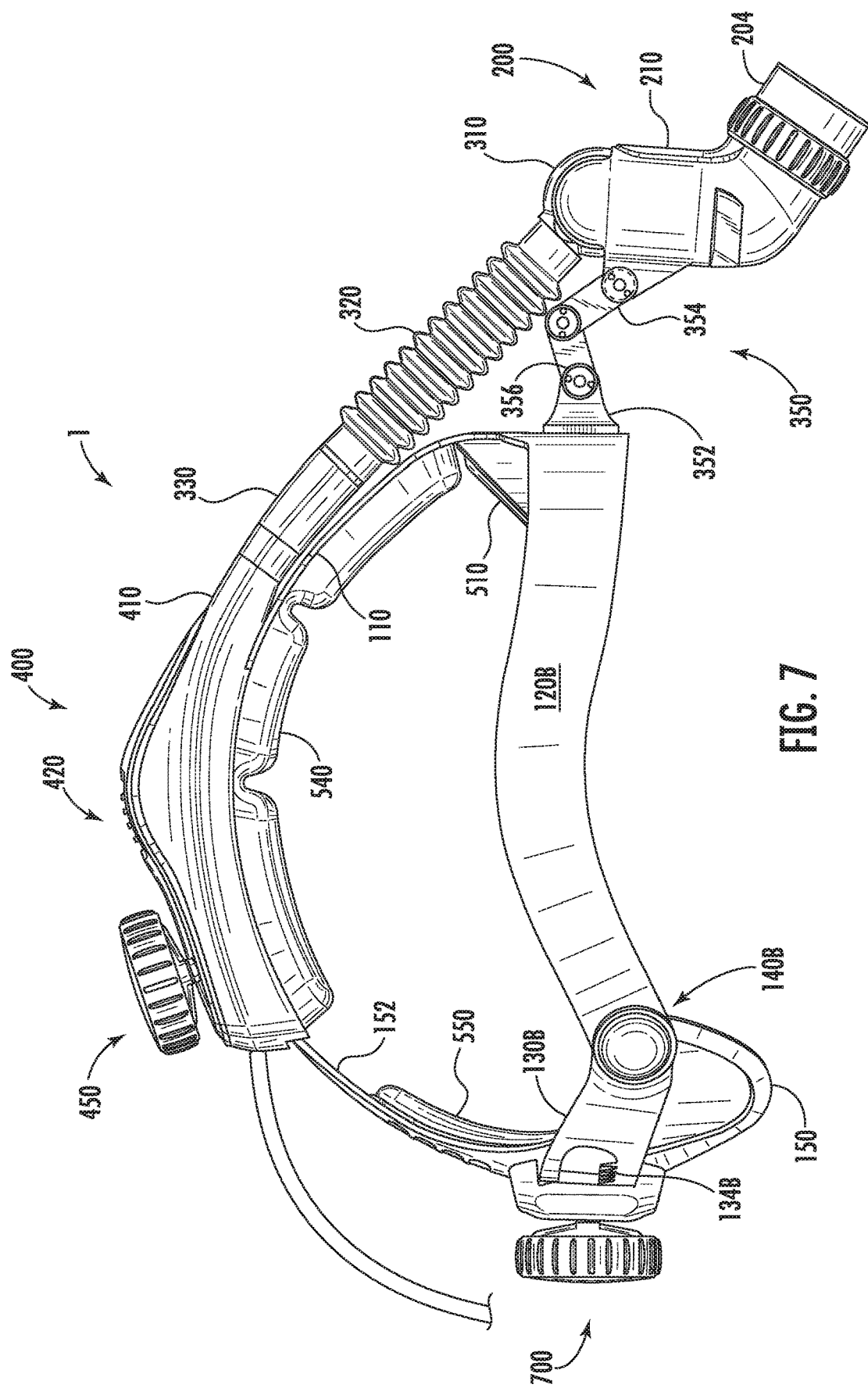

Unless otherwise defined, terms used herein should be construed to have the same meaning as commonly understood by one of ordinary skill in the art to which this subject matter belongs. It will be further understood that terms used herein should be interpreted as having a meaning that is consistent with the respective meaning in the context of this specification and the relevant art, and should not be interpreted in an idealized or overly formal sense unless expressly so defined herein.

Aspects of the subject matter are described herein with reference to sectional, perspective, elevation, and/or plan view illustrations that are schematic illustrations of idealized aspects of the subject matter. Variations from the shapes of the illustrations as a result, for example, of manufacturing techniques and/or tolerances, are to be expected, such that aspects of the subject matter should not be construed as limited to particular shapes illustrated herein. This subject matter can be embodied in different forms and should not be construed as limited to the specific aspects or embodiments set forth herein. In the drawings, the size and relative sizes of layers and regions can be exaggerated for clarity.

Unless the absence of one or more elements is specifically recited, the terms "comprising", "including", and "having" as used herein should be interpreted as open-ended terms that do not preclude the presence of one or more elements. Like numbers refer to like elements throughout this description.

It will be understood that when an element is referred to as being "on" another element, it can be directly on the other element or intervening elements can be present. Moreover, relative terms such as "on", "above", "upper", "top", "lower", or "bottom" are used herein to describe one structure's or portion's relationship to another structure or portion as illustrated in the figures. It will be understood that relative terms such as "on", "above", "upper", "top", "lower" or "bottom" are intended to encompass different orientations of the apparatus in addition to the orientation depicted in the figures. For example, if the apparatus in the figures is turned over, structure or portion described as "above" other structures or portions would now be oriented "below" the other structures or portions.

The term "substrate" or "submount" as used herein in connection with lighting apparatuses refers to a mounting member or element on which, in which, or over which, multiple solid state light emitters (e.g., LEDs) can be arranged, supported, and/or mounted. A substrate can be, e.g., a component substrate, a chip substrate (e.g., a LED substrate), or a sub-panel substrate. Example substrates useful with lighting apparatuses as described herein can, for example, comprise printed circuit boards (PCBs) and/or related components (e.g., including but not limited to metal core printed circuit boards (MCPCBs), flexible circuit boards, dielectric laminates, ceramic based substrates, and the like), ceramic boards having FR4 and/or electrical traces arranged on one or multiple surfaces thereof, high reflectivity ceramics (e.g., alumina) support panels, and/or mounting elements of various materials and conformations arranged to receive, support, and/or conduct electrical power to solid state emitters. Electrical traces described herein provide electrical power to the emitters for electrically activating and illuminating the emitters. Electrical traces may be visible and/or covered via a reflective covering, such as a solder mask material, Ag, or other suitable reflector.

Figure 8:
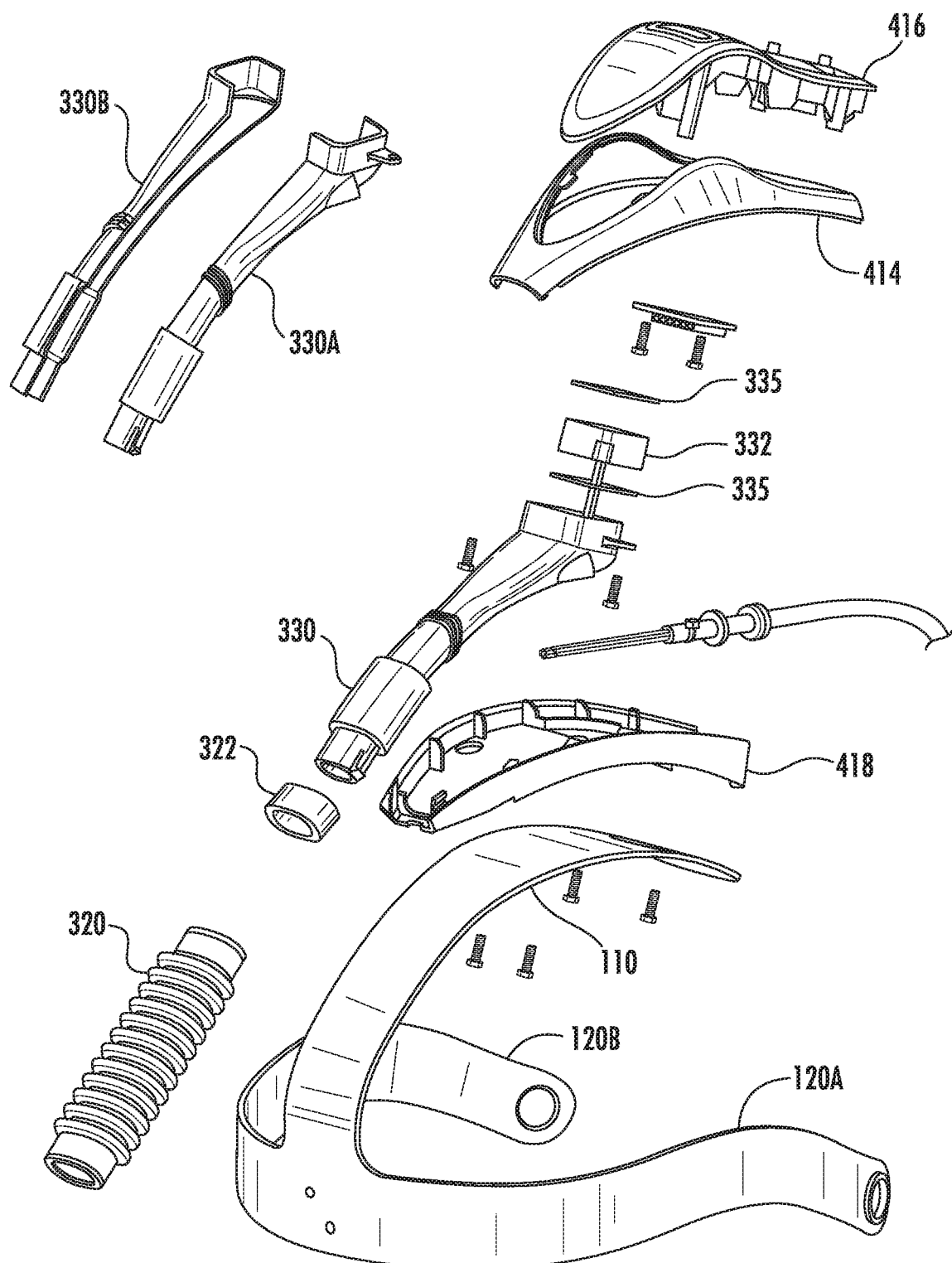
FIGS. 8 and 9A are partial exploded views of the head wearable device of FIGS. 1-7, in accordance with the disclosure herein.

FIGS. 1-7 show several perspective views of a head wearable device, generally designated 1. In the embodiment shown, the head wearable device 1 comprises an adjustable headpiece comprising a headband, generally designated 100, which has a top strap 110 and at least two lateral straps 120A/120B, and an occipital basket 150 attached to (e.g., removably, fixedly, and/or integrally) the headband 100; a luminaire, generally designated 200, movably attached at the front of the headband 100, a duct system, generally designated 300, to direct exhaust air from the luminaire 200 to a hot air exhaust 420 formed in the upper housing, generally designated 400, that is attached to the top strap 110 of the head wearable device 1; rear adjustment straps 130A/130B; a depth adjuster, generally designated 450, and a headband adjuster, generally designated 700, that are for adjusting the size of the headband 100 to the size of a wearer's head; a holster 600 with a battery pack and controller that is in electrical communication, via power cord 602, with the luminaire 200 and an air moving device (see 332, FIG. 8) associated with the duct system 300; and a padding system, generally designated 500, installed on at least some of the inner surfaces of the headband 100 and occipital basket 150. As shown, the lateral straps 120A/120B, together with the rear adjustment straps 130A/130B form a thin, flexible plastic ring of an approximately elliptical shape for fitting horizontally on the head of a wearer. The upper housing 400 can extend from the front to the rear (e.g., the occipital basket 150) of the headband 100, extend between the lateral straps 120A/120B of the headband 100, or extend between any two points on the ring. Two or more of these portions may form an integral piece, or operably or adjustably connected to each other. Headband may be constructed with more or fewer portions or straps than the embodiment shown and may take any shape. The headbands may cover more or less surface of the wearer's head than the embodiment as shown. While the headpiece is shown in this embodiment as comprising the headband 100 and the occipital basket 150, the headpiece may take any shape and may have a substantially continuous outer cover that is either adjustable to a wearer's head size or of fixed dimensions. Similarly, an outer shell may be provided around the headpiece, as needed based on the environment in which the head wearable device is to be worn.

Figure 9A:
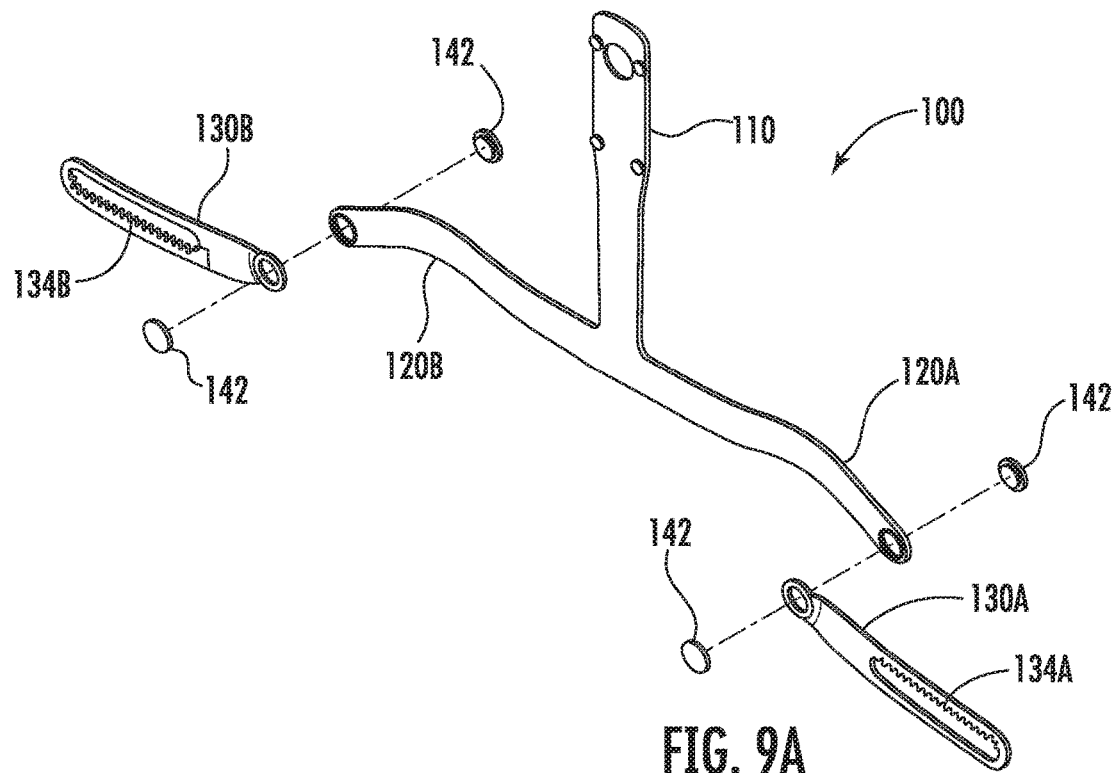
Figure 9B:
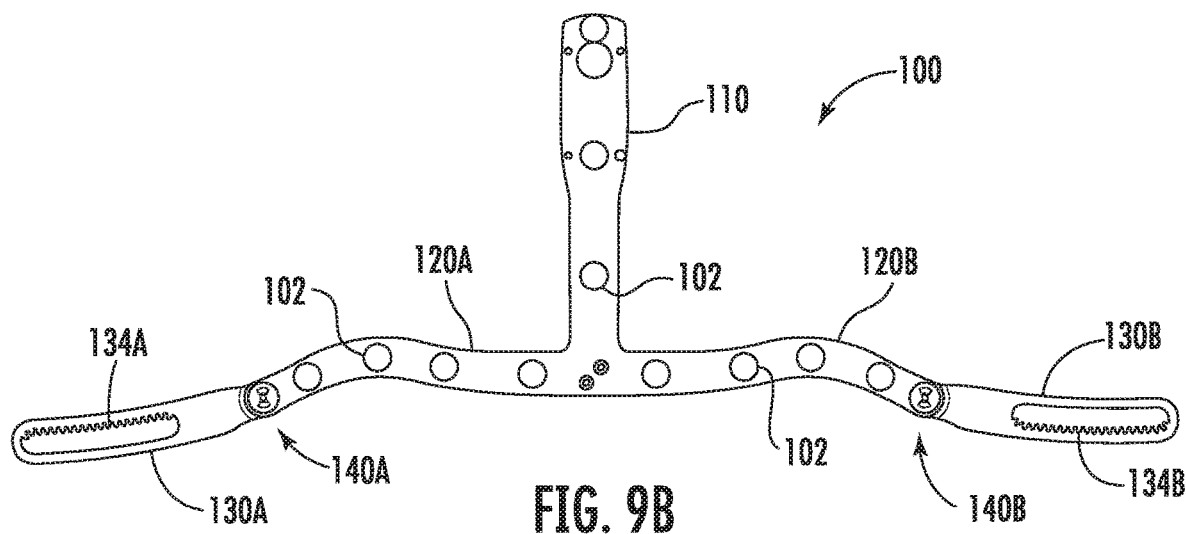
FIG. 9B is a partial rear assembly view of the front headstrap of the head wearable device of FIGS. 1-7, in accordance with the disclosure herein.
Figure 13:
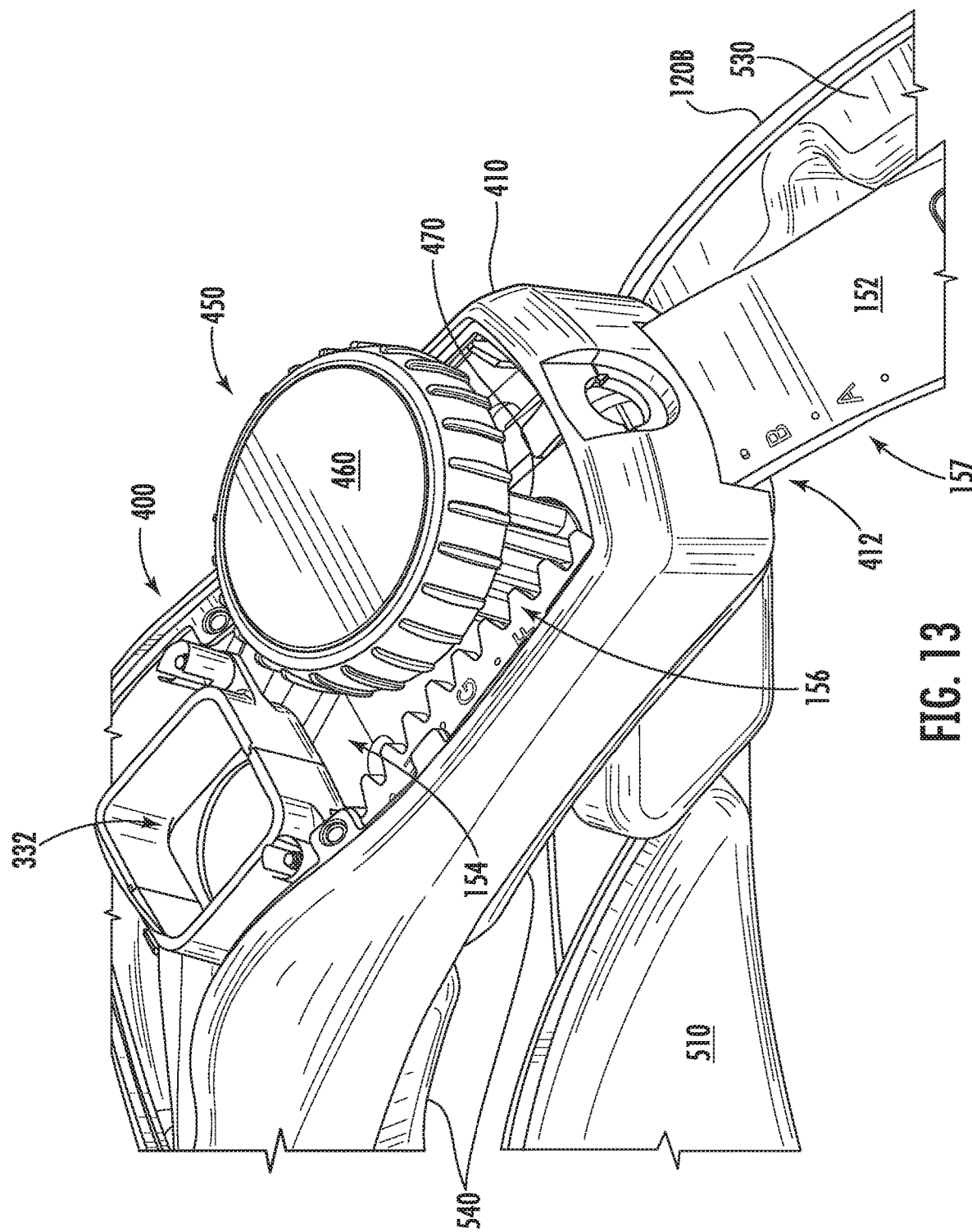
FIGS. 13-15 show internal views of one of the adjustment devices of the head wearable device of FIGS. 1-7, in accordance with the disclosure herein.
Figure 14:
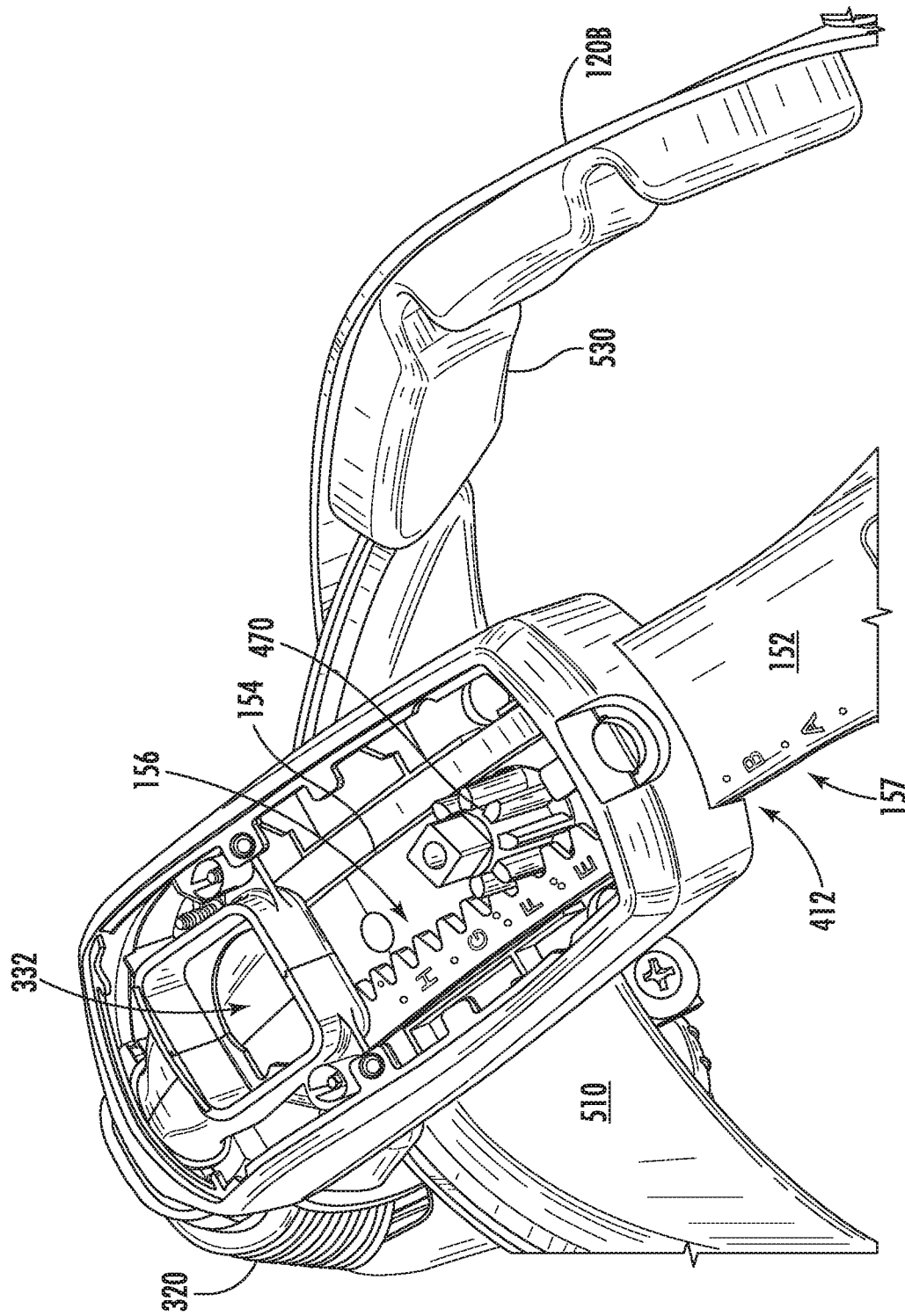
Figure 15:
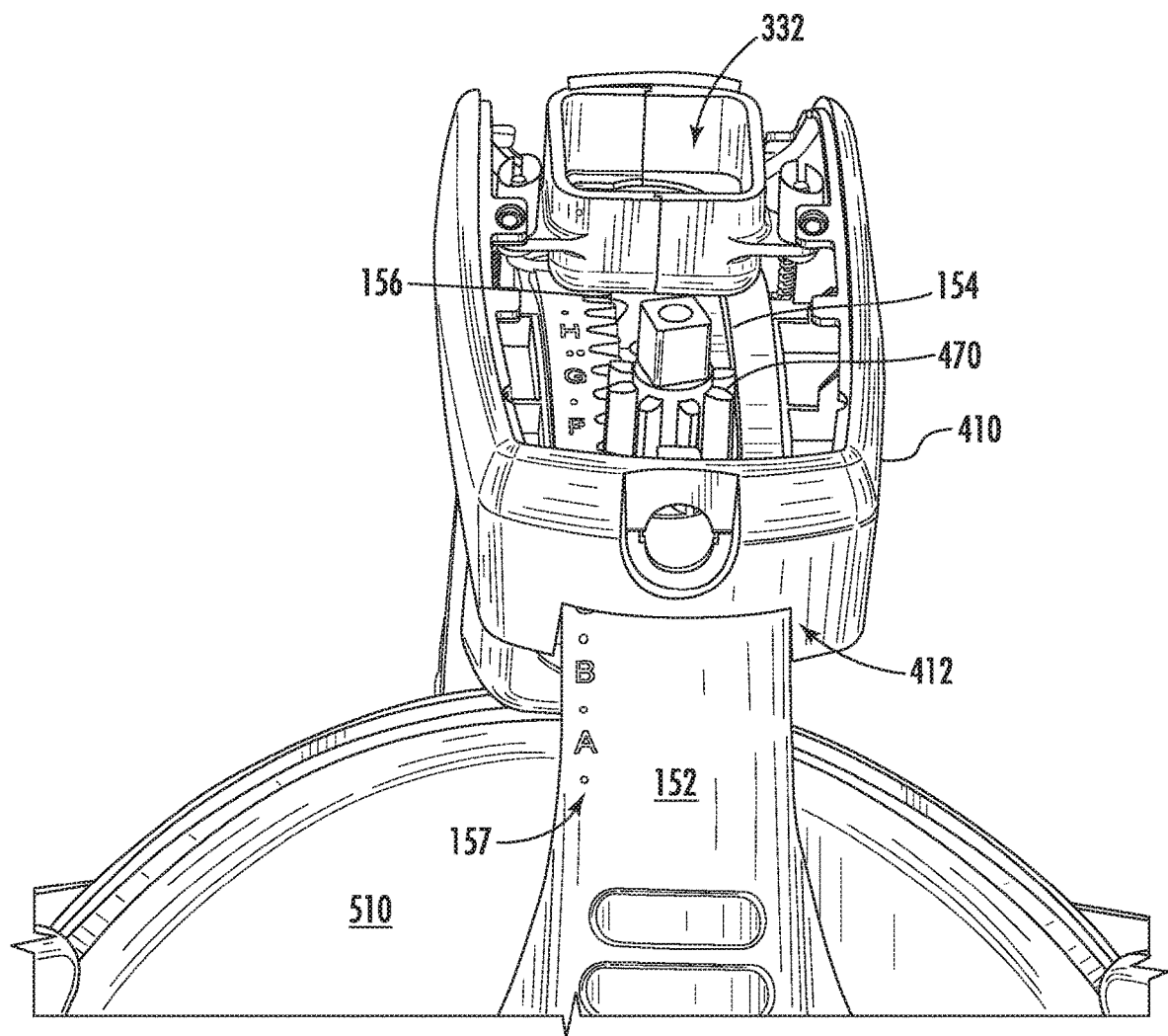

In the embodiment shown, the headband 100 comprising the top strap 110 and lateral straps 120A/120B is integrally formed from a single piece. An example of this portion of the headband 100 is shown in FIGS. 9A and 9B, with the top strap 110 and lateral straps 120A/120B being shown in a substantially planar (i.e., flat), unformed, configuration. The top strap 110 has upper housing 400 affixed thereto, into which the top strap 152 from the occipital basket 150 is inserted to connect the top strap 110 to the occipital basket 150. The upper housing 400 has an outer shell 410, which has a slot, generally designated 412, formed at a rear of the outer shell 410, into which slot 412 the strap 152 of the occipital basket 150 is inserted to adjust the depth of the head wearable device 1. The strap 152 of the occipital basket 150 has a slot (see 154, FIGS. 13-15) formed along the length thereof, the length of the slot 154 defining a maximum amount of adjustment of the depth of the head wearable device 1. As can be seen in greater detail in FIGS. 13-15, the slot 154 of the strap 152 has, on at least one side thereof, a plurality of teeth 156 that are configured to interface with, and be moved by, a gear 470 that is rotatably mounted within the upper housing 400 in the form of a rack-and-pinion arrangement. As such, a rotation of the top adjustment knob 460 and, accordingly, the top adjustment gear 470, causes the strap 152 of the occipital basket 150 to be lengthened or shortened relative to the upper housing 400 as the gear 470 draws the strap 152 into, or pushes the strap 152 out of, the upper housing 400. Due to the rack-and-pinion arrangement, precise size adjustments to the depth of the head wearable device 1 are contemplated. As such, a plurality of indexing marks, generally designated 157, are provided in an externally visible location on the strap 152 of the occipital basket 150 so that the depth of the head wearable device 1 may be easily and repeatably adjusted to a given value for a plurality of wearers of the head wearable device 1.

The headband 100 is further connected to the occipital basket 150 by lateral extension straps 130A/130B, which are rotatably coupled to the lateral straps 120A/120B, respectively, at respective hinges, generally designated 140A/140B, which in this embodiment are circular hinges. Each of the lateral extension straps 130A/130B wraps behind the occipital basket 150 and is inserted within a housing of the headband adjuster, generally designated 700, which is shown on the rear external surface of the occipital basket 150. As can be seen in FIGS. 9A and 9B, the lateral extension straps 130A/130B have a slot 132A/132B formed along the length thereof, respectively, the length of the slot 132A/132B defining a maximum amount of adjustment of the circumference of the head wearable device 1. The slot 132A/132B of each lateral extension strap 130A/130B has, on at least one side thereof, a plurality of teeth 134A/134B that are configured to interface with, and be moved by, a gear (see 730, FIG. 19) that is rotatably mounted within the housing of the headband adjuster 700 in the form of a rack-and-pinion arrangement. The plurality of teeth 134A on a first of the lateral extension straps 130A are on an opposite side of the slot 132A from the plurality of teeth 134B formed in the slot 132B of the second lateral extension strap 130B, such that a rotating motion of the occipital basket adjustment gear 730 causes a simultaneous expansion or contraction, depending on the direction in which the knob 740 is rotated, of the headband 100 to correspondingly increase or decrease lateral circumference of the head wearable device 1. Due to the rack-and-pinion arrangement, precise size adjustments of the head wearable device 1 are contemplated. As such, a plurality of indexing marks, generally designated 137, are provided in an externally visible location on one or more of the lateral extension straps 130A/130B so that the head wearable device 1 may be easily and repeatably adjusted to a given size for a plurality of wearers of the head wearable device 1. The slots 132A/132B are shown as being closed at both ends thereof to prevent the lateral extension straps 130A/130B from becoming disengaged from the headband adjuster 700. As such, the lateral extension straps 130A/130B are captively held within the headband adjuster 700 when worn by a wearer.

The hinges 140A/140B connecting the lateral straps 120A/120B of the headband 100 to the lateral extension straps 130A/130B are configured to pivot about an axis defined through the center of each respective hinge 140A/140B. Any type of hinge may be used and, in fact, the lateral extension straps 130A/130B may be integrally formed with the lateral straps 120A/120B of the headband 100. However, it is advantageous to use the circular hinges 140A/140B shown because, as the strap 152 is drawn into or pushed out from the upper housing 400 on the headband 100 to alter a depth of the head wearable device 1, the position of the occipital basket 150 changes at least vertically, relative to the lateral straps 120A/120B, such that the angle between the lateral straps 120A/120B and the lateral extension straps lateral extension straps 130A/130B at the hinges 140A/140B can be altered without deforming the lateral extension straps 130A/130B that might cause any distortions or deformations thereof in the region of the slots 132A/132B, thereby preventing binding of the lateral extension straps 130A/130B within the housing of the headband adjuster 700.

A padding system 500 is attached to the inner surfaces of the head wearable device 1, including the inner surfaces of the headband 100 and the occipital basket 150 where contact would otherwise occur with the head of a wearer of the head wearable device 1. While any suitable type and configuration of padding may be utilized for the padding system 500, the embodiment shown has padding segments that are attached to the inner surfaces of the headband 100 and the occipital basket 150. The padding segments may be formed from any suitable material having a suitable degree of padding to provide a desired amount of comfort for a wearer during extended wearing times (e.g., on the order of multiple hours). The padding system comprises a rear pad 550, side pads 520/530, and a top pad 540 attached to the corresponding inner surfaces of the occipital basket 150, the lateral straps 120A/120B, and the top strap 110 of the head wearable device 1, respectively. The padding system 500 may further comprise a brow pad 510 attached to the inner surface of the headband at or about an intersection of the top strap 110 and the lateral straps 120A/120B. Each of the padding segments 510, 520, 530, 540, and 550 described herein can be portions of a large integral pad and do not need to be separate pads.

The padding segments 510, 520, 530, 540, and 550 are attached to the headband 100 or the occipital basket 150, respectively, by any suitable attachment type, including, for example, adhesive, interlocking snaps, mechanical interlocking tabs, and the like. The padding segments 510, 520, 530, 540, and 550 may be contoured to the shape of the respective strap or occipital basket 150 to which the padding segment 510, 520, 530, 540, and 550 is attached and may have a size less than or greater than a width of the strap(s) to which each such padding segment 510, 520, 530, 540, and 550 is attached. As such, a brow pad is provided at the front of the headband 100 at a position that would be against the forehead of a wearer of the head wearable device 1. This brow pad 510 may extend, at least to some extent, onto the top strap 110 and the two lateral straps 120A/120B. In the embodiment shown, the strap 152 of the occipital basket 150 and the lateral extension straps 130A/130B are devoid of padding segments, not only because these portions are spaced apart from the surface of the wearer's head while being worn, but also so that mechanical interference does not occur between adjacent components as the dimensions (e.g., the depth and/or the circumference) of the head wearable device 1 is adjusted. In the embodiment shown, the padding segments 510, 520, 530, 540, and 550 can be removable for cleaning, maintenance, etc. One or more of the padding segments 510, 520, 530, 540, and 550 can have a different degree of softness from others of the padding segments 510, 520, 530, 540, and 550. One or more (e.g., each, or all) padding segments 510, 520, 530, 540, and 550 may have more than two layers of cushioning material.

Referring to FIGS. 20-26, according to some embodiments of the present disclosure, the rear pad 550 comprises a first layer 570 of a first cushioning material having a first durometer, and a second layer 580 of a second cushioning material having a second durometer that is harder than the first durometer. In an example embodiment, the first cushioning material is silicone foam, and the second cushioning material is also silicone foam, but the silicone foam in the second layer 580 has a higher durometer than the silicone foam in the first layer 570. For example, the durometer of the second layer 580 can be 5%, 10%, 25%, or up to and including 50% higher than the durometer of the first layer 570. In other words, the silicone foam in the second layer 580 is harder (e.g., less compliant) than the silicone foam in the first layer 570. The second layer 580 of the second cushioning material is closer than the first layer 570 of the first cushioning material to the inner surface of the occipital basket 150. The harder second layer 580 provides support, while the softer, conforming first layer 570 is in closer contact with the wearer and provides increased comfort to the wearer of the head wearable device 1.

Figure 21:
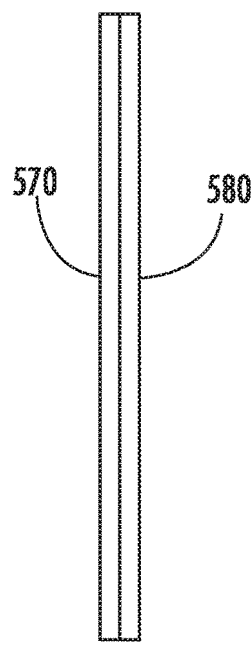
FIG. 21 is a side view of an example embodiment of the cushioning materials in the rear pad of FIG. 20, in accordance with the disclosure herein.

Although FIG. 21 shows that the first layer 570 and the second layer 580 of the respective cushioning materials have the same or similar thickness, it is contemplated that the first layer 570 can have a different thickness from the second layer 580. The thickness of each layer is preferably no more than 1 inch (in.) and, more preferably, no more than 0.5 in., for example, about 0.25 in. In an example embodiment, the first layer 570, which is oriented towards (e.g., adjacent the head of) the wearer, is ¼" die-cut silicone foam (for example, BISCO® BF-2000, an ultra soft silicone foam manufactured by Rogers Corporation) and the second layer 580, which is oriented towards (e.g., adjacent the surface of) the occipital basket 150 is ¼" die-cut silicone foam (for example, BISCO® HT-800, a medium cellular silicone foam manufactured by Rogers Corporation), which can be either open cell silicone foam or closed cell silicone foam. In some aspects, the respective durometers of the silicone foam layers can be defined by compression force deflection of the foam silicone. In some embodiments, the durometer is within a range of about (e.g., ±1%, ±2%, ±5%, ±10%, ±25%, or ±50%) 10-70 Shore A, inclusive. HT-800 silicone foam has a density, as measured according to ASTM D 1056, of 22 pounds per cubic feet (lb/ft$^3$). BF-2000 silicone foam has a density, as measured according to ASTM D 1056, of 10 lb/ft$^3$. For the first layer 570, the die-cut silicone foam (BF 2000) can have a compression force deflection of about (e.g., ±1%, ±2%, ±5%, ±10%, ±25%, or ±50%) 1.5 pounds per square inch (psi). The compression force deflection is a measure of the load bearing ability of a foam material and is the force exerted against a flat compression foot that is larger than the specimen to be tested. The term compression force deflection is also sometimes referred to as "compression load deflection". The compression force deflection metric is measured as the force necessary to achieve a 25% deflection according to ASTM D 1056. For the second layer 580, the die-cut silicone foam (for example, BISCO® HT-800) can have a compression force deflection of within a range including, for example, about (e.g., ±1%, ±2%, ±5%, ±10%, ±25%, or ±50%) 6-14 psi. In some embodiments, the second layer 580 of the second cushioning material 582 has more open space on its upper or lower surface due to perforations than the first layer 570 of the first cushioning material 572, which has, in the embodiment shown, a surface area of about 10.617 square inches (in$^2$). In another aspect, the total surface area of the cavities formed by the perforations 584 in the second layer 580 of the second cushioning material 582 is higher than the total surface area of the cavities formed by the perforations 574 in the first layer 570 of the first cushioning material 572, for example, the total surface area of the cavities in the second layer 580 is about 9.249 in$^2$.

In some embodiments, the perforation patterns can be chosen taking into consideration the durometer (e.g., hardness) and density of each layer specific to the cushioning material used. The perforations in the layers of cushioning material also improve heat dissipation and air-flow. For the rear pad 550, the volume of the first cushioning material 572 removed from the first layer 570 in forming the plurality of perforations 574 is about 1.575 cubic inches (in$^3$) and the volume of the second cushioning material 582 removed from the second layer 580 in forming the plurality of perforations 584 is about 5.112 in$^3$.

Figure 22:
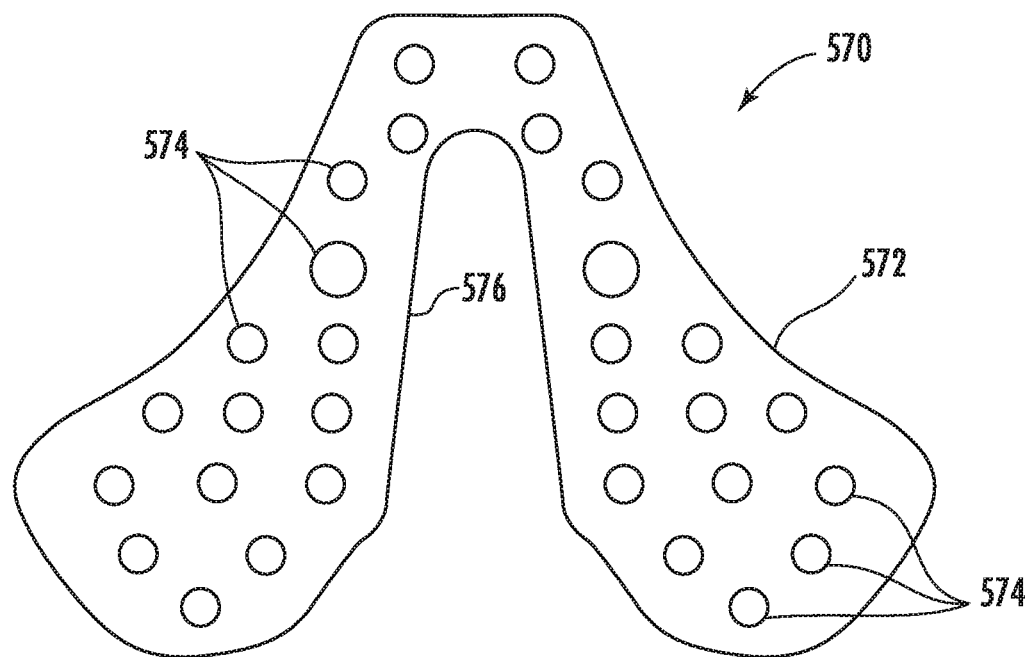
FIG. 22 is a plan view of an example embodiment of the first layer of the first cushioning material in the rear pad shown in FIGS. 20 and 21, in accordance with the disclosure herein.
Figure 23:
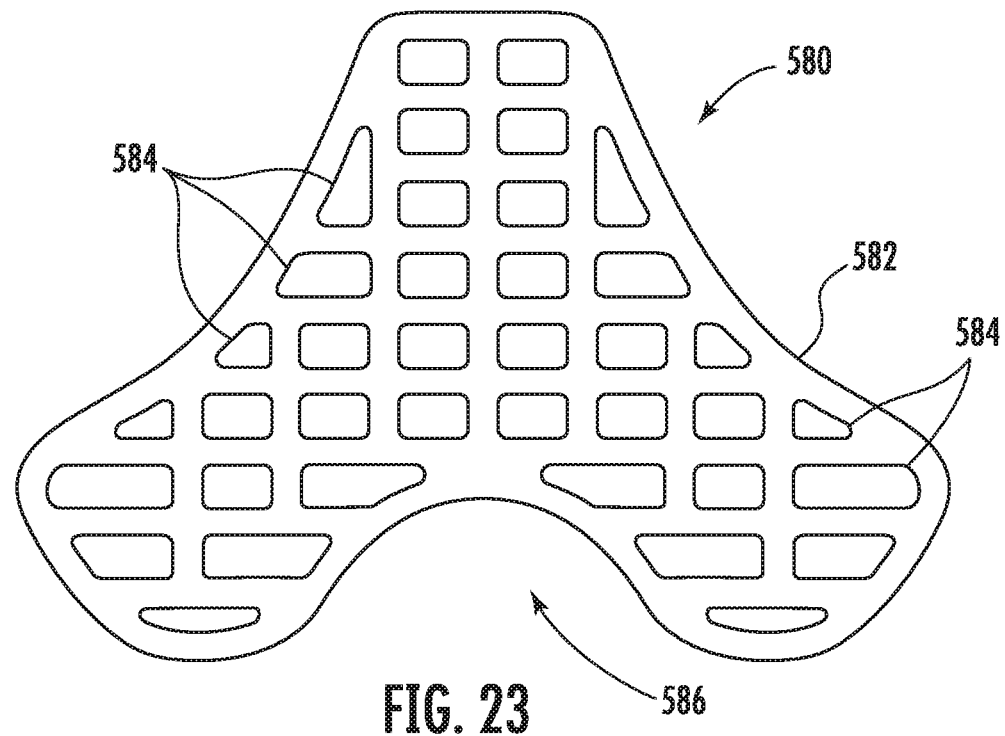
FIG. 23 is a plan view of an example embodiment of the second layer of the second cushioning material in the rear pad shown in FIGS. 20 and 21, in accordance with the disclosure herein.

According to further embodiments of the present subject matter, the first layer 570 of the first cushioning material 572 and the second layer 580 of the second cushioning material 582 are each perforated. As shown in FIG. 22, the first layer 570 has a first perforation pattern comprising a plurality of first perforations 574 formed therein. FIG. 23 shows the second layer 580, which has a second perforation pattern comprising a plurality of second perforations 584. The first perforation pattern and the first perforations 574 differ from the second perforation pattern and the second perforations 584. The first perforations 574 in the first layer 570 are generally arranged in a first perforation shape and the second perforations 584 in the second layer 580 are generally in a second perforation shape, which may differ from the first perforation shape. For example, the first perforations 574, or at least the majority of the first perforations 574, in the first layer 570 of the first cushioning material 572, are generally circular, and the second perforations 584, or at least the majority of the second perforations 584, in the second layer 580 of the second cushioning material 582 are in a shape other than circular, such as generally square, rectangular, and/or triangular, or generally in a grid-like pattern. The first and second perforations 574/584 are holes or apertures that pass through the thickness of the respective first and second cushioning materials 572/582. The first and second perforations 574/584 can be created by die-cutting, piercing, boring, or any other conventional methods.

A different perforation pattern can be a result of a higher perforation count of the perforation of the same shape, or perforations of a different shape or different shapes, or a combination of the foregoing. In an aspect of the present disclosure shown in FIG. 23, the second layer 580 of the second cushioning material 582 has more open space on its upper or lower surface due to second perforations 584 than the first layer 570 of the first cushioning material 572. In another aspect of the present disclosure, the total volume of the cavities formed by the second perforations 584 in the second layer 580 of the second cushioning material 582 is higher than the total volume of the cavities formed by the first perforations 574 in the first layer 570 of first cushioning material 572. The second layer 580 has a cut-out recess, generally designated 586, which substantially defines the size, shape, and/or contour of the cut-out recessed region 556 of the rear pad 550, the cut-out recess 586 and the cut-out recessed region 556 having a size, shape, and/or contour that corresponds to the size, shape, and/or contour of the cut-out 158 of the occipital basket 150.

In additional embodiments of the present subject matter, the rear pad 550 has an inner surface in contact with a wearer and an outer surface attached to the inner surface of the rear portion of the headband, and the rear pad 550 comprises a recess 576 formed in the first layer 570.

In each of the respective padding segments 510, 520, 530, 540, and 550, the cushioning material may be any suitable synthetic foam such as silicone foam, expanded polystyrene, polyurethane, or other types of polymer. In an example embodiment of the present disclosure, the cushioning material in both layers are a silicone foam, for example, the silicon foam materials commercially available at Stockwell Elastomerics, Inc. The differences in the first and second layers 570/580 include the durometer of the first and second cushioning materials 572/582. Any suitable material may be used as long as the material has a similar durometer as the materials specified herein.

Figure 20:
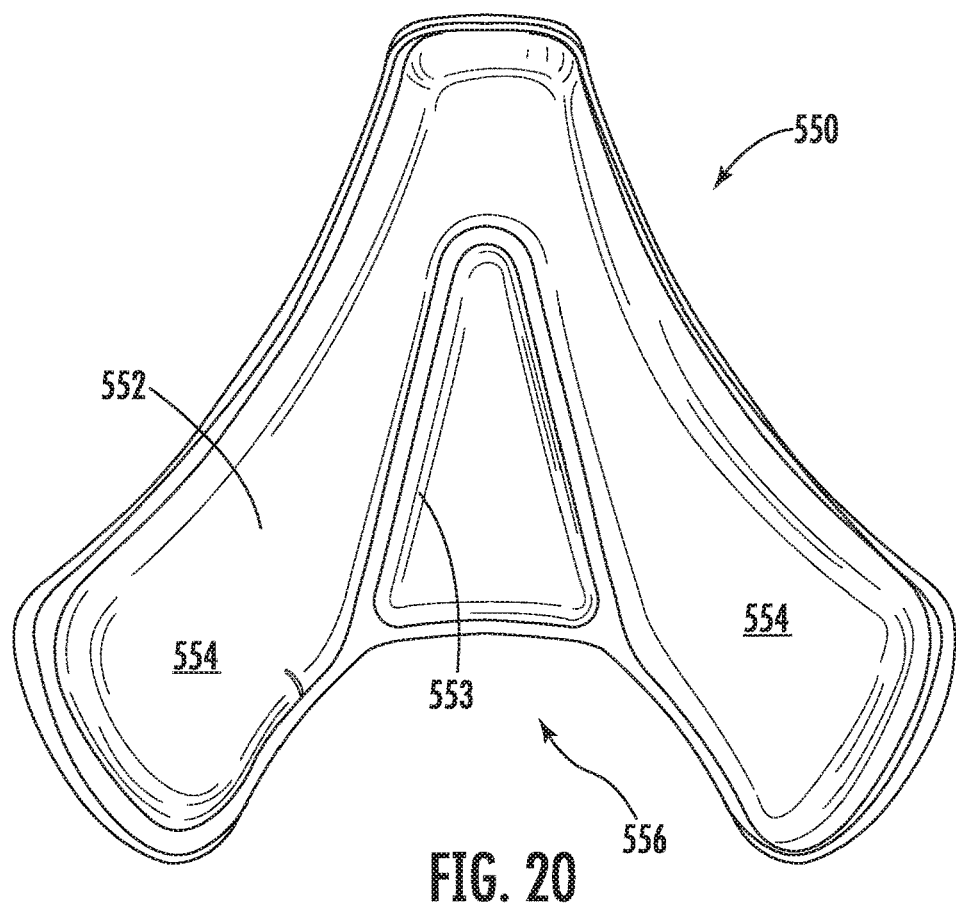
FIG. 20 is an exterior view of a rear pad of the padding system shown in the head wearable device of FIGS. 1-7, in accordance with the disclosure herein.
Figure 24:
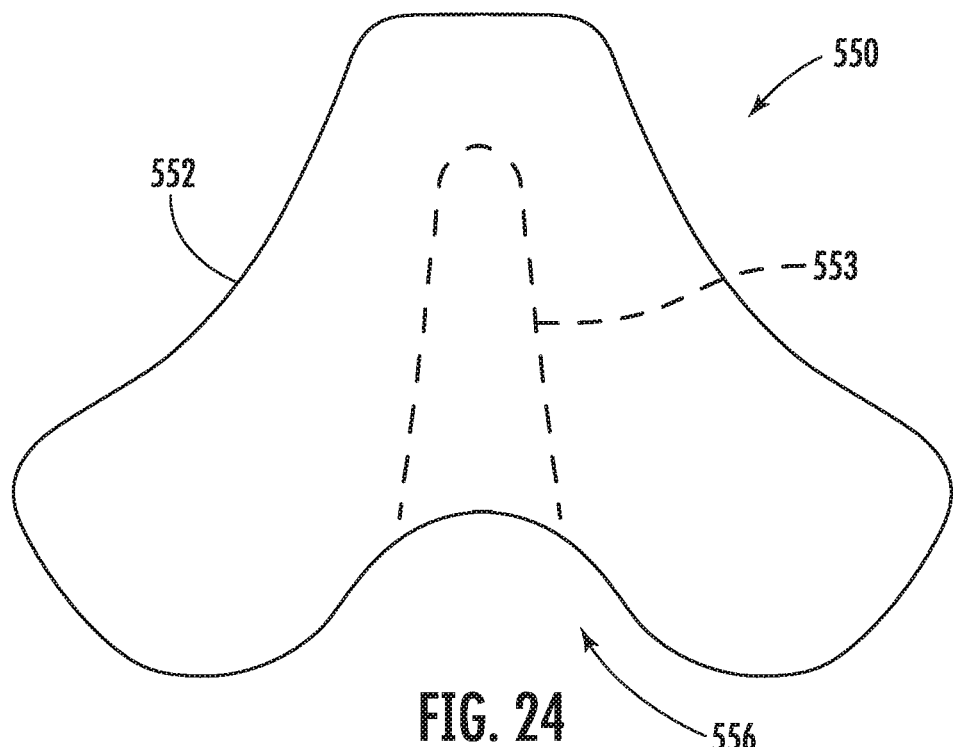
FIG. 24 is a plan front view of a rear pad cover for the rear pad shown in FIGS. 20 and 21, in accordance with the disclosure herein.
Figure 25:
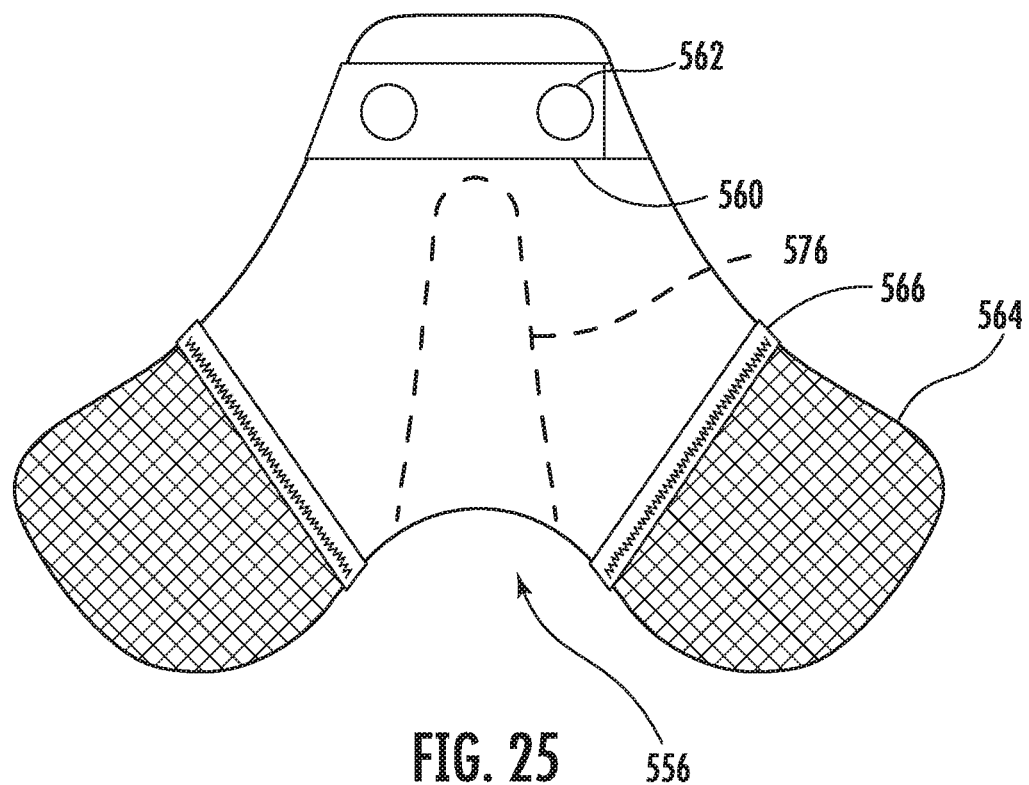
FIG. 25 is a plan rear view of the rear pad cover shown in FIG. 24, in accordance with the disclosure herein.
Figure 26:
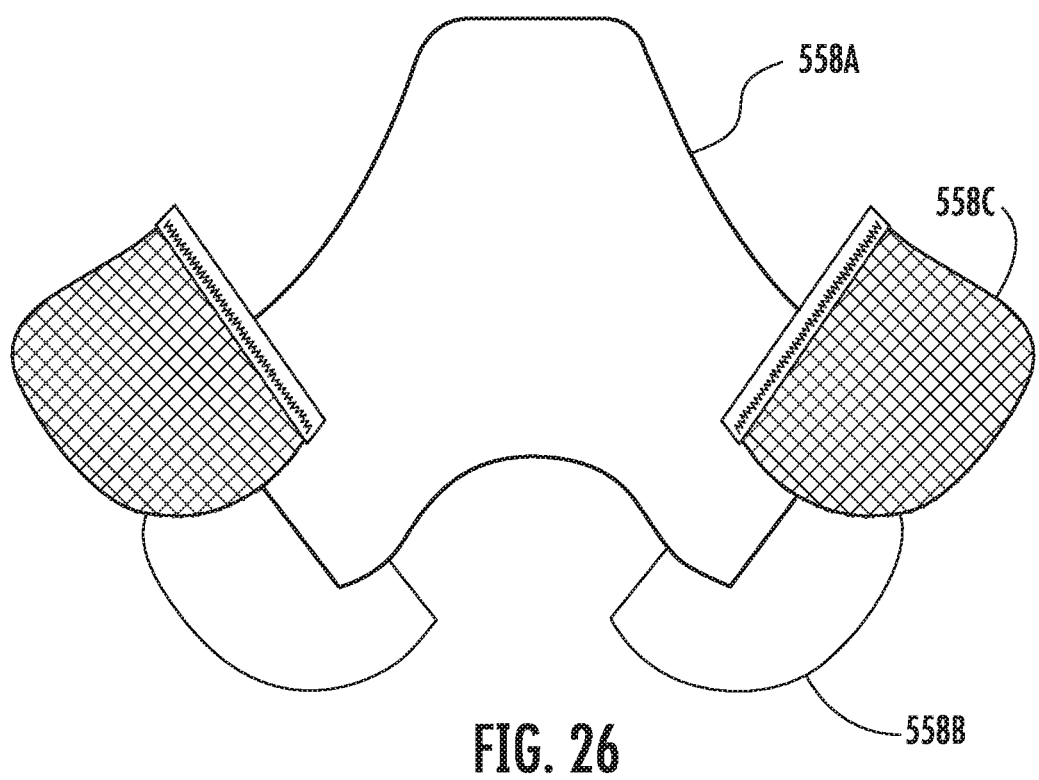
FIG. 26 is an assembly view of the panels of the rear pad cover shown in FIGS. 24 and 25, in accordance with the disclosure herein.

As shown in FIGS. 24-26, the rear pad 550 is covered by a rear pad cover 552, which can be made of fabric, synthetic polymers, or other suitable materials, such as polyethylene, nylon, glass fibers and the like. The rear pad 550 comprises a recessed area 553 formed therein, between the opposing padding lobes 554 that have, in the embodiment shown, a generally triangular shape. The recessed area 553 is provided to relieve pressure from the occipital basket 150 being secured over the rear portion of the head of a wearer, thereby accommodating accessories worn by the wearer, such as, for example, straps for the cap, loupe, or glasses and the like, without interfering with the head wearable device 1 being sufficiently secured over the wearer's head and to avoid pressure that may push against the back of the wearer's head. Any shape for the rear pad 550 is contemplated and, furthermore, the recessed area 553 can be in any shape, including, as shown in FIG. 20, a generally triangular shape. Recessed area 553 can have a reduced thickness compared to the thickness of the rear pad 550 overall and/or to the padding lobes 554. In the example embodiment shown, the rear pad cover 552 is able to sufficiently surround a rear pad 550 having a total volume of about 7.18 in$^3$. In an example embodiment, the rear pad cover 552 is made of Darlington 96630 fabric manufactured by Darlington. The Darlington 96630 material used in the example embodiment is a 4-way stretch heavy weight tricot, 356 gsm (grams per square meter) weight, and is available in various colors. As shown in FIG. 26, the back of rear pad cover 552 shown in FIG. 25 may be produced by layering a main body piece 558A, two inner overlap pieces 558B and two netting pieces 558C in the order as illustrated, such that the back of the rear pad cover 552 has an elastic netting pocket 564 on the outer surface of each side flap. The rear pad cover 552 comprises a cut-out recessed region 556 contoured to the shape of the occipital basket 150 and also covers the recess 576. Regardless of the materials specified herein, it is contemplated that at least a portion of the rear pad cover 552 may be made from a breathable stretch material with an estimated weight within the range of about 300-400 gsm inclusive.

The front of the rear pad cover 552 can be fabric such as Darlington fabrics, 4-way stretch spandex, while the back of the rear pad cover 552 can be nylon/UBL (unbroken loop) fabric 560, which is a part of a hook-and-loop fastening system, with optional snaps 562 provided to more securely attach the rear pad cover 552 over the rear pad 550. Other materials are suitable for use in the padding system 500, and can be selected depending on cleaning and comfort requirements.

The rear pad 550 can be assembled by aligning the front of rear pad cover 552 shown in FIG. 24, the first layer 570 of the first cushioning material shown in FIG. 22, the second layer 580 of the second cushioning material shown in FIG. 23, and the back of the rear pad cover 552 shown in FIG. 25, and then sewing along the periphery of the covers. The stretch-mesh netting pockets 564 on the back of the rear pad cover 552 is made of an elastic material, such as spandex mesh, and is removably disposed about the outer surface of the corresponding side flaps of the occipital basket 150 to help secure the rear pad cover 552 to the occipital basket 150. The recess in the rear pad 550 can be formed by adding stitches along the corresponding recess 576 in the first layer 570 of the first cushioning material in the rear pad 550.

Figure 27:
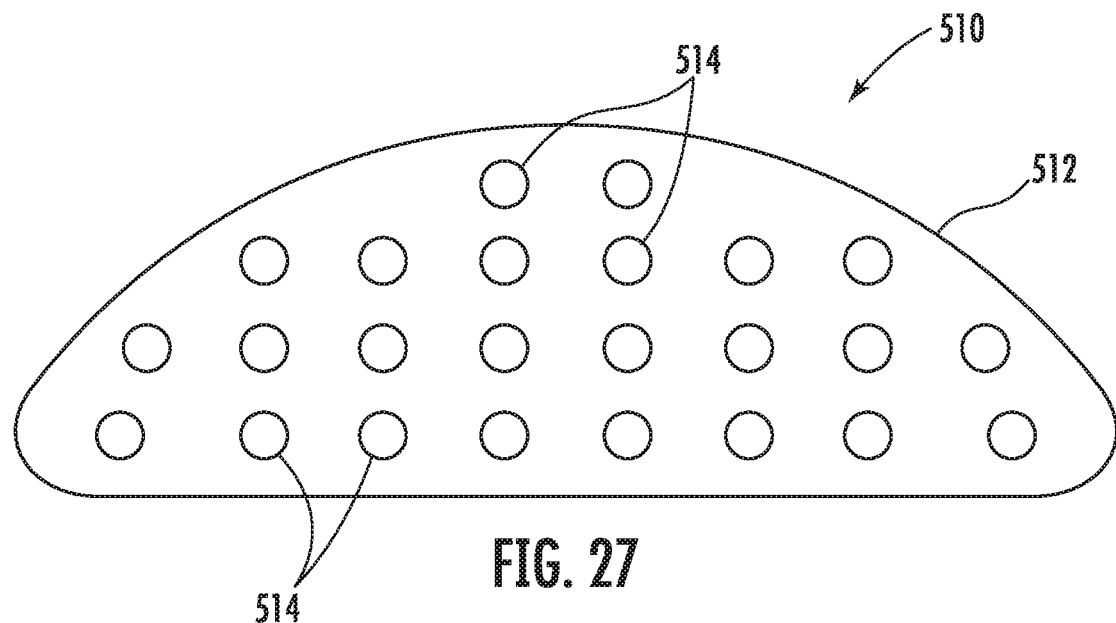
FIG. 27 is a plan view of an example embodiment of a first layer of a first cushioning material of a front pad of the head wearable device shown in FIGS. 1-7, in accordance with the disclosure herein.
Figure 28:
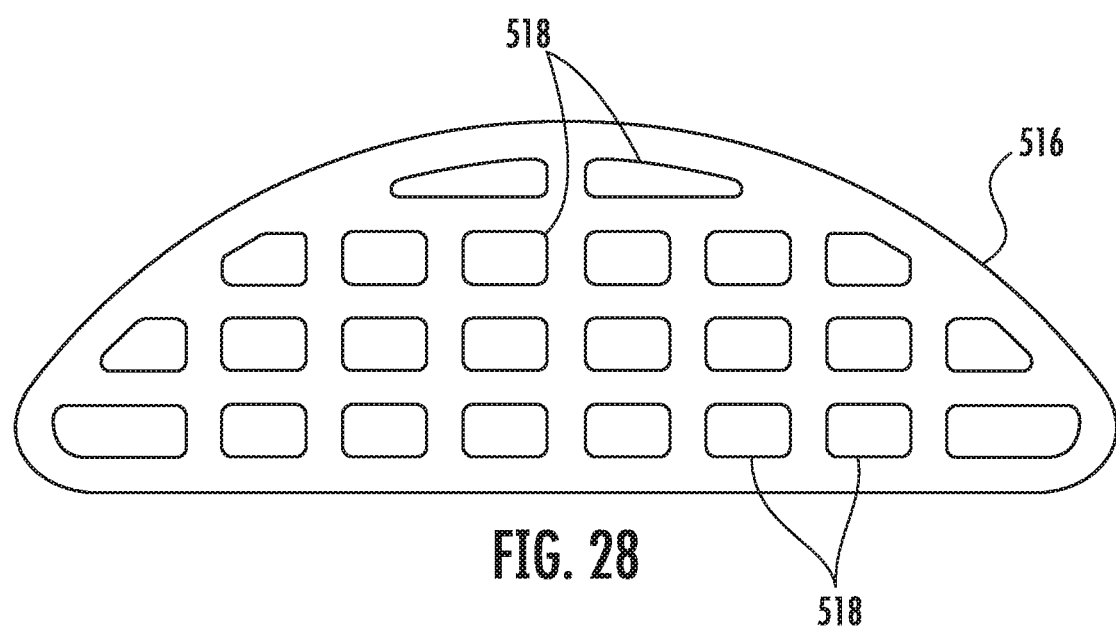
FIG. 28 is a plan view of an example embodiment of a second layer of a second cushioning material in a front pad of the head wearable device shown in FIGS. 1-7, in accordance with the disclosure herein.

Referring to FIGS. 27 and 28, the brow pad 510 comprises a first layer 512 of a first cushioning material having a first durometer, and a second layer 516 of a second cushioning material having a second durometer that is different (e.g., harder) than the first durometer. The first layer 512 is perforated in a first perforation pattern, comprising first perforations 514, and the second layer 516 is perforated in a second perforation pattern, comprising second perforations 518, which differ from the first perforation pattern. In an example embodiment, the first layer 512 of the first cushioning material of the brow pad 510 is configured as a comfort layer arranged adjacent the head of the wearer and is formed from ¼" die-cut silicone foam (BF 2000), while the second layer 516 of the second cushioning material is spaced apart from the head of the wearer and is formed ¼" die-cut silicone foam (for example, BISCO® HT-800).

Although the example embodiments of rear pad 550 and brow pad 510 both include a softer, inner, first layer of cushioning material and a harder, outer, second layer of cushioning material, other layering options are contemplated, depending on the cleanability and comfort standards and the desired fit, feel, and comfort level. In some embodiments, the BISCO® silicone foams disclosed herein can be described as being a range of materials, including extra firm (HT-840), firm (HT-820), medium (HT-800), soft (HT-870), extra soft (BF-1000), and ultra soft (BF-2000). HT-840 has a compression force deflection within a range of 16-26 psi and, preferably, a compression force deflection of 22 psi. HT-820 has a compression force deflection range of 12-20 psi and, preferably, a compression force deflection of 16 psi. HT-800 has a compression force deflection within a range of 6-14 psi and, preferably, a compression force deflection of 9 psi. HT-870 has a compression force deflection within a range of 2-7 psi and, preferably, a compression force deflection of 4 psi. BF-1000 has a compression force deflection within a range of 1-5 psi and, preferably, a compression force deflection of 3 psi. BF-2000 has a compression force deflection of about 1.5 psi. Some other possible combinations of generally hard, medium, and soft layers include medium inner-medium outer, hard outer-medium inner, and soft outer-soft outer layering combinations. Any of the extra firm, firm, medium, soft, extra soft, and ultra soft materials may be combined to form the first and second layers of padding.

Examples of such combinations for any of padding segments 510, 520, 530, 540, and 550 can include a first layer comprising extra firm (having a first durometer with a compression force deflection in a range of 16-26 psi) silicone foam and a second layer comprising silicone foam of any of the following types: firm (having a second durometer with a compression force deflection in a range of 12-20 psi), medium (having a second durometer with a compression force deflection in a range of 6-14 psi), soft (having a second durometer with a compression force deflection in a range of 2-7 psi), extra soft (having a second durometer with a compression force deflection in a range of 1-5 psi), or ultra soft (having a second durometer with a compression force deflection of about 1.5 psi).

Other examples of such combinations for any of padding segments 510, 520, 530, 540, and 550 can include a first layer comprising firm (having a first durometer with a compression force deflection in a range of 12-20 psi) silicone foam and a second layer comprising silicone foam of any of the following types: extra firm (having a second durometer with a compression force deflection in a range of 16-26 psi), medium (having a second durometer with a compression force deflection in a range of 6-14 psi), soft (having a second durometer with a compression force deflection in a range of 2-7 psi), extra soft (having a second durometer with a compression force deflection in a range of 1-5 psi), or ultra soft (having a second durometer with a compression force deflection of about 1.5 psi).

Another set of examples of such combinations for any of padding segments 510, 520, 530, 540, and 550 can include a first layer comprising medium (having a first durometer with a compression force deflection in a range of 6-14 psi) silicone foam and a second layer comprising silicone foam of any of the following types: extra firm (having a second durometer with a compression force deflection in a range of 16-26 psi), firm (having a second durometer with a compression force deflection in a range of 12-20 psi), soft (having a second durometer with a compression force deflection in a range of 2-7 psi), extra soft (having a second durometer with a compression force deflection in a range of 1-5 psi), or ultra soft (having a second durometer with a compression force deflection of about 1.5 psi).

In still other examples, such combinations for any of padding segments 510, 520, 530, 540, and 550 can include a first layer comprising soft (having a first durometer with a compression force deflection in a range of 2-7 psi) silicone foam and a second layer comprising silicone foam of any of the following types: extra firm (having a second durometer with a compression force deflection in a range of 16-26 psi), firm (having a second durometer with a compression force deflection in a range of 12-20 psi), medium (having a second durometer with a compression force deflection in a range of 6-14 psi), extra soft (having a second durometer with a compression force deflection in a range of 1-5 psi), or ultra soft (having a second durometer with a compression force deflection of about 1.5 psi).

In further examples, such combinations for any of padding segments 510, 520, 530, 540, and 550 can include a first layer comprising extra soft (having a first durometer with a compression force deflection in a range of 1-5 psi) silicone foam and a second layer comprising silicone foam of any of the following types: extra firm (having a second durometer with a compression force deflection in a range of 16-26 psi), firm (having a second durometer with a compression force deflection in a range of 12-20 psi), medium (having a second durometer with a compression force deflection in a range of 6-14 psi), soft (having a second durometer with a compression force deflection in a range of 2-7 psi), or ultra soft (having a second durometer with a compression force deflection of about 1.5 psi).

In yet further examples, such combinations for any of padding segments 510, 520, 530, 540, and 550 can include a first layer comprising ultra soft (having a first durometer with a compression force deflection of about 1.5 psi) silicone foam and a second layer comprising silicone foam of any of the following types: extra firm (having a second durometer with a compression force deflection in a range of 16-26 psi), firm (having a second durometer with a compression force deflection in a range of 12-20 psi), medium (having a second durometer with a compression force deflection in a range of 6-14 psi), soft (having a second durometer with a compression force deflection in a range of 2-7 psi), or extra soft (having a second durometer with a compression force deflection in a range of 1-5 psi).

In some embodiments, the second layer 516 of the second cushioning material has more open space on its upper or lower surface due to perforations than the first layer 512 of the first cushioning material, which has, in the embodiment shown, a surface area of about 7.712 in$^2$. In another aspect, the total surface area of the cavities formed by the perforations 518 in the second layer 516 of the second cushioning material is higher than the total surface area of the cavities formed by the perforations 514 in the first layer 512 of the first cushioning material, for example, the total surface area of the cavities in the second layer 516 is about 5.858 in$^2$.

In some embodiments, the perforation patterns can be chosen taking into consideration the durometer (e.g., hardness) and density of each layer specific to the cushioning material used. The perforations in the layers of cushioning material also improve heat dissipation and air-flow. For the brow pad 510, the volume of the first cushioning material removed from the first layer 512 in forming the plurality of perforations 514 is about 1.179 in$^3$ and the volume of the second cushioning material removed from the second layer 516 in forming the plurality of perforations 518 is about 3.033 in$^3$.

The differences between the respective first and second perforation patterns can also aid in visually deciphering the first layer 512 from the second layer 516. The outer layer of primarily circle die-cuts may be laid out over the grid formed by the second perforations 518 formed in the second layer 516 to optimize air-flow between the first layer 512 and the second layer 516. Additionally, a higher perforation count may be used in the first layer 512 on the foam to increase the degree of compression and softness of the first compression material. The first perforations 514 comprise round holes to provide flexibility to explore actual hole count among the different designs, but as described above the first perforations 514 do not have to be circular. The actual design and perforation patterns should take into account the amount of material removed, not simply the shape of the die-cuts.

Figure 29:
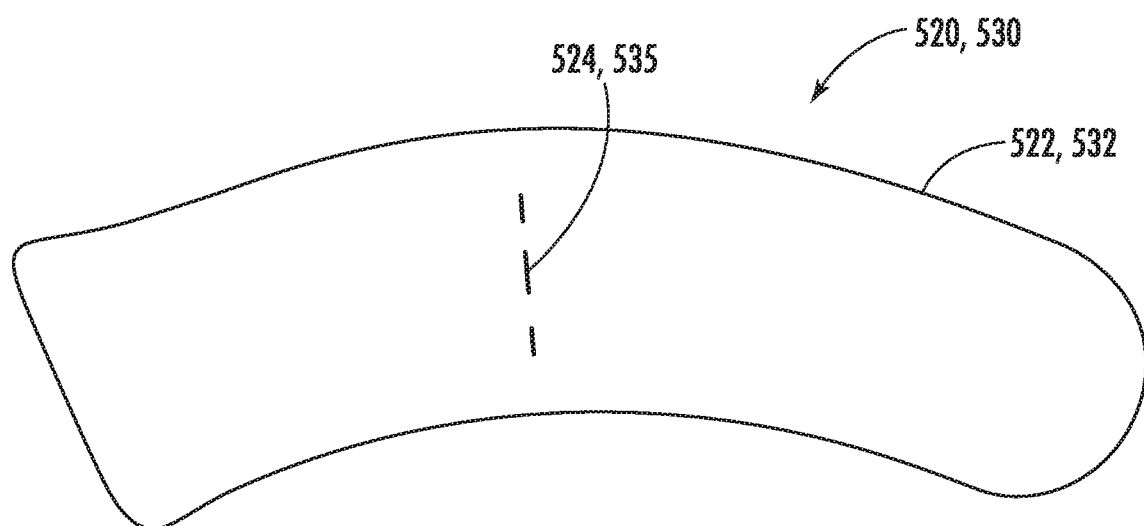
FIG. 29 is a top view of an example embodiment of a side pad of the head wearable device shown in FIGS. 1-7, in accordance with the disclosure herein.
Figure 30:
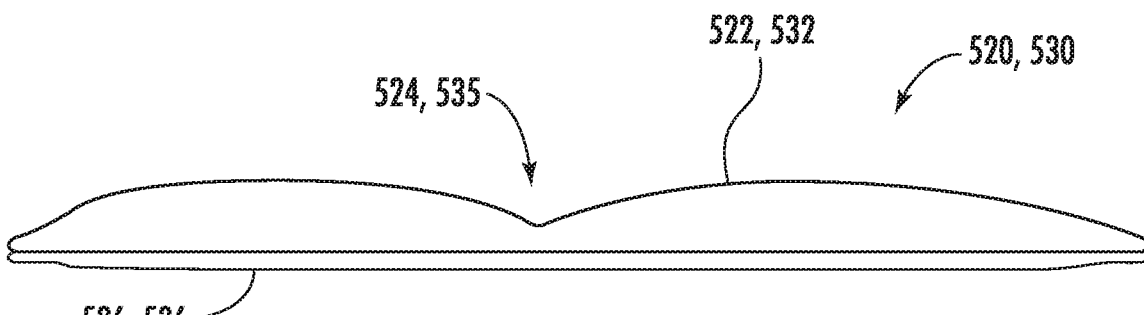
FIG. 30 is a side view of the side pad of FIG. 29, in accordance with the disclosure herein.

Referring to FIGS. 29 and 30, the top cover 522/532 of the side pads 520/530 can be made of fabric, for example, Darlington 96630 fabric manufactured by Darlington, which is a 4-way stretch Heavy Weight Tricot with a 356 gsm weight. The pad shown here is a side pad 520/530 for one side portion of the headband 100. The side pad 520/530 for the other side portion of the headband 100 is a mirror image of the side pad 520/530 as shown.

The rear 526/536 of the side pad 520/530 includes an attachment that secures the side pad 520/530 to the lateral strap 120A/120B of the headband 100. An example of a suitable attachment includes a hook-and-loop fastener system. The side pad 520/530 is filled with open-cell urethane foam or other suitable cushioning material to provide the desired level of support and comfort. A depression 524/534 can be formed by stitching across the side pad 520/530, thereby creating two or more padding segments in the side pad 520/530.

Figure 31:
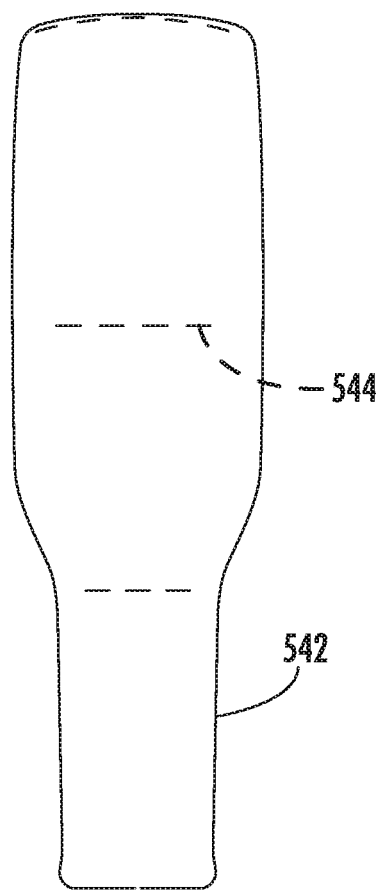
FIG. 31 is a top view of an example embodiment of a top pad of the head wearable device shown in FIGS. 1-7, in accordance with the disclosure herein.
Figure 32:
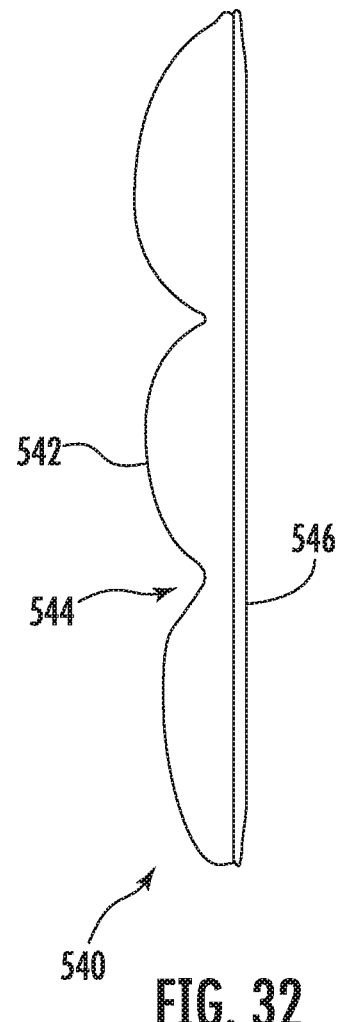
FIG. 32 is a side view of the top pad of FIG. 31, in accordance with the disclosure herein.

Referring to FIGS. 31 and 32, like the side pad shown in FIGS. 29 and 30, the top pad 540 can be made of fabric, for example, Darlington 96630 fabric. In the embodiment shown, the rear 546 of the top pad 540 includes a hook and loop fastener strip. Other suitable attachment types are contemplated. The top pad 540 is filled with open-cell urethane foam or any other suitable cushioning material, and the foam can be of any suitable thickness, for example, ¾" urethane foam support.

Although the top pad 540 and the side pad 520/530 are described herein each in singular form, there may be more than one top pad 540 and at least two side pads 520/530 for the two lateral straps 120A/120B of the headband 100. Each of these pads may have similar constructions but different shapes, lengths, thickness, curvatures, and the like to adapt the respective pad to the corresponding contour of the strap of the headband 100 for attachment. In addition, although the respective pads are shown as segmented pieces, one or more of the padding segments may be connected or all may be formed as an integral portion of the padding system 500.

The padding segments 510, 520, 530, 540, and 550 in the padding system 500 can be attached the headband 100 and the occipital basket 150 in various ways, either permanently or removably, for example, by hook and loop fasteners, snapping members, stitching, adhesive, ties, and any other suitable types of attachment known in the art. In an example embodiment, the brow, side and top pads 510, 520, 530, and 540 are all backed with a die-cut loop material to anchor them to the headband 100.

Figure 16:
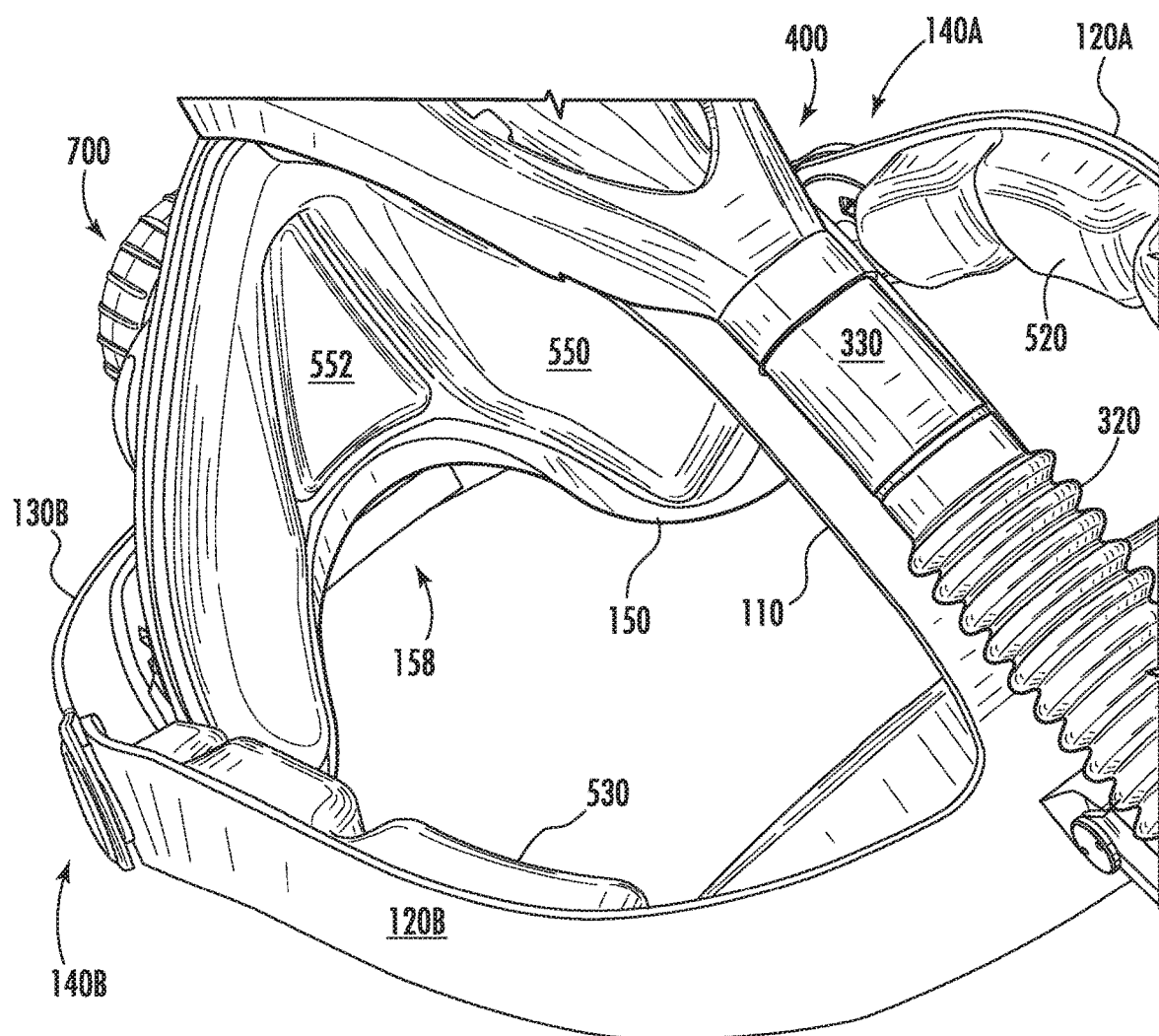
FIG. 16 is a view of the head wearable device of FIGS. 1-7 showing the padding arranged therein, in accordance with the disclosure herein.

The occipital basket 150 comprises at least one padding segment 550 removably attached thereto. As shown in FIG. 16, the occipital basket 150 comprises a cut-out 158, or notch, formed at the bottom edge thereof that defines a location where a wearer's hair can exit the occipital basket 150 without substantially interfering with the occipital basket 150 fitting securely against the rear of the wearer's head. The cut-out 158 is also formed to accommodate any features of a head wearable garment (e.g., a knot used to secure a surgical cap over the head of the wearer). In the embodiment of FIGS. 1-7, the rear pad 550 is a unitary (e.g., integral or monolithic) padding segment that is attached to the occipital basket 150 by a retention strap 566 (see FIG. 25) and netting 564 (see FIG. 25) that contain each of the lower corners of the occipital basket 150 (e.g., on opposite sides of the cut-out) therein and an upper strap 560 (see FIG. 25) which passes around the strap 152 of the occipital basket 150 and is secured thereto by snaps 562 (see FIG. 25) or any other suitable fastener. As shown at least in FIG. 16, the rear pad 550 on the occipital basket 150 has an outer contour/profile shape that is substantially similar to that of the occipital basket 150 itself, including the cut-out 158. Furthermore, the rear pad 550 on the occipital basket 150 comprises a cut-out recessed region 556 to accommodate a wearer's hair style without interfering with the head wearable device 1 being sufficiently secured over the wearer's head and to avoid pressure that may push against the back of the wearer's head.

Figure 33:
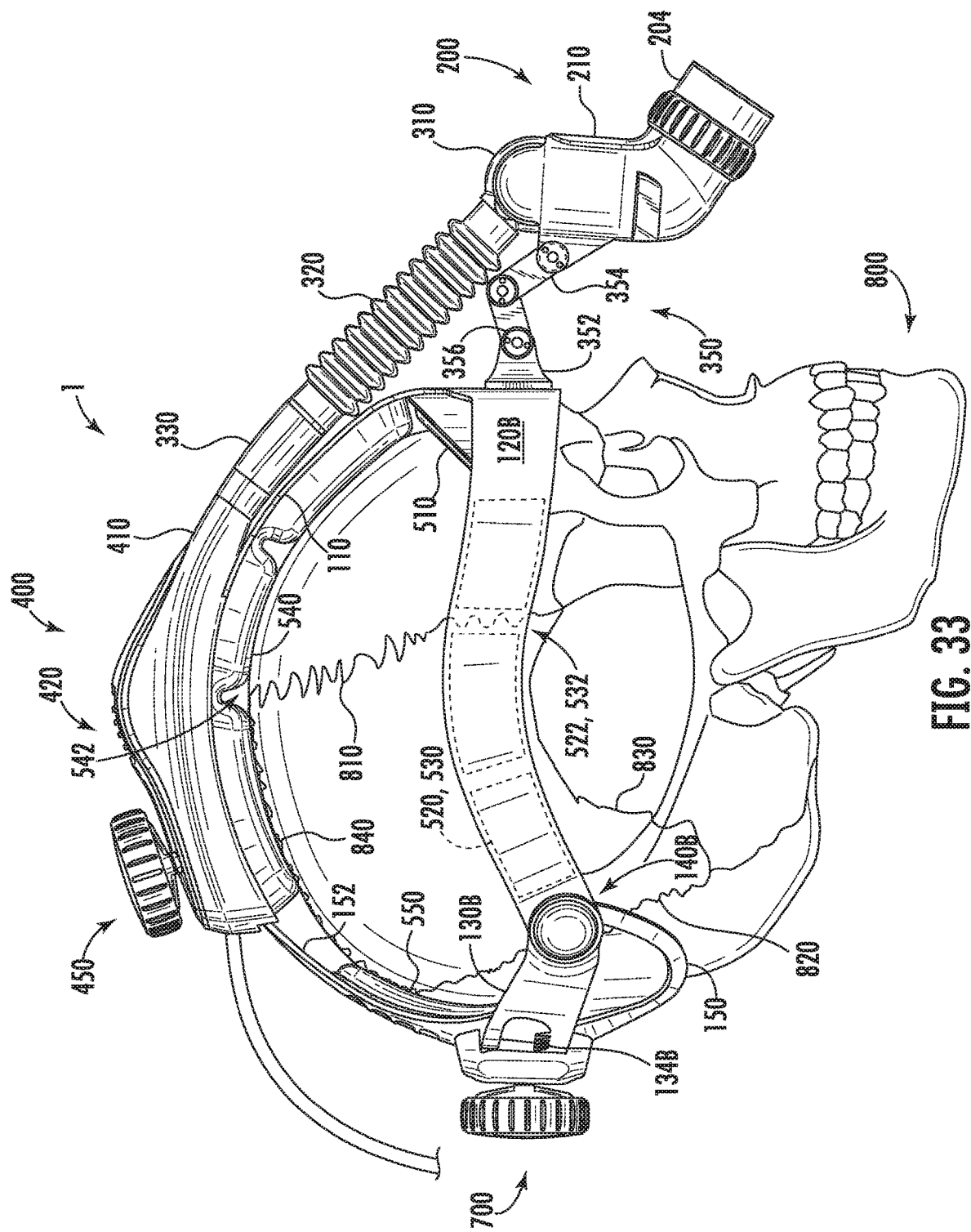
FIG. 33 is a side view of the embodiment of the head wearable device shown in FIGS. 1-7, showing example placement of the padding relative to the sutures formed in a human skull.

FIG. 33 shows an embodiment of the head wearable device 1, similar to that shown in FIGS. 1-7, fitted on and over a human skull, generally designated 800, to demonstrate possible and what can be preferred placement of the padding segments (e.g., 510, 520, 530, 540, 550) relative to skull region joinder lines or sutures, such as for example sutures 810, 820, 830, and/or 840, that exist between adjacent skull plates of the skull 800 and are configured to be positioned on a head without covering or being disposed or positioned over any or a substantial portion of the skull sutures such as sutures 810 shown. As shown, the padding segments are spaced such that, in at least some configurations, the weight of the head wearable device 1 is not placed on or over the skull sutures. For example, the shape of the lateral straps 120A/120B and the hinges 140A/140B avoid placement over, and do not contact and/or put pressure on, the squamous suture 830 and the lambdoid suture 820, while the top pad 540 does not contact at least a portion of the sagittal suture 840. As such, the side pads 520/530 of the lateral straps 140A/140B do not contact or apply pressure over any suture (e.g., 810, 820, 830, and/or 840) of the skull 800 of the wearer of the head wearable device 1. In the embodiment shown, a gap, generally designated 542, is present between segments of the top pad 540 so that the top pad 540 does not contact the head of the wearer in a region covering or over the coronal suture 810 of the skull 800 of the wearer. Stated differently, the top pad 540 is spaced apart from the head of the wearer over one or more sutures 810 of the wearer's skull 800. As such, the top pad 540 does not contact the wearer's head at areas of the sutures 810 of the wearer's skull 800. A gap, generally designated 522, 532, is present between segments of the side pads 520, 530 so that the side pads 520, 530 do not contact the head of the wearer in a region covering or over a suture 810 of the skull 800 of the wearer. The side pad 520, 530 is therefore against the head but can be laterally spaced apart from the head of the wearer over one or more sutures 810 of the wearer's skull 800. As such, the side pads 520, 530 do not contact the wearer's skull at the sutures 810 of the wearer's skull 800. In some embodiments, the top pad 540 and/or the side pads 520, 530 can be adjusted positionally so that the gap 522, 532, 542 can be positioned over the suture 810 of the skull of the wearer to provide enhanced comfort for the wearer during extended periods of use of the head wearable device 1. While FIG. 33 is a view of one side of the head wearable device 1 over a skull 800 of the wearer, the opposing view is identical to (e.g., is a mirror image of) the side view of FIG. 36, such that the features shown therein and described hereinabove are present for both sides of the head wearable device 1 relative to the skull 800 of the wearer.

Figure 10:
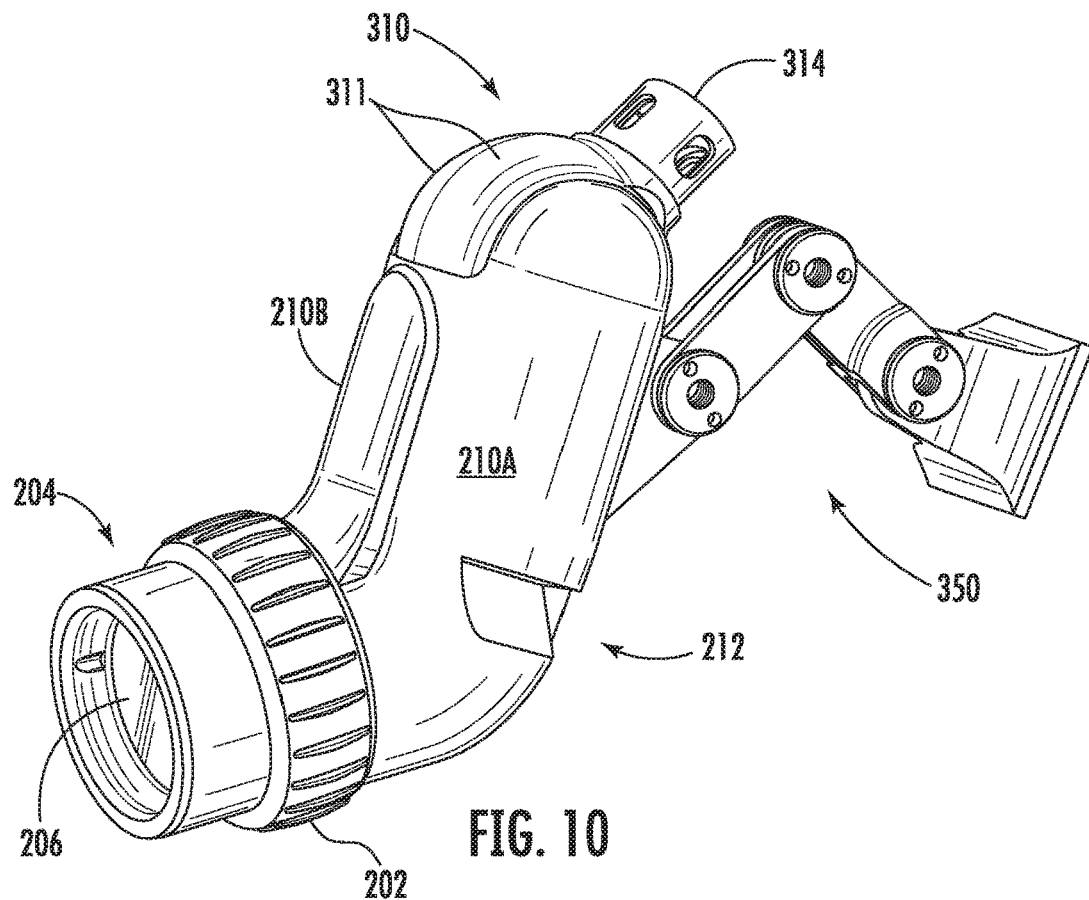
FIGS. 10-12 show various aspects of the thermal management features of the head wearable device of FIGS. 1-7, in accordance with the disclosure herein.
Figure 11:
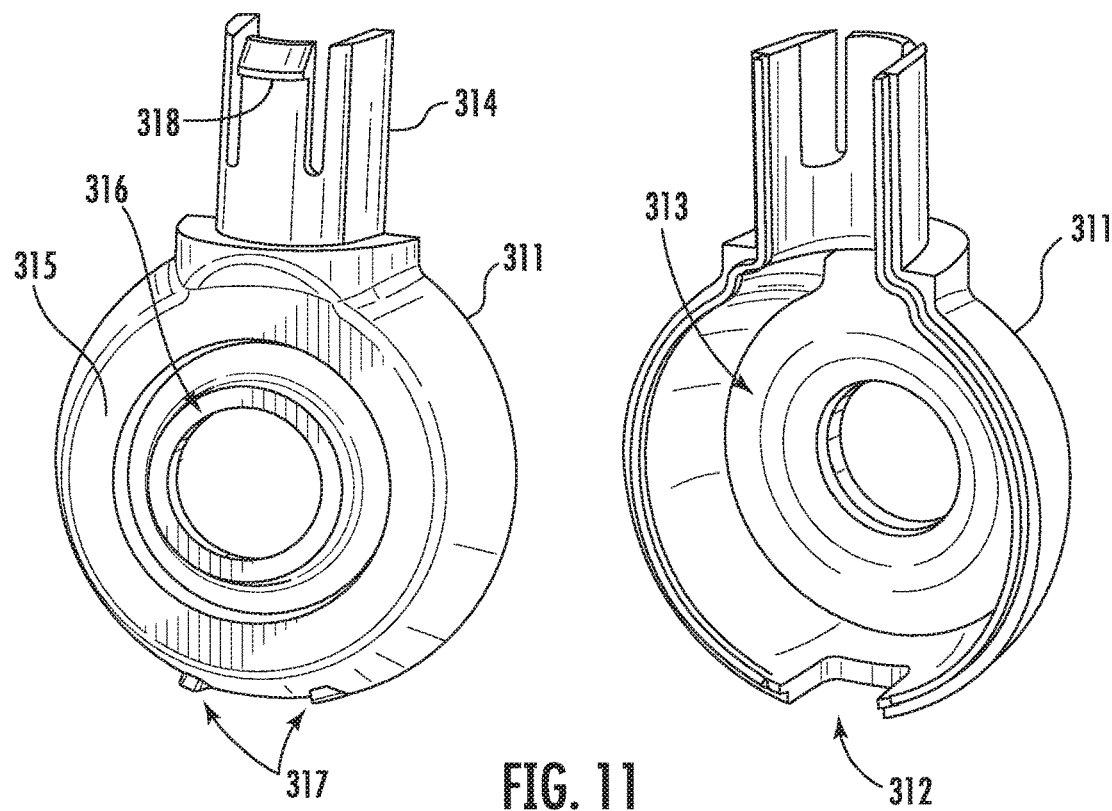
Figure 17:
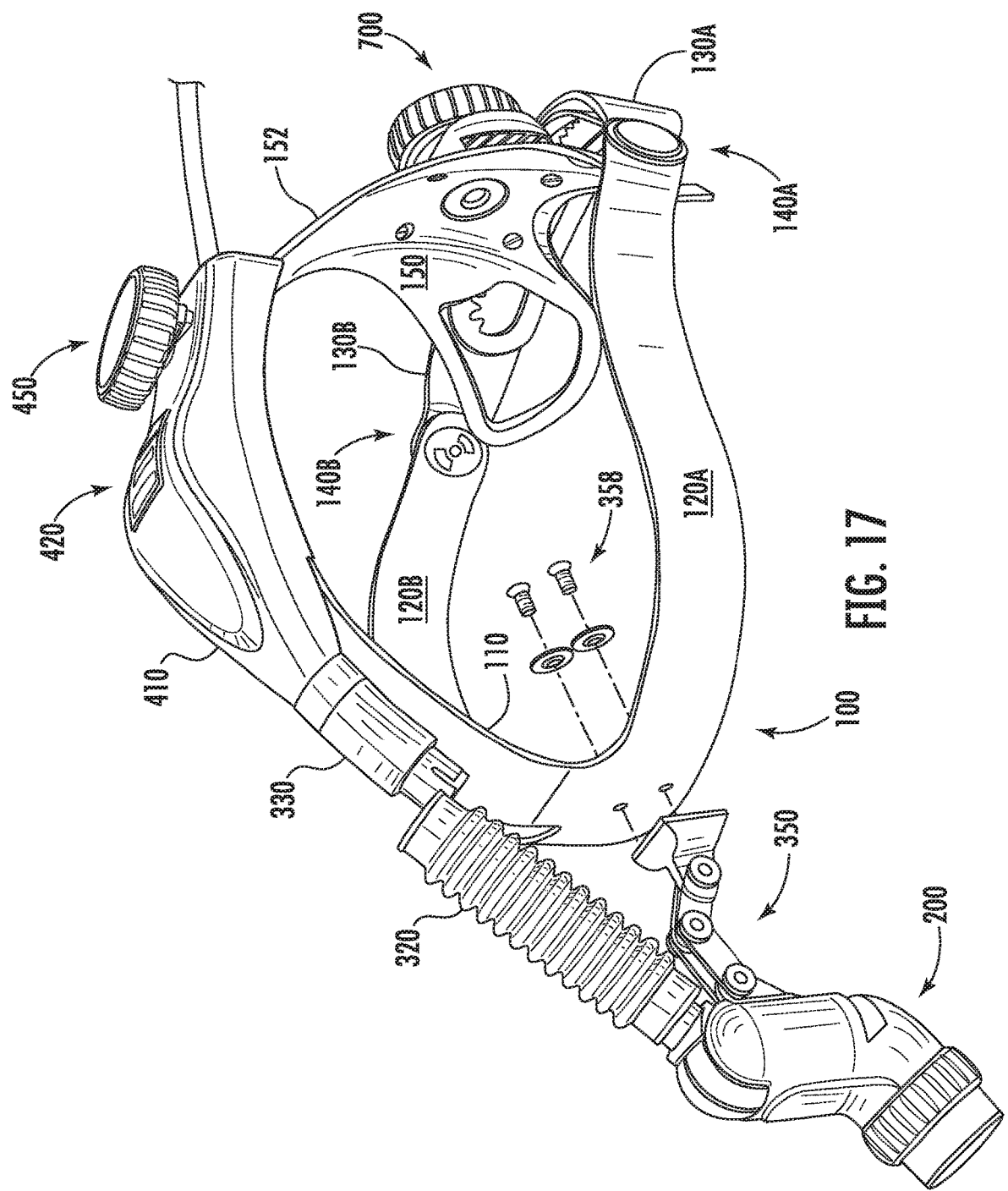
FIG. 17 is an assembly view of the head wearable device of FIGS. 1-7 with the padding omitted, in accordance with the disclosure herein.

The luminaire 200 comprises an external housing 210 and is attached at the forward edge of the headband 100 by any suitable mechanical linkage, generally designated 350. In some embodiments, the mechanical linkage 350 is a statically attached mounting point to which the luminaire 200 is rigidly and/or pivotably attached. In the embodiment shown, the mechanical linkage 350 comprises a mount that is connected to the front of the headband 100 and linkage bars 354 that are pivotably connected together by linkage rollers 356. As shown in FIG. 17, the mechanical linkage 350 is secured to the headband 100 by mounting hardware (e.g., screws and washers), generally designated 358, which pass through the thickness of the headband 100 at the front thereof. The mechanical linkage 350 is provided to allow the angle of the luminaire 200 relative to the headband 100 and the distance of the luminaire 200 from the headband 100 to be controlled independently. The luminaire 200 comprises, as is shown at least partially in FIGS. 10-12, at least one LED 232 (e.g., any suitable light source), which can be mounted on a substrate. Such a substrate can be affixed (e.g., rigidly) to a heatsink 220 located within the luminaire housing 210 to conduct heat generated by the at least one LED 232 into the heatsink 220. Such a substrate can have surface-mount connection points for the LED's power and sensing electrical needs. The substrate can be formed such that the LED 232 and the heatsink 220 are located in opposing first and second regions of the luminaire housing 210, the first region being adjacent the lens cell and the second region being located away from (e.g., spaced apart from) the LED 232. The substrate may be configured to allow for a straight-line optical cell configuration, as opposed to a bent-configuration, thereby eliminating the need for a mirror to perform the optical bend necessary for such configurations. In some embodiments, such a substrate can be a laminated printed circuit board (PCB) and/or comprises copper to provide enhanced thermal conductivity between the LED 232 and the heatsink 220 to the substrate. The use of copper in such a substrate can be advantageous, as copper's high thermal conductivity allows for the efficient conduction of heat from the LED 232 to the heatsink 220 for dissipation into a cooling air stream flowing into the luminaire housing 210 via the inlet 212, two of which are formed on opposing sides of the luminaire housing 210. The heatsink 220 can be of any suitable construction, including, for example, extrusion, soldering, skiving, and the like, and can comprise any suitably conductive material, such as, for example, aluminum or copper.

Figure 12:
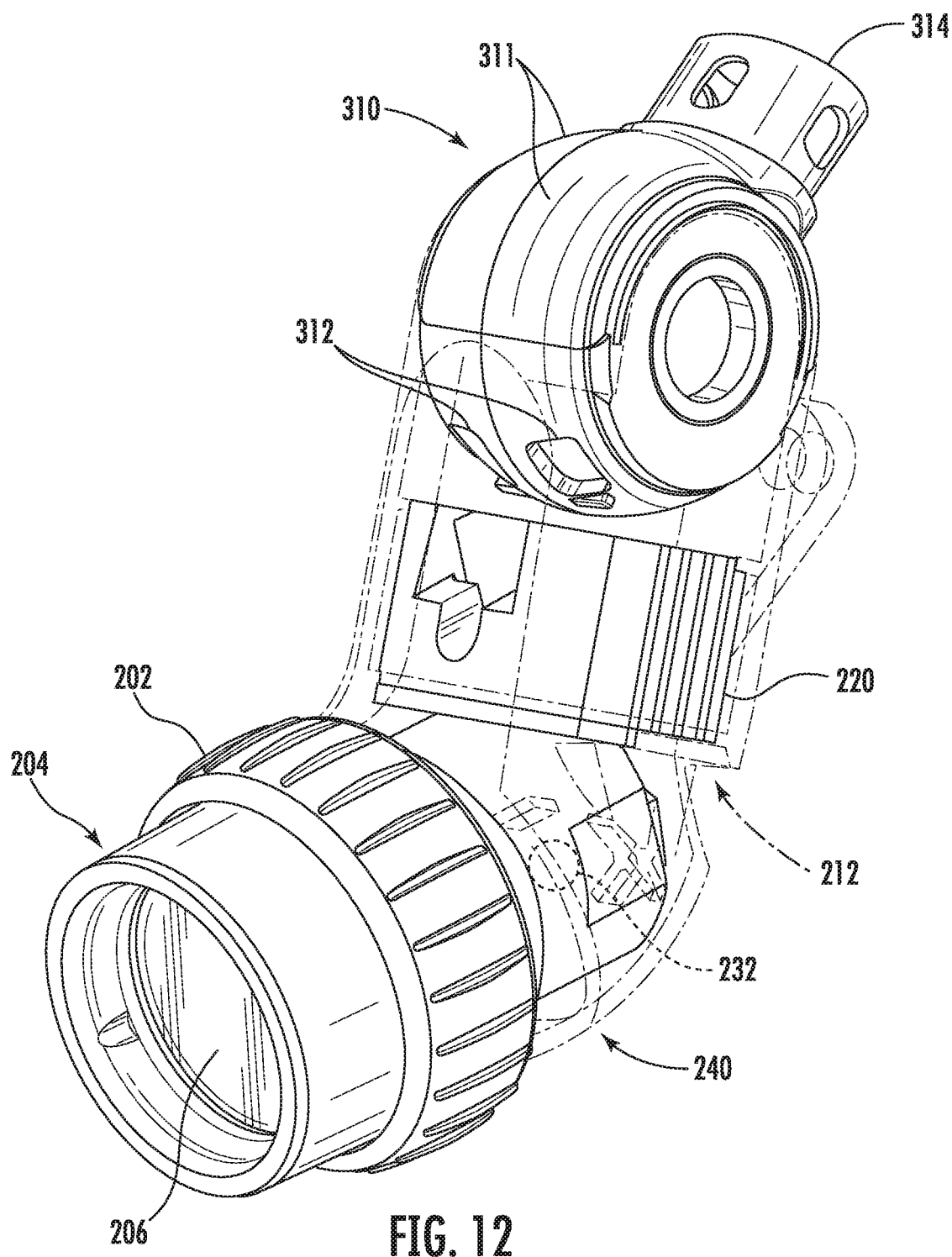

The luminaire housing 210 is connected, via a pivoting ball joint 310, to a duct 300 system. The ball joint 310 is formed of two half-members 311 assembled together to form the ball joint 310 and the luminaire housing 210 is clamped around the outer lateral edges of the ball joint 310 to allow the luminaire housing 210 to rotate independently of and about the ball joint 310. The ball joint 310 is rotatable about an axis that is perpendicular to the duct system 300, unlike known solutions that rotate about an axis parallel to the air flow path to avoid inducing kinks or other obstructions into the air flow path. The ball joint 310 has a hole 312 formed radially about a portion of the circumference of the ball joint 310. The ball joint 310 has an exhaust port 314 formed in the circumference of the ball joint 310 and directed radially away from the center of the ball joint 310. The exhaust port 314 and the hole 312 are located around the circumference of the ball joint 310. As such, the ball joint 312 defines an airflow path through the body thereof, with the hole 312 and the exhaust port 314 being defined, respectively, as the inlet and the outlet of the airflow path through the ball joint 310. The cross-sectional area of the hole 312 has a size to provide sufficient air flow across the heatsink 220 of the luminaire 200 to sufficiently cool the LED 232. In the embodiment shown, the hole 312 and the exhaust port 314 are formed such that they are located substantially diametrically opposite each other about the circumference of the ball joint 310. The ball joint 310 has locating features 317 formed therein and/or thereon that define a range of rotary movement of the luminaire housing 210 and the ball joint 310 relative to each other. This range of rotary movement defined by the locating features 317 is such that the hole 312 remains positioned internal to the luminaire housing 210 at all operating positions of the luminaire 200 relative to the headband 100 to avoid creating an unwanted air inlet in the luminaire housing 210 upstream of the heatsink 220. Similarly, the lateral sides 315 of the ball joint 310 can be solid or be sealed with a gasket to prevent any air leakage into and/or out of the duct system 300. In some embodiments, such as is shown in FIG. 12, the hole 312 comprises two discrete holes 312, one hole 312 being formed in each side of the two half-members 311 of the ball joint 10

The ball joint 310 is lockingly connected at the exhaust port 314 thereof to a flexible duct 320 that can have, for example, a corrugated construction that allows for bending deflections as well as elongations or contractions thereof when the position of the luminaire 200 relative to the headband 100 is changed (e.g., by adjusting the position of the mechanical linkage 350). The exhaust port 314 of the ball joint 310 comprises, in the embodiment shown, a snapping interlock system 318 to ensure sufficient mechanical interlocking between the exhaust port 314 and the flexible duct 320. The flexible duct 320 is connected at a distal end thereof to a rigid duct 330 attached to the upper housing 400 on the top strap of the headband. This rigid duct 330 has, at a distal end thereof from the flexible duct 320, an air moving device 332 attached thereto, the outlet of the air moving device 332 being oriented to blow out from a hot air exhaust 420. The luminaire housing 210 has at least two air inlets 212 formed therein (e.g., integrally) at locations configured to draw ambient air across the heatsink 220. The air moving device 332 can be of any suitable type, including a fan, blower, piezoelectric device, or the like.

A sensor is provided to monitor a temperature of the LED, either directly or indirectly, and a controller is provided to thermostatically control the air moving device 332 to maintain the temperature of the LED 232 within a prescribed operating temperature range. In examples of indirect thermal management, the temperature of a substrate to which the LED 232 may be attached and/or mounted, the heatsink 220, and/or the air flow passing through the duct system 300 may be monitored, preferably in conjunction with the operational state (e.g., as a percentage of maximum air flow) of the air moving device 332. Gaskets 335 are provided on the inlet and/or the outlet faces of the air moving device 332 to prevent introducing leakage paths within the duct system 300.

In some embodiments, the ball joint 310 comprises two half-members 311 ultrasonically welded together to form the body of the ball joint 310, which is held in place within an end of the luminaire housing 210 sealingly clamped between flanges thereof, which may, in some embodiments, itself be ultrasonically welded together from separate and discrete housing members 210A/210B. This sealing clamping of the luminaire housing 210 about the ball joint 310 can, in some embodiments, be achieved by placing one or more gaskets circumferentially between the ball joint-luminaire housing interface being sealed. In some such embodiments, the one or more gaskets can be installed within a groove formed in a surface of the ball joint 310, the luminaire housing 210, or both. The two half-members 311 have a central cavity, generally designated 313, formed therein when assembled together. In the embodiment shown, the ball joint 310 sits loosely (e.g., sufficiently loose to allow the pivoting motion of the luminaire housing 210 relative to the ball join 310) at the proximal end (relative to the headpiece) of the luminaire housing 210, with O-ring gaskets being provided in a recess around central protrusion 316 to produce an air tight interface between the ball joint 310 and the luminaire housing 210 to minimize leakage paths in the airflow path. As shown, the ball joint 310 can pivot freely within the proximal end of the luminaire housing 210 over a range of motion as determined by the vertical position of both the luminaire 200 and any accompanying downstream exhaust components (e.g., the flexible duct 320, the rigid duct 330, etc.). The housing 210 is connected to the mechanical linkage 350 at mounting tab 214.

As such, a method of cooling a luminaire 200 of a head wearable device 1 is provided. The method comprises providing an LED 232 within a luminaire housing 210, forming at least one air inlet 212 in the luminaire housing 210, attaching a heatsink 220, directly or indirectly (e.g., via a substrate) to the LED 232, arranging the heatsink 220 adjacent the at least one air inlet 212 of the luminaire housing 210, connecting the luminaire housing 210 to the ball joint 310, forming a hole 312 and an exhaust port 314 in the ball joint 310, connecting a first end of the flexible duct 320 to the ball joint 310 at the exhaust port 314, connecting a rigid duct 330 to the flexible duct 320 at the second end of the flexible duct 320, installing the air moving device 332 within a hot air exhaust 420 of the upper housing 400, monitoring the temperature of the LED 232 within the luminaire 200, and controlling the air moving device 332 to produce an air flow from the at least one inlet 212 in the luminaire housing 210, through the heatsink 220, through the ball joint 310, through the flexible duct 320, through the rigid duct 330, through the air moving device 332, and exhausted from the hot air exhaust 420 formed in the upper housing 400, which is attached to a top strap 110 of a headband 100 of the head wearable device 1.

Power can be provided to the head wearable device 1 via a power cord 602 attached to the upper housing 400. In some embodiments, the power cord 602 is of a twist-lock type, such that power cannot be accidentally disconnected from the head wearable device 1 merely by pulling the power cord 602 out of the holster 600 without an accompanying twisting motion at the connector interface. The power cord 602 may be connected to a holster 600 that is wearably attached to a wearer of the head wearable device 1. In some embodiments, the holster 600 is configured to have one or more battery packs installed therein, which allows the wearer of the head wearable device 1 unrestricted movement. In some embodiments, the holster 600 is configured to be connected to a substantially continuous power source (e.g., a wall electrical outlet) for substantially indefinite operation. The holster 600 comprises an intensity control (e.g., a rotary control knob) that regulates power to the LED 232 from either battery or the direct power supply and controls the intensity emitted from the LED 232 and, consequently, also from the luminaire 200.

The luminaire 200 is configured to produce a pure white light output without a yellow ring being present around the perimeter of the light output area. Apertures may be used in optical devices such as cameras and telescopes to limit light entering the device. Such apertures may be manufactured from any suitable material, including from a thin metal and may, in some aspects, advantageously be either anodized black or painted black to minimize unwanted reflections within the optical path. It is known that such apertures may be suspended mechanically within the lens cell in any manner and orientation, as dictated by the optical design and subsequent testing iterations. The presently disclosed luminaire 200 is thus configured to restrict unwanted stray light (aberrations) from exiting the optical path, thereby ensuring a near ideal white-spot presentation. It is known that aberrations in the spot presentation can result from light scattering in the optical train due to source light reflections off of internal mechanical components, LED "yellow light phenomenon," and the like. It is advantageous to ensure that the optical train will yield a substantially homogeneous white-spot presentation. The presently disclosed embodiment optimizes the projection of white light while helping to restrict both stray light reflections and yellow light from exiting the optical path. As shown, the light projecting portion of the luminaire 200 is configured to produce a white-spot presentation having an adjustable focal point and/or focal length, thereby allowing for a white-spot presentation having an adjustable size (e.g., diameter). The focal length and spotlight size is adjustable by turning the adjustment knob 202 (see FIG. 12) provided on the luminaire 200. The outer lens 206 is contained within an outer lens structure, generally 204, at the outlet of the optical train.

Figure 18:
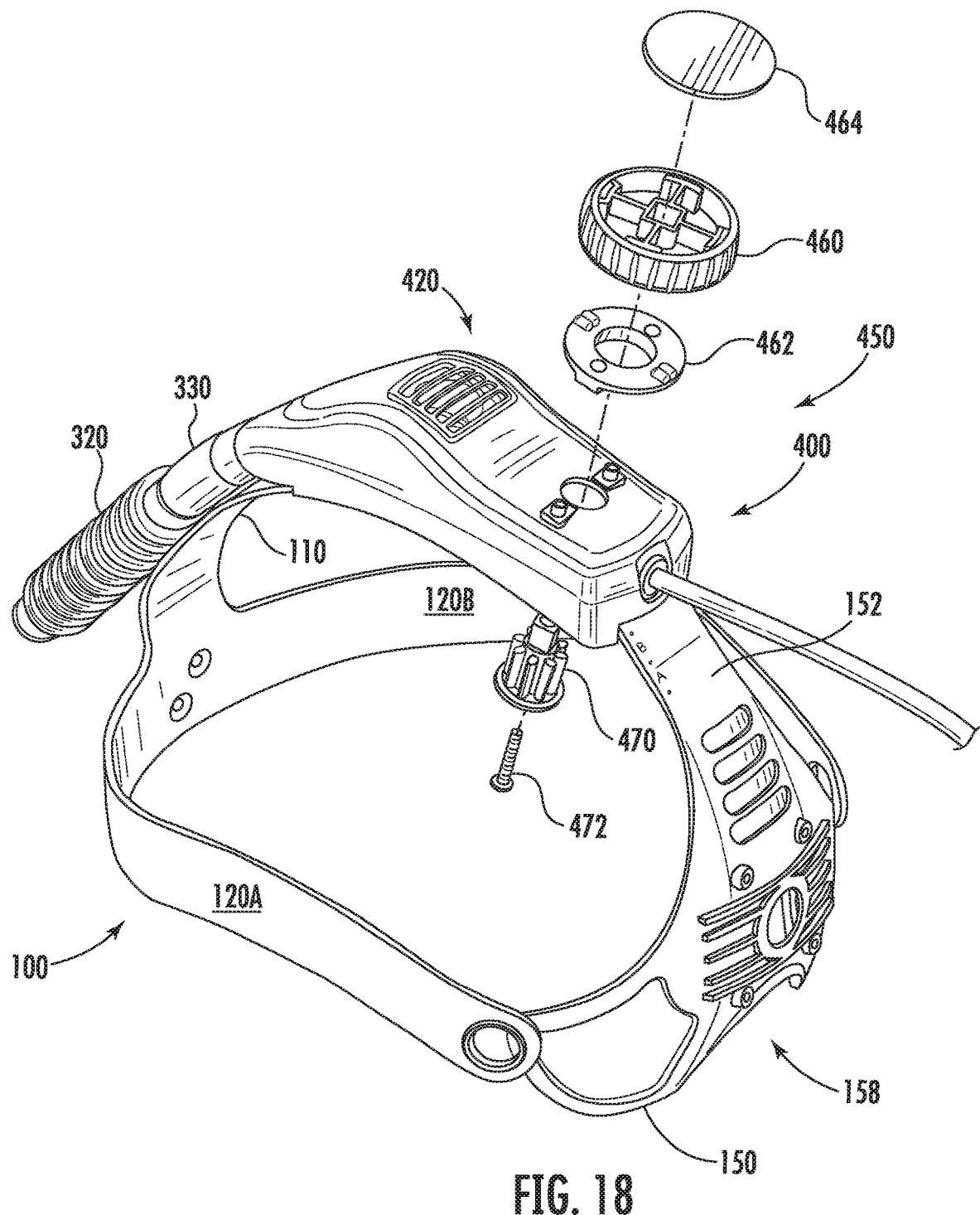
FIGS. 18 and 19 are partial exploded views to show the adjustment features of the head wearable device of FIGS. 1-7, in accordance with the disclosure herein.
Figure 19:
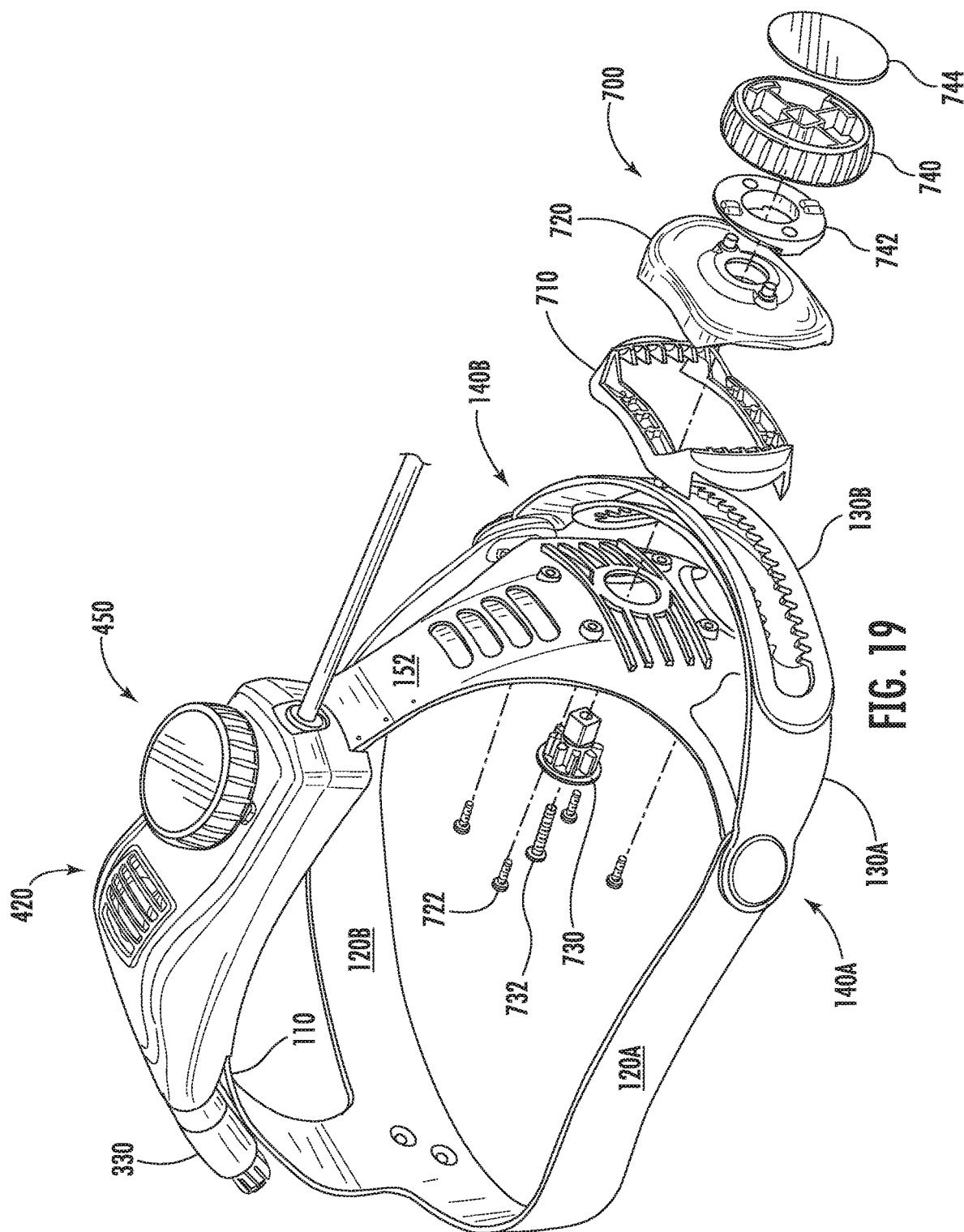

FIG. 17 is a partially exploded view of the head wearable device 1, showing the attachment of the luminaire 200, via the mechanical linkage 350, to the headband 100 and the flexible duct 320 to the rigid duct 330. FIG. 18 is a partially exploded view of the components of the depth adjuster 450 for the position of the strap 152 of the occipital basket 150 relative to the upper housing 410 attached to the top strap 110 of the headband 100. In some embodiments, the occipital basket 150 is pivotable to better adjust to the head shape of the wearer. The depth adjuster 450 shown in FIG. 18 comprises a gear 470 that engages with teeth 156 (see FIGS. 13-15) formed on the inner surface of the slot 154 (see FIGS. 13-15) of the strap 152 that is being positionally adjusted relative to the upper housing 400 and the top strap 110. The gear 470 projects through the upper housing 400 and is fixedly and rotationally coupled to an adjustment knob 460. The adjustment knob 460 is rotatably locked to the gear 470 by connector plate 462 and screw 472. A cover plate 464 is attached to the adjustment knob 460, but in some embodiments the cover plate 464 can be integrally formed as the adjustment knob 460. As such, a rotary movement of the knob 460 causes a corresponding rotary movement of the gear 470 and a corresponding lengthening or shortening of the strap 152 which engages with the gear 470. FIG. 19 is a partially exploded view of the components of the headband adjuster 700 for the circumference of the head wearable device 1. The headband adjuster 700 shown in FIG. 19 is largely similar to the depth adjuster shown in FIG. 18, but the rear housing comprises a two-part rear housing that has a base 710 that allows for visualization of the engagement of the teeth 134A/134B of the lateral extension straps 130A/130B with the gear 730 when assembling the head wearable device 1. This visualization internal to the headband adjuster 700 ensures that the lateral extension straps 130A/130B are each equally engaged around the gear 730 so the components of the head wearable device 1 are symmetrical about a vertical plane arranged along the longitudinal axis of the head wearable device 1. The headband adjuster 700 further comprises a cover panel 720 that engages at least partially over the base 710 to obscure the engagement of the gear 730 with the lateral extension straps 130A/130B during normal operation of the head wearable device 1. The gear 730 projects through a hole formed in the occipital basket 150 and the base 710 is secured to the occipital basket 150 at a predetermined mounting point, for example, by screws 722. The gear 730 is then fixedly and rotationally coupled to an adjustment knob 740 by screw 732, which passes through the occipital basket 150. The adjustment knob 460 is rotatably locked to the gear 730 by connector plate 742 and screw 732. A cover plate 744 is attached to the adjustment knob 740, but in some embodiments the cover plate 744 can be integrally formed as the adjustment knob 740. As such, a rotary movement of the adjustment knob 740 causes a corresponding rotary movement of the gear 730 and a corresponding lengthening or shortening of the circumference of the head wearable device 1.

A method of adjusting a size of a headpiece of a head wearable device to a head size of a wearer, the headpiece comprising a headband 100 and an occipital basket 150, is provided. The method comprises attaching an upper housing 400 to an external surface of a top strap 110 of the headband 100; inserting a strap 152 of the occipital basket 150 at least partially into the upper housing 400; engaging a first gear 470 with a plurality of teeth 156 formed in a slot 154, which is longitudinally oriented along a length of the strap 152 of the occipital basket 150; turning a first adjustment knob 460, which is rotationally locked to the first adjustment gear 470, to adjust a depth of the headpiece; attaching a second housing to an external surface of the occipital basket 150; inserting an end of at least two lateral extension straps 130A/130B into the second housing, with the end of a first lateral extension strap 130A being inserted from an opposite end of the housing from the end of a second lateral extension strap 130B, wherein the two lateral extension straps 130A/130B are hingedly attached to lateral straps 120A/120B of the headband 100 to define a circumference of the headpiece; engaging a second gear 730 with a plurality of teeth 134A/134B formed in a slot 132A/132B of each of the lateral extension straps 130A/130B such that the second gear 730 is engaged with both of the lateral extension straps 130A/130B; and turning a second adjustment knob 740, which is rotationally locked to the second adjustment gear 730, to adjust a circumference of the headpiece.

In some embodiments, the method comprises providing a first visual index along a length of the strap 152 of the occipital basket 150, the first visual index 157 comprising sequential alphanumeric characters to designate predetermined depth settings for the headpiece; providing a second visual index 136 along a length of at least one of the lateral extension straps 130A/130B, the second visual index 136 comprising sequential alphanumeric characters to designate predetermined circumference settings for the head wearable device 1; determining a wearer preference for the depth and circumference of the head wearable device 1 corresponding to the first and second visual indexes 157/136; placing the head wearable device 1 on the wearer's head; adjusting the first adjustment knob 460 such that the first visual index 157 indicates that the wearer preference for the depth of the head wearable device 1 has been achieved; and adjusting the second adjustment knob 730 such that the second visual index 136 indicates that the wearer preference for the circumference of the head wearable device 1 has been achieved.

In some aspects, a head wearable device comprises a headpiece; a housing attached to the headpiece; a luminaire attached to the headpiece, the luminaire comprising a luminaire housing and at least one light source located within the luminaire housing; a duct system connecting the luminaire to the housing; a ball joint rotatably connecting the duct system to the luminaire; and an air moving device configured to induce a cooling air flow through an inlet in the luminaire housing, through the heatsink, through the ball joint, through the duct system, and out of an exhaust in the housing on the top surface of the headpiece. In some embodiments of the head wearable device, the housing is attached to a top surface of the headpiece In some embodiments, the head wearable device comprises a controller configured to monitor a temperature of the at least one light source and to modulate an operational setting of the air moving device to maintain the temperature of the at least one light source within a predetermined operating range. In some embodiments of the head wearable device, the headpiece comprises a headband, which has at least a top strap and two lateral straps, and an occipital basket, wherein the headband is connected to the occipital basket and the headband and the occipital basket are independently adjustable relative to each other. In some embodiments of the head wearable device, the at least one light source comprises a light emitting diode (LED). In some embodiments of the head wearable device, the ball joint is pivotably and/or swivelably connected to the luminaire. In some embodiments of the head wearable device, the duct system comprises a flexible duct connected to a rigid duct. In some embodiments of the head wearable device, the air moving device is positioned inside the housing, within the rigid duct, in a position adjacent to the exhaust in the housing. In some embodiments of the head wearable device, the luminaire is attached to the headpiece by a mechanical linkage such that an angle and/or position of the luminaire relative to the headpiece is adjustable. In some embodiments of the head wearable device, the flexible duct comprises a corrugated construction such that a length thereof can be shortened or lengthened as the angle and/or position of the luminaire relative to the headpiece is adjusted. In some embodiments of the head wearable device, the ball joint defines a range of angular motion for the luminaire and comprises a passage and an exhaust port formed in a circumferential wall of the ball joint, the range of angular motion being such that the passage remains in a position to provide an air flow path from the luminaire housing into the ball joint. In some embodiments of the head wearable device, the passage and the exhaust port are arranged on substantially opposite sides of the ball joint. In some embodiments of the head wearable device, the passage is not externally visible from the luminaire housing at any point along the range of angular motion. In some embodiments, the head wearable device comprises a heatsink located within the luminaire housing. In some embodiments of the head wearable device, the luminaire is configured to optimize a projection of white light and restrict both stray light reflections and yellow light from exiting the lens cell. In some embodiments of the head wearable device, the lens cell is configured to produce a substantially homogeneous white-spot presentation. In some embodiments of the head wearable device, the lens cell comprises an adjustable focal length and/or focal point. In some embodiments, the head wearable device comprises a power cord attached to the upper housing attached to the top strap of the headband, the power cord being configured to receive power from a holster. In some embodiments of the head wearable device, the power is provided from a rechargeable battery or a continuous power source, and wherein the holster is configured to adjust an intensity of light output from the at least one light source.

In some aspects, a head wearable device comprises a headpiece comprising: a headband comprising a top strap and at least two lateral straps; an occipital basket comprising a strap, the occipital basket being attached to the headband by at least one lateral extension strap pivotably attached by a hinge to a distal end of each respective lateral strap of the headband; a first housing attached to an outer surface of the top strap of the headband; a depth adjuster attached to the first housing, the depth adjuster comprising a first gear rotatably fixed to a first knob; wherein the strap of the occipital basket comprises a slot with a plurality of teeth formed around a longitudinal edge of the slot; wherein the first gear is captively held within the slot and engages with the plurality of teeth; wherein the depth adjuster is configured such that a rotary movement of the first gear causes a longitudinal movement of the strap of the occipital basket to change a distance between the occipital basket and the first housing; wherein a depth of the headpiece changes when the distance between the occipital basket and the first housing changes, or increases or decreases; and wherein the strap comprises a first visual index comprising a first plurality of sequential characters, each of which correspond to one of a plurality of predetermined depth settings of the headpiece; and a second housing attached to an outer surface of the occipital basket; a headband adjuster at an outer surface of the occipital basket, the headband adjuster comprising a second gear rotatably fixed to a second knob; wherein the lateral extension straps each comprise a slot with a plurality of teeth formed around a longitudinal edge of the slot; wherein the second gear is captively held within the slot of each lateral extension strap and engages with the plurality of teeth of each of the lateral extension straps; wherein the headband adjuster is configured such that a rotary movement of the second gear causes a longitudinal movement of the lateral extension straps to change a circumference of the headpiece; and wherein at least one of the lateral extension straps comprises a second visual index comprising a second plurality of sequential characters, each of which correspond to one of a plurality of predetermined circumferential settings of the headpiece; wherein the head wearable device is configured such that the lateral extension straps rotate about the hinge, relative to the lateral straps as the depth of the headpiece changes. In some embodiments of the head wearable device, the first and second visual indexes comprise alphanumeric characters. In some embodiments of the head wearable device, the first visual index and the second visual index comprise different ranges and/or types of alphanumeric characters. In some embodiments of the head wearable device, the first visual index comprises a plurality of sequential letters and the second visual index comprises a plurality of sequential numbers. In some embodiments of the head wearable device, the first visual index comprises a plurality of sequential numbers and the second visual index comprises a plurality of sequential letters. In some embodiments, the head wearable device comprises padding on an inner surface of the headband and the occipital basket. In some embodiments of the head wearable device, a notch is formed into a lower edge of the occipital basket to prevent a wearer's hair from interfering with proper fitment of the headpiece about a head of a wearer. In some embodiments of the head wearable device, the padding on the occipital basket comprises a recessed area to prevent the wearer's hair from interfering with proper fitment of the headpiece about the head of the wearer. In some embodiments of the head wearable device, the padding is removably attached to the headband and the occipital basket. In some embodiments of the head wearable device, the padding is spaced apart from a surface of a head of a wearer of the head wearable device at a suture between adjacent plates of a skull of the wearer of the head wearable device.

In some aspects, a method of adjusting a size of a headpiece of a head wearable device to a head size of a wearer is provided, the headpiece comprising a headband and an occipital basket, and the method comprising attaching a first housing to an external surface of a top strap of the headband; inserting a strap of the occipital basket at least partially into the first housing; engaging a first gear with a plurality of teeth formed in a slot, which is longitudinally oriented along a length of the strap of the occipital basket; turning a first knob, which is rotationally locked to the first gear, to adjust a depth of the headpiece; attaching a second housing to an external surface of the occipital basket; inserting an end of at least two lateral extension straps into the second housing, with the end of a first lateral extension strap being inserted from an opposite end of the housing from the end of a second lateral extension strap, wherein the two lateral extension straps are hingedly attached to lateral straps of the headband to define a circumference of the headpiece; engaging a second gear with a plurality of teeth formed in a slot of each of the lateral extension straps such that the second gear is engaged with both of the lateral extension straps; and turning a second knob, which is rotationally locked to the second gear, to adjust a circumference of the headpiece. In some embodiments, the method comprises providing a first visual index along a length of the strap of the occipital basket, the first visual index comprising sequential alphanumeric characters to designate predetermined depth settings for the headpiece; providing a second visual index along a length of at least one of the lateral extension straps, the second visual index comprising sequential alphanumeric characters to designate predetermined circumference settings for the headpiece; determining a wearer preference for the depth and circumference of the headpiece corresponding to the first and second visual indexes; placing the head wearable device on the wearer's head; adjusting the first knob such that the first visual index indicates that the wearer preference for the depth of the headpiece has been achieved; and adjusting the second knob such that the second visual index indicates that the wearer preference for the circumference of the headpiece has been achieved. In some embodiments of the method, the first visual index and the second visual index comprise different ranges and/or types of alphanumeric characters. In some embodiments of the method, the first visual index comprises a plurality of sequential letters, the second visual index comprises a plurality of sequential numbers, and the wearer preference is designated by one of the plurality of sequential letters and one of the plurality of sequential numbers. In some embodiments of the method, the first visual index comprises a plurality of sequential numbers and the second visual index comprises a plurality of sequential letters. In some embodiments, the method comprises attaching padding on an inner surface of the headband and the occipital basket. In some embodiments, the method comprises forming a notch into a lower edge of the occipital basket to prevent a wearer's hair from interfering with proper fitment of the headpiece about a head of a wearer. In some embodiments, the method comprises forming a recessed area in the padding on the occipital basket to prevent the wearer's hair from interfering with proper fitment of the headpiece about the head of the wearer. In some embodiments of the method, the padding is removably attached to the headband and the occipital basket. In some embodiments, the method comprises spacing the padding apart from a surface of a head of a wearer of the head wearable device at a suture between adjacent plates of a skull of the wearer of the head wearable device.

In some aspects, a headlight device comprises a headband comprising a rear portion, a side portion and a top portion, the headband having an inner surface; a padding system comprising: a rear pad attached to the inner surface of the rear portion of the headband; a side pad attached to the inner surface of the side portion of the headband; a top pad attached to the inner surface of the top portion of the headband; and, optionally, a brow pad attached to the inner surface of the headband about an intersection of the top portion and the side portion; wherein at least one of the rear pad and the brow pad comprises a first layer of a first cushioning material having a first durometer, and a second layer of a second cushioning material having a second durometer that is harder than the first durometer. In some embodiments of the headlight device, the first cushioning material is silicone foam having a first durometer, and the second cushioning material is silicone foam having a second durometer that is harder than the first durometer. In some embodiments of the headlight device, the second layer of the second cushioning material is closer than the first layer of the first cushioning material to the inner surface of the rear portion of the headband. In some embodiments of the headlight device, the first layer of the first cushioning material and the second layer of the second cushioning material are each perforated. In some embodiments of the headlight device, the majority of the perforations in the first layer of the first cushioning material are generally circular, and the majority of the perforations in the second layer of the second cushioning material are in a shape other than circular. In some embodiments of the headlight device, the perforations in the second layer of the second cushioning material are generally square or rectangular, or generally in a grid-like pattern. In some embodiments of the headlight device, the second layer of the second cushioning material has more open space on its upper or lower surface due to perforations than the first layer of the first cushioning material. In some embodiments of the headlight device, the total volume of cavity due to perforations in the second layer of the second cushioning material is higher than the total volume of cavity in the first layer of the first cushioning material. In some embodiments of the headlight device, the rear pad has an inner surface in contact with an wearer and an outer surface attached to the inner surface of the rear portion of the headband, and the rear pad comprises a recess on its inner surface. In some embodiments of the headlight device, at least one of the top pad and the side pad comprises urethane foam and forms segments. In some embodiments of the headlight device, at least one of the top pad, the side pad, and the rear pad is spaced apart from a surface of a head of a wearer of the head wearable device at a suture between adjacent plates of a skull of the wearer of the head wearable device. In some embodiments of the headlight device, the first cushioning material comprises an extra firm silicone foam, the first durometer of which has a compression force deflection in a range of 16-26 pounds per square inch (psi), and wherein the second cushioning material comprises a different silicone foam, the second durometer of which has a compression force deflection in a range of 1-20 psi. In some embodiments of the headlight device, the first cushioning material comprises a firm silicone foam, the first durometer of which has a compression force deflection in a range of 12-20 pounds per square inch (psi), and wherein the second cushioning material comprises a different silicone foam, the second durometer of which has a compression force deflection in a range of 1-14 or 16-26 psi. In some embodiments of the headlight device, the first cushioning material comprises a medium silicone foam, the first durometer of which has a compression force deflection in a range of 6-14 pounds per square inch (psi), and wherein the second cushioning material comprises a different silicone foam, the second durometer of which has a compression force deflection in a range of 1-7 or 12-26 psi. In some embodiments of the headlight device, the first cushioning material comprises a firm silicone foam, the first durometer of which has a compression force deflection in a range of 2-7 pounds per square inch (psi), and wherein the second cushioning material comprises a different silicone foam, the second durometer of which has a compression force deflection in a range of 1-5 or 6-26 psi. In some embodiments of the headlight device, the first cushioning material comprises a firm silicone foam, the first durometer of which has a compression force deflection in a range of 1-5 pounds per square inch (psi), and wherein the second cushioning material comprises a different silicone foam, the second durometer of which has a compression force deflection in a range of about 1.5 or 2-26 psi. In some embodiments of the headlight device, the first cushioning material comprises a firm silicone foam, the first durometer of which has a compression force deflection of about 1.5 pounds per square inch (psi), and wherein the second cushioning material comprises a different silicone foam, the second durometer of which has a compression force deflection in a range of 1-26 psi.

In some aspects, a headlight device comprises a headband for encircling the head of a wearer; a padding system comprising a pad removably attached to at least a portion of the headband; wherein the pad comprises a first layer of a first cushioning material having a first durometer, and a second layer of a second cushioning material having a second durometer that is harder than the first durometer; and wherein the first layer is perforated in a first perforation pattern, and the second layer is perforated in a second perforation pattern that differs from the first perforation pattern. In some embodiments of the headlight device, the first layer of the first cushioning material is a layer of silicone foam having a first durometer, and the second layer of the second cushioning material is a layer of silicone foam having a second durometer that is harder than the first durometer. In some embodiments of the headlight device, the second layer of the second cushioning material is closer than the first layer of the first cushioning material to the inner surface of the rear portion of the headband. In some embodiments of the headlight device, the majority of the perforations in one of the first and second layers are circular, and the majority of the perforations in the other layer are in a shape other than circular. In some embodiments of the headlight device, the perforations in the other layer are generally square or rectangular or generally in a grid-like pattern. In some embodiments of the headlight device, the second layer of the second cushioning material has more open space on its upper or lower surface due to perforations than the first layer of the first cushioning material. In some embodiments of the headlight device, the total volume of cavity due to perforations in the second layer of the second cushioning material is higher than the total volume of cavity in the first layer of the first cushioning material. In some embodiments of the headlight device, the pad is spaced apart from a surface of a head of a wearer of the head wearable device at a suture between adjacent plates of a skull of the wearer of the head wearable device. In some embodiments of the headlight device, the first cushioning material comprises an extra firm silicone foam, the first durometer of which has a compression force deflection in a range of 16-26 pounds per square inch (psi), and wherein the second cushioning material comprises a different silicone foam, the second durometer of which has a compression force deflection in a range of 1-20 psi. In some embodiments of the headlight device, the first cushioning material comprises a firm silicone foam, the first durometer of which has a compression force deflection in a range of 12-20 pounds per square inch (psi), and wherein the second cushioning material comprises a different silicone foam, the second durometer of which has a compression force deflection in a range of 1-14 or 16-26 psi. In some embodiments of the headlight device, the first cushioning material comprises a medium silicone foam, the first durometer of which has a compression force deflection in a range of 6-14 pounds per square inch (psi), and wherein the second cushioning material comprises a different silicone foam, the second durometer of which has a compression force deflection in a range of 1-7 or 12-26 psi. In some embodiments of the headlight device, the first cushioning material comprises a firm silicone foam, the first durometer of which has a compression force deflection in a range of 2-7 pounds per square inch (psi), and wherein the second cushioning material comprises a different silicone foam, the second durometer of which has a compression force deflection in a range of 1-5 or 6-26 psi. In some embodiments of the headlight device, the first cushioning material comprises a firm silicone foam, the first durometer of which has a compression force deflection in a range of 1-5 pounds per square inch (psi), and wherein the second cushioning material comprises a different silicone foam, the second durometer of which has a compression force deflection in a range of about 1.5 or 2-26 psi. In some embodiments of the headlight device, the first cushioning material comprises a firm silicone foam, the first durometer of which has a compression force deflection of about 1.5 pounds per square inch (psi), and wherein the second cushioning material comprises a different silicone foam, the second durometer of which has a compression force deflection in a range of 1-26 psi.

In some aspects, a method is provided of cooling a luminaire of a head wearable device comprises providing an LED within a luminaire housing; forming at least one air inlet in the luminaire housing; attaching a heatsink to a substrate to which the LED is mounted; arranging the heatsink adjacent the at least one air inlet of the luminaire housing; connecting the luminaire housing to a ball joint; forming a hole and an exhaust port in the ball joint; connecting a first end of the flexible duct to the ball joint at the exhaust port; connecting a rigid duct to the flexible duct at the second end of the flexible duct; installing the air moving device within a hot air exhaust of the upper housing; monitoring the temperature of the LED within the luminaire; and controlling the air moving device to produce an air flow to cool the LED. In some embodiments, the method comprises attaching the upper housing to a top surface of a headpiece of the head wearable device. In some embodiments, the method comprises attaching a power cord to the upper housing to receive power from a holster. In some embodiments, the method comprises adjusting an intensity of light output from the at least one light source via the holster, wherein the power comprises a rechargeable battery or a continuous power source. In some embodiments of the method, the headpiece comprises a headband, which has at least a top strap and two lateral straps, and an occipital basket, wherein the headband is connected to the occipital basket and the headband and the occipital basket are independently adjustable relative to each other. In some embodiments, the method comprises attaching the luminaire to a headpiece via a mechanical linkage, such that an angle and/or position of the luminaire relative to the headpiece is adjustable. In some embodiments of the method, the flexible duct comprises a corrugated construction such that a length thereof can be shortened or lengthened as the angle and/or position of the luminaire relative to the headpiece is adjusted. In some embodiments, the method comprises monitoring, via a controller, a temperature of the at least one light source and modulating an operational setting of the air moving device to maintain the temperature of the at least one light source within a predetermined operating range. In some embodiments of the method, the at least one light source comprises a light emitting diode (LED). In some embodiments of the method, connecting the luminaire housing to the ball joint comprises a pivotable and/or swivelable connection. In some embodiments, the method comprises defining, via the ball joint, a range of angular motion for the luminaire and comprises a passage and an exhaust port formed in a circumferential wall of the ball joint, wherein the range of angular motion is such that the passage remains in a position to provide an air flow path from the luminaire housing into the ball joint. In some embodiments, the method comprises arranging the passage and the exhaust port on substantially opposite sides of the ball joint. In some embodiments of the method, the passage is not externally visible from the luminaire housing at any point along the range of angular motion. In some embodiments, the method comprises arranging a heatsink within the luminaire housing. In some embodiments, the method comprises optimizing a projection of white light and restricting both stray light reflections and yellow light from exiting the lens cell. In some embodiments, the method comprises producing, via the lens cell, a substantially homogeneous white-spot presentation. In some embodiments of the method, the lens cell comprises an adjustable focal length and/or focal point.

In some further aspects, a headlight device is provided, the headlight device comprising: a headband for encircling the head of a wearer; a padding system comprising a rear pad removably attached to at least a portion of the headband; wherein the rear pad comprises a first layer of a first cushioning material having a first durometer, and a second layer of a second cushioning material having a second durometer that is different from the first durometer; wherein the first layer is perforated in a first perforation pattern, and the second layer is perforated in a second perforation pattern that differs from the first perforation pattern; wherein the first layer comprises an inner surface in contact with a wearer; wherein the second layer comprises an outer surface attached to the inner surface of the rear portion of the headband; and wherein the rear pad comprises a recess on an inner surface thereof.

While the embodiments disclosed herein are provided merely for purposes of illustration, the features included in each of these embodiments may be combined in any possible combination, as would be readily understood by those having ordinary skill in the art.

While at least one example embodiment of the invention(s) is disclosed herein, it should be understood that modifications, substitutions and alternatives may be apparent to one of ordinary skill in the art and can be made without departing from the scope of this disclosure. This disclosure is intended to cover any adaptations or variations of the example embodiment(s). In addition, in this disclosure, the terms "comprise" or "comprising" do not exclude other elements or steps, the terms "a", "an" or "one" do not exclude a plural number, and the term "or" means either or both. Furthermore, characteristics or steps which have been described may also be used in combination with other characteristics or steps and in any order unless the disclosure or context suggests otherwise.

The invention claimed is:

1. A head wearable device comprising:
a headpiece comprising:
  a headband comprising a top strap and at least two lateral straps;
  an occipital basket attached to the headband;
  a first housing attached to an outer surface of the top strap of the headband;
  a depth adjuster attached to the first housing;
    wherein the depth adjuster is configured to change a distance between the occipital basket and the first housing; and
    wherein a depth of the headpiece changes when the distance between the occipital basket and the first housing changes; and
  a second housing attached to an outer surface of the occipital basket; and
  a headband adjuster attached to the occipital basket, wherein the headband adjuster is configured to change a circumference of the headpiece.

2. The head wearable device of claim 1, comprising, on at least a first portion of the occipital basket, a first visual index comprising a first plurality of characters, each of which correspond to one of a plurality of predetermined depth settings of the headpiece, and, on at least a second portion of the occipital basket, a second visual index comprising a second plurality of characters, each of which correspond to one of a plurality of predetermined circumferential settings of the headpiece, wherein the first and second visual indexes comprise alphanumeric characters.

3. The head wearable device of claim 2, wherein the first visual index and the second visual index comprise different ranges and/or types of alphanumeric characters.

4. The head wearable device of claim 3, wherein the first visual index comprises a plurality of sequential letters and the second visual index comprises a plurality of sequential numbers.

5. The head wearable device of claim 3 wherein the first visual index comprises a plurality of sequential numbers and the second visual index comprises a plurality of sequential letters.

6. The head wearable device of claim 1, comprising padding on an inner surface of the headband and the occipital basket.

7. The head wearable device of claim 6, wherein a notch is formed in a lower edge of the occipital basket, the notch being configured to prevent hair or a cap of a wearer from interfering with proper fitment of the headpiece about a head of the wearer.

8. The head wearable device of claim 7, wherein the padding on the occipital basket comprises a recessed area configured to prevent the hair or cap of the wearer from interfering with proper fitment of the headpiece about the head of the wearer.

9. The head wearable device of claim 6, wherein the padding is removably attached to the headband and/or the occipital basket.

10. The head wearable device of claim 6, wherein the padding is configured to be positioned spaced about and/or over a head of a wearer of the head wearable device without covering or being positioned over a suture between adjacent plates of a skull of the wearer of the head wearable device.

11. A method of adjusting a size of a headpiece of a head wearable device to a head size of a wearer, the headpiece comprising a headband and an occipital basket, the method comprising:
  attaching a first housing to a top strap of the headband;
  inserting a first portion of the occipital basket at least partially into the first housing;
  adjusting a depth of the headpiece to correspond to the head size of the wearer;
  attaching a second housing to the occipital basket;
  inserting at least a second portion of the occipital basket into the second housing to define a circumference of the headpiece; and
  adjusting the circumference of the headpiece.

12. The method of claim 11, comprising:
  providing a first visual index along a length of the first portion of the occipital basket, the first visual index comprising alphanumeric characters to designate predetermined depth settings for the headpiece;
  providing a second visual index along a length of the second portion of the occipital basket, the second visual index comprising alphanumeric characters to designate predetermined circumference settings for the headpiece;
  determining a wearer preference for the depth and/or the circumference of the headpiece corresponding to the first and second visual indexes;
  placing the head wearable device on the wearer's head;
  adjusting the depth of the headpiece such that the first visual index indicates that the wearer preference for the depth of the headpiece has been achieved; and/or
  adjusting the circumference of the headpiece such that the second visual index indicates that the wearer preference for the circumference of the headpiece has been achieved.

13. The method of claim 12, wherein the first visual index and the second visual index comprise different ranges and/or types of alphanumeric characters.

14. The method of claim 13, wherein:
  the first visual index comprises a plurality of sequential letters;
  the second visual index comprises a plurality of sequential numbers; and
  the wearer preference for the depth and the circumference of the headpiece is designated by one of the plurality of sequential letters and one of the plurality of sequential numbers, respectively.

15. The method of claim 13, wherein the first visual index comprises a plurality of sequential numbers and the second visual index comprises a plurality of sequential letters.

16. The method of claim 11, comprising attaching padding on an inner surface of the headband and the occipital basket.

17. The method of claim 16, comprising forming a notch in a lower edge of the occipital basket to prevent hair or a cap of the wearer from interfering with proper fitment of the headpiece about a head of the wearer.

18. The method of claim 17, comprising forming a recessed area in the padding on the occipital basket to prevent the hair or cap of the wearer from interfering with proper fitment of the headpiece about the head of the wearer.

19. The method of claim 16, wherein the padding is removably attached to the headband and/or the occipital basket.

20. The method of claim 16, comprising positioning the padding such that the padding can be positioned about and/or over a head of the wearer of the head wearable device without covering or being positioned over a suture between adjacent plates of a skull of the wearer of the head wearable device.

* * * * *